(12) United States Patent
Jurica et al.

(10) Patent No.: US 10,717,725 B2
(45) Date of Patent: *Jul. 21, 2020

(54) PYRROLIDINE GPR40 MODULATORS

(71) Applicant: BRISTOL-MYERS SQUIBB COMPANY, Princeton, NJ (US)

(72) Inventors: Elizabeth Anne Jurica, Robbinsville, NJ (US); Zhenqiu Hong, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/211,848

(22) Filed: Dec. 6, 2018

(65) Prior Publication Data
US 2019/0112293 A1  Apr. 18, 2019

Related U.S. Application Data

(63) Continuation of application No. 15/840,198, filed on Dec. 13, 2017, now abandoned, which is a continuation of application No. 14/705,524, filed on May 6, 2015, now Pat. No. 9,873,679.

(60) Provisional application No. 61/989,651, filed on May 7, 2014.

(51) Int. Cl.
| C07D 401/14 | (2006.01) |
| C07D 401/12 | (2006.01) |
| A61K 31/506 | (2006.01) |
| A61K 31/4545 | (2006.01) |
| A61K 45/06 | (2006.01) |
| A61K 31/454 | (2006.01) |

(52) U.S. Cl.
CPC .......... *C07D 401/14* (2013.01); *A61K 31/454* (2013.01); *A61K 31/4545* (2013.01); *A61K 31/506* (2013.01); *A61K 45/06* (2013.01); *C07D 401/12* (2013.01)

(58) Field of Classification Search
CPC .... C07D 401/12; C07D 401/14; A61K 45/06; A61K 31/454; A61K 31/4545; A61K 31/506
USPC ...................................................... 514/274
See application file for complete search history.

(56) References Cited

U.S. PATENT DOCUMENTS

| 5,614,492 | A | 3/1997 | Habener | |
| 8,288,404 | B2* | 10/2012 | Ellsworth | C07D 207/08 514/275 |
| 9,133,163 | B2 | 9/2015 | Ellsworth et al. | |
| 9,604,964 | B2 | 3/2017 | Ellsworth et al. | |
| 9,656,963 | B2 | 5/2017 | Hernandez et al. | |
| 9,714,231 | B2* | 7/2017 | Ellsworth | C07D 401/14 |
| 9,873,679 | B2* | 1/2018 | Jurica | C07D 401/14 |
| 2017/0081282 | A1 | 3/2017 | Ye et al. | |

FOREIGN PATENT DOCUMENTS

| CL | 201602815 | 12/2015 |
| WO | WO2011/044073 A1 | 4/2011 |
| WO | WO2014/022253 A1 | 2/2014 |
| WO | WO2014/078609 A1 | 5/2014 |
| WO | WO2014/078610 A1 | 5/2014 |
| WO | WO2014/078611 A1 | 5/2014 |

OTHER PUBLICATIONS

Office Action Issued in the corresponding application in China—dated Mar. 19, 2019.
Arbeeny, C. et al., "The Metabolic Syndrome: From Pathophysiology to Novel Treatment Strategies", Curr. Med. Chem.-Imm., Endoc. & Metab. Agents, vol. 1, No. 1, pp. 1-24 (2001).
Barlind, J.G. et al., "Identification and design of a novel series of MGAT2 inhibitors", Bioorganic & Medicinal Chemistry Letters, vol. 23, pp. 2721-2726 (2013).
Basu, A. et al., GPR40 Modulators: New kid on the Block. Diabetes Care. 2013, vol. 36, p. 185.
Bellina, F. et al., "Synthesis and biological activity of pyrrole, pyrroline and pyrrolidine derivatives with two aryl groups on adjacent positions", Tetrahedron, vol. 62, pp. 7213-7256 (2006).
Bertrand, M.B. et al., "Mild Conditions for Pd-Catalyzed Carboamination of N-Protected Hex-4-enylamines and 1-, 3-, and 4-Substituted Pent-4-enylamines. Scope, Limitations, and Mechanism of Pyrrolidine Formation", J. Org. Chem., vol. 73, No. 22, pp. 8851-8860 (2008).
Browning, R.G. et al., "Palladium-catalyzed aryl-amidation. Synthesis of non-racemic N-aryl lactams", Tetrahedron, vol. 60, pp. 359-365 (2004).
Bundgaard, H., Chapter 5: "Design and Application of Prodrugs", A Textbook of Drug Design and Development, pp. 113-191, Krogsgaard-Larsen, P. et al., eds., Harwood Academic Publishers, publ. (1991).
Bundgaard, H., ed., Design of Prodrugs, Elsevier Science Publishers B.V., publ. (1985).

(Continued)

*Primary Examiner* — Yong L Chu
(74) *Attorney, Agent, or Firm* — Jing G. Sun

(57) ABSTRACT

The present invention provides compounds of Formula (I):

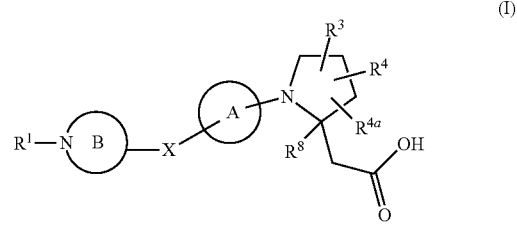

or a stereoisomer, a tautomer, a pharmaceutically acceptable salt, a polymorph, or a solvate thereof, wherein all of the variables are as defined herein. These compounds are GPR40 G protein-coupled receptor modulators which may be used as medicaments.

20 Claims, No Drawings

(56) References Cited

OTHER PUBLICATIONS

Bundgaard, H., "Prodrugs as a means to improve the delivery of peptide drugs", Advanced Drug Delivery Reviews, vol. 8, pp. 1-38 (1992).
Carey, FA. Organic Chemistry 6th Ed. McGraw Hill. 2006, chapter 1, p. 9.
Coldham, I. et al., "Synthesis of Pyrrolidines by Anionic Cyclization onto Allylic Ethers, Alkynes and Carboxylic Groups", Tetrahedron Letters, vol. 38, No. 43, pp. 7621-7624 (1997).
Cordero, F.M. et al., "Synthesis of α-Cyclopropyl-β-homoprolines", J. Org. Chem., vol. 74, No. 11, pp. 4225-4231 (2009).
Deng, Q.-H. et al., "Ruthenium-Catalyzed One-Pot Carbenoid N-H Insertion Reactions and Diastereoselective Synthesis of Prolines", Organic Letters, vol. 10, No. 8, pp. 1529-1532 (2008).
Edfalk, S. et al., "*Gpr*40 is Expressed in Enteroendocrine Cells and Mediates Free Fatty Acid Stimulation of Incretin Secretion", Diabetes, vol. 57, pp. 2280-2287 (2008).
Elangbam, C.S., "Review Paper: Current Strategies in the Development of Anti-obesity Drugs and Their Safety Concerns", Vet. Pathol., vol. 46, No. 1, pp. 10-24 (2009).
Evans, G.L. et al., "Synthesis of Ecgoninic Acid and Related Pyrrolidones", Journal of the American Chemical Society, vol. 72, pp. 2727-2728 (1950).
Ford, E.S. et al., "Prevalence of the Metabolic Syndrome Among US Adults: Findings from the Third National Health and Nutrition Examination Survey", Journal of the American Medical Association, vol. 287, No. 3, pp. 356-359 (2002).
Fyfe, M.C.T. et al., "Glucokinase Activators as Potential Antidiabetic Agents Possessing Superior Glucose-Lowering Efficacy", Drugs of the Future, vol. 34, No. 8, pp. 641-653 (2009).
Galliford, C.V. et al., "Catalytic, Three-Component Assembly Reaction for the Synthesis of Pyrrolidines", Organic Letters, vol. 5, No. 19, pp. 3487-3490 (2003).
Hoang, C.T. et al., "Amino Acid Homologation by the Blaise Reaction: A New Entry into Nitrogen Heterocycles", J. Org. Chem., vol. 74, No. 11, pp. 4177-4187 (2009).
Itoh, Y. et al., "Free fatty acids regulate insulin secretion from pancreatic β cells through GPR40", Nature, vol. 422, pp. 173-176 (2003).
Jones, D., "Novel pharmacotherapies for obesity poised to enter market", Nature Reviews: Drug Discovery, vol. 8, pp. 833-834 (2009).
Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).
Kimball, F.S. et al., "Enantiospecific synthesis and cytotoxicity of 7-(4-methoxyphenyl)-6-phenyl-2,3,8,8a-tetrahydroindolizin-5(1*H*)-one enantiomers", Bioorganic & Medicinal Chemistry, vol. 16, pp. 4367-4377 (2008).
Kimura, M. et al., "Convenient Synthesis of Pyrrolidines by Amphiphilic Allylation of Imines with 2-Methylenepropane-1,3-diols", Angew. Chem. Int. Ed., vol. 47, pp. 5803-5805 (2008).
Larock, R.C., Comprehensive Organic Transformations: A Guide to Functional Group Preparations, pp. xiii-xxviii, VCH Publishers, Inc., publ. (1989).
Larock, R.C. et al., "Synthesis of Pyrrolidines and Piperidines via Palladium-Catalyzed Coupling of Vinylic Halides and Olefinic Sulfonamides", J. Org. Chem., vol. 59, No. 15, pp. 4172-4178 (1994).
Lewis, Sr., R.J., Hawley's Condensed Chemical Dictionary, Thirteenth Edition, John Wiley & Sons, Inc., publ. (1997).
Luly, J.R. et al., "Routes to Mitomycins. New Syntheses of the 2,3,5,8-Tetrahydro-5,8-dioxo-1*H*-pyrrolo[1,2-*a*]indole Ring System. An Efficient Synthesis of 7-Methoxymitosene", J. Am. Chem. Soc., vol. 105, No. 9, pp. 2859-2866 (1983).
Luo, S. et al., "The Cotton Centromere Contains a Ty3-*gypsy*-like LTR Retroelement", PLoS ONE, vol. 7, No. 4, pp. 1-10 (2012).
Melnikova, I. et al., "Anti-obesity therapies", Nature Reviews Drug Discovery, 5, pp. 369-370 (2006).
Mizuno, C.S. et al., "Type 2 Diabetes and Oral Antihyperglycemic Drugs", Current Medicinal Chemistry, vol. 15, No. 1, pp. 61-74 (2008).
Mohler, M.L. et al., "Recent and Emerging Anti-Diabetes Targets", Medicinal Research Reviews, vol. 29, No. 1, pp. 125-195 (2009).
Nájera, C. et al., "Catalytic Enantioselective 1,3-Dipolar Cycloaddition Reaction of Azomethine Ylides and Alkenes: The Direct Strategy to Prepare Enantioenriched Highly Substituted Proline Derivatives", Angew. Chem. Int. Ed., vol. 44, pp. 6272-6726 (2005).
NCBI Reference Sequence No. NM_005303, Kristinsson, H. et al., Feb. 20, 2014.
NCBI Reference Sequence No. NM_194057, Shen, X. et al., May 24, 2014.
Ney, J.E. et al., "Synthesis of *N*-Aryl-2-allylpyrrolidines via Palladium-Catalyzed Carboamination Reactions of γ-(*N*-Arylamino)alkenes with Vinyl Bromides", Adv. Synth. Catal., vol. 347, pp. 1614-1620 (2005).
Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).
Obici, S., "Minireview: Molecular Targets for Obesity Therapy in the Brain", Endocrinology, vol. 150, No. 6, pp. 2512-2517 (2009).
Paderes, M.C. et al., "Diastereoselective Pyrrolidine Synthesis via Copper Promoted Intramolecular Aminooxygenation of Alkenes: Formal Synthesis of (+)-Monomorine", Organic Letters, vol. 11, No. 9, pp. 1915-1918 (2009).
Pisaneschi, F. et al., "Click Chemistry: A Straightforward Route to Decorated Prolines", Synlett, vol. 18, pp. 2882-2884 (2007).
Qiu, X. et al., "Practical Synthesis of Boc-Protected *cis*-4-Trifluoromethyl and *cis*-4-Difluoromethyl-[- prolines", J. Org. Chem., vol. 67, No. 20, pp. 7162-7164 (2002).
Ray, J.K. et al., "Structurally Designed Novel Furogamma Lactams as Inhibitors for Bacterial Propagations", Bioorganic & Medicinal Chemistry, vol. 2, No. 12, pp. 1417-1421 (1994).
Sasaki, N.A., Chapter 28: "A Novel Synthetic Protocol for the Preparation of Enantiopure 3-, 4-, and 5-Substituted Prolines", Methods in Molecular Medicine: Peptidomimetics Protocols, vol. 23, pp. 489-512, Kazmierski, W.M., ed., Humana Press Inc., publ. (1999).
Schlummer, B. et al., "Bronsted Acid-Catalyzed Intramolecular Hydroamination of Protected Alkenylamines. Synthesis of Pyrrolidines and Piperidines", Organic Letters, vol. 4, No. 9, pp. 1471-1474 (2002).
Semmelhack, M.F., ed., Comprehensive Organic Synthesis: Selectivity, Strategy & Efficiency in Modern Organic Chemistry, vol. 4: "Additions to and Substitutions at C—C π-Bonds", pp. v-vi, Pergamon Press, Inc., publ. (1991).
Sharma, N. et al., Recent Advances in Development. Mini Rev. Med Chem. 2017, vol. 17, abstract.
Shimpukade, B. et al., "Discovery of a Potent and Selective GPR120 Agonist", Journal of Medicinal Chemistry, vol. 55, pp. 4511-4515 (2012).
Smith, M.B. et al., March's Advanced Organic Chemistry: Reactions, Mechanisms, and Structure, Sixth Edition, John Wiley & Sons, Inc. (2007).
Spangenberg, T. et al., "Hydroformylation of Homoallylic Azides: A Rapid Approach toward Alkaloids", Organic Letters, vol. 11, No. 2, pp. 261-264 (2009).
Stephens, B.E. et al., "A Regio- and Diastereoselective Intramolecular Nitrone Cycloaddition for Practical 3- and 2,3-Disubstituted Piperidine Synthesis from γ-Butyrolactone", J. Org. Chem., vol. 74, No. 1, pp. 254-263 (2009).
Tan, C.P. et al., "Selective Small-Molecule Agonists of G Protein-Coupled Receptor 40 Promote Glucose-Dependent Insulin Secretion and Reduce Blood Glucose in Mice", Diabetes, vol. 57, pp. 2211-2219 (2008).

(56) References Cited

OTHER PUBLICATIONS

Testa, B. et al., Hydrolysis in Drug and Prodrug Metabolism: Chemistry, Biochemistry, and Enzymology, pp. xi-xx, Wiley-VCH GmbH & Co., publ. (2003).
Wang, Y.-G. et al., "Organocatalytic Approach to Enantioselective One-Pot Synthesis of Pyrrolidine, Hexahydropyrrolizine, and Octahydroindolizine Core Structures", Organic Letters, vol. 11, No. 9, pp. 2027-2029 (2009).
West, AR. Solid State Chemistry and its Applications. John Wiley and Sons, LTD. 1990, p. 358.
Widder, K.J. et al., eds., Section III: "Prodrugs", Methods in Enzymology, vol. 112, pp. 309-396, Academic Press, Inc., publ. (1985).
Wolfe, J.P., "Palladium-Catalyzed Carboetherification and Carboamination Reactions of γ-Hydroxy- and γ-Aminoalkenes for the Synthesis of Tetrahydrofurans and Pyrrolidines", Eur. J. Org. Chem., pp. 571-582 (2007).
Yamashima, T., "A putative link of PUFA, GPR40 and adult-born hippocampal neurons for memory", Progress in Neurobiology, vol. 84, pp. 105-115 (2008).
Zhou, J.-Q. et al., "Synthesis of Pyrrolidines and Pyrrolidinones by the Rhodium Complex Catalyzed Cyclization of Unsaturated Amines", J. Org. Chem., vol. 57, pp. 3328-3331 (1992).
Shen, W. et al., "Research progress in G protein-coupled receptor 40", Hereditas (Beijing), vol. 35(1), pp. 27-34 (2013).

\* cited by examiner

PYRROLIDINE GPR40 MODULATORS

CROSS-REFERENCE TO RELATED APPLICATIONS

This application is a continuation application of U.S. Ser. No. 15/840,198, filed Dec. 13, 2017, which is a continuation application of U.S. Ser. No. 14/705,524, filed May 6, 2015, now U.S. Pat. No. 9,873,679, which claims priority to U.S. Provisional Application Ser. No. 61/989,651, filed May 7, 2014; the contents of which are herein incorporated by reference in their entirety.

FIELD OF THE INVENTION

The present invention provides novel carboxylic acid substituted pyrrolidine compounds, and their analogues thereof, which are GPR40 G protein-coupled receptor modulators, compositions containing them, and methods of using them, for example, for the treatment of diabetes and related conditions.

BACKGROUND OF THE INVENTION

Diabetes mellitus is a progressively debilitating disorder of epidemic proportions leading to various micro- and macrovascular complications and morbidity. The most common type of diabetes, type 2 diabetes, is characterized by increasing insulin resistance associated with inadequate insulin secretion after a period of compensatory hyperinsulinemia. Free fatty acids (FFAs) are evidenced to influence insulin secretion from β cells primarily by enhancing glucose-stimulated insulin secretion (GSIS). G-protein coupled receptors (GPCRs) expressed in β cells are known to modulate the release of insulin in response to changes in plasma glucose levels. GPR40, also known as fatty acid receptor 1 (FFAR1), is a membrane-bound FFA receptor which is preferentially expressed in the pancreatic islets and specifically in β cells and mediates medium to long chain fatty acid induced insulin secretion. GPR40 is also expressed in enteroendocrine cells wherein activation promotes the secretion of gut incretin hormones, such as GLP-1, GIP, CCK and PYY. To decrease medical burden of type 2 diabetes through enhanced glycemic control, GPR40 modulator compounds hold the promise of exerting an incretin effect to promote GSIS as well as potential combination with a broad range of antidiabetic drugs.

The present invention relates to novel substituted pyrrolidine compounds which have the ability to modulate GPR40. Such compounds are therefore potentially useful for the treatment of diabetes and related conditions.

SUMMARY OF THE INVENTION

The present invention provides substituted pyrrolidine compounds, and their analogues thereof, which are useful as GPR40 modulators, including stereoisomers, tautomers, pharmaceutically acceptable salts, polymorphs, or solvates thereof.

The present invention also provides processes and intermediates for making the compounds of the present invention or stereoisomers, tautomers, pharmaceutically acceptable salts, polymorphs, or solvates thereof.

The present invention also provides pharmaceutical compositions comprising a pharmaceutically acceptable carrier and at least one of the compounds of the present invention or stereoisomers, tautomers, pharmaceutically acceptable salts, polymorphs, or solvates thereof.

The present invention also provides a crystalline form of one of the compounds of the present invention or stereoisomers, tautomers, pharmaceutically acceptable salts, polymorphs, or solvates thereof.

The compounds of the invention may be used in the treatment of multiple diseases or disorders associated with GPR40, such as diabetes and related conditions, microvascular complications associated with diabetes, the macrovascular complications associated with diabetes, cardiovascular diseases, Metabolic Syndrome and its component conditions, disorders of glucose metabolism, obesity and other maladies.

The compounds of the invention may be used in therapy.

The compounds of the invention may be used for the manufacture of a medicament for the treatment of multiple diseases or disorders associated with GPR40.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

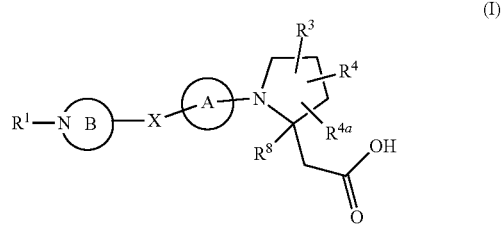

or a stereoisomer, a tautomer, a pharmaceutically acceptable salt, a polymorph, or a solvate thereof, wherein X is independently selected from: a bond, O, S, NH, $N(C_{1-4}$ alkyl$)$, $CH_2$, $CH_2CH_2$, $CH(C_{1-4}$ alkyl$)$, $OCH_2$, $CH_2O$, $OCH_2CH_2$, and $CH_2CH_2O$;

ring A is independently

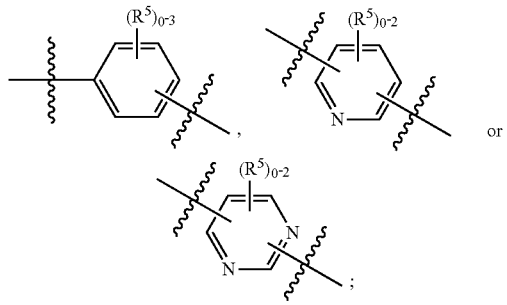

ring B is independently a 4- to 7-membered saturated heterocycle containing carbon atoms, the nitrogen atom shown in the ring B and 0-1 additional heteroatom selected from N, O, and S; and ring B is substituted with 0-4 $R^2$;

$R^1$ is independently

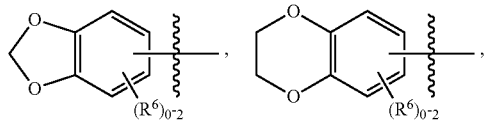

phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-6}$ alkyl substituted with 0-1 $R^{12}$, $C_{1-6}$ alkoxy substituted with 0-1 $R^{12}$, $C_{1-4}$ haloalkyl substituted with 0-1 $R^{12}$, $C_{1-4}$ haloalkoxy substituted with 0-1 $R^{12}$, $-(CH_2)_m-C_{3-6}$ carbocycle substituted with 0-1 $R^{12}$, and $-(CH_2)_m-$(5- to 10-membered heteroaryl containing carbon atoms and 1-4 heteroatoms selected from N, $NR^{11}$, O, and S); wherein said heteroaryl is substituted with 0-1 $R^{12}$;

when two $R^2$ groups are attached to two different carbon atoms, they may combine to form a 1- to 3-membered carbon atom bridge over ring B;

when two $R^2$ groups are attached to the same carbon, they may combine, together with the carbon atom to which they are attached, to form a 3- to 6-membered carbon atom containing spiro ring;

$R^3$ is independently selected from: $C_{1-6}$ alkyl substituted with $R^{10}$, $C_{2-6}$ alkenyl substituted with $R^{10}$, $C_{2-6}$ alkynyl substituted with $R^{10}$, $C_{1-4}$ haloalkyl substituted with $R^{10}$, $-O(CH_2)_{1-2}O(CH_2)_{1-4}R^{10}$, $OR^9$, $SR^9$, $C(O)OR^9$, $CO_2R^9$, $S(O)R^9$, $SO_2R^9$, and $CONHR^9$;

$R^4$ and $R^{4a}$ are independently selected from: H, halogen, $C_{1-6}$ alkyl, $C_{1-6}$ alkoxy, and $-(CH_2)_m-C_{3-6}$ carbocycle;

$R^5$, at each occurrence, is independently selected from: halogen, $C_{1-6}$ alkyl, $C_{1-6}$ alkoxy, $C_{1-6}$ haloalkyl, and $C_{1-6}$ haloalkoxy;

$R^6$, at each occurrence, is independently selected from: halogen, OH, $C_{1-4}$ alkylthio, CN, $SO_2(C_{1-2}$ alkyl), $N(C_{1-4}$ alkyl$)_2$, $C_{1-4}$ haloalkyl, $C_{1-4}$ haloalkoxy, $C_{1-8}$ alkyl substituted with 0-1 $R^7$, $C_{1-6}$ alkoxy substituted with 0-1 $R^7$, $-(O)_n-(CH_2)_m-(C_{3-10}$ carbocycle substituted with 0-2 $R^7$), and $-(CH_2)_m-$(5- to 10-membered heteroaryl containing carbon atoms and 1-4 heteroatoms selected from N, $NR^{11}$, O, and S); wherein said heteroaryl is substituted with 0-2 $R^7$;

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl$)_2$, $SO_2(C_{1-2}$ alkyl), and phenyl;

$R^8$ is independently selected from: H and $C_{1-4}$ alkyl;

$R^9$, at each occurrence, is independently selected from: $C_{1-6}$ alkyl substituted with substituted with $R^{10}$, and $C_{1-4}$ haloalkyl substituted with $R^{10}$;

$R^{10}$, at each occurrence, is independently selected from: CN, $C_{1-4}$ alkoxy, $C_{1-4}$ haloalkoxy, $CO_2(C_{1-4}$ alkyl), $SO_2(C_{1-4}$ alkyl), and tetrazolyl;

$R^{11}$, at each occurrence, is independently selected from: H, $C_{1-4}$ alkyl and benzyl;

$R^{12}$, at each occurrence, is independently selected from: OH, halogen, CN, $C_{1-4}$ alkyl, $C_{1-4}$ alkoxy, $C_{1-4}$ haloalkyl, $C_{1-4}$ haloalkoxy, $CO_2(C_{1-4}$ alkyl), and tetrazolyl;

m, at each occurrence, is independently 0, 1, or 2; and
n, at each occurrence, is independently 0 or 1.

In a second aspect, the present disclosure provides a compound of Formula (I), wherein $R^4$ is hydrogen and $R^8$ is hydrogen, further characterized by Formula (II):

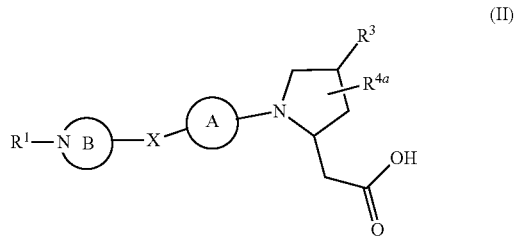

or a stereoisomer, a tautomer, a pharmaceutically acceptable salt, a polymorph, or a solvate thereof, wherein X is independently selected from: O, $N(CH_3)$, $CH_2$, $CH_2O$, and $CH_2CH_2O$;

ring A is independently

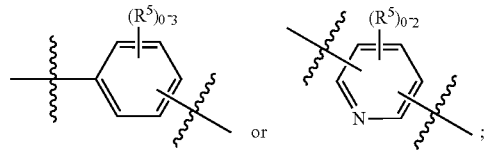

ring B is independently a 4- to 7-membered saturated heterocycle containing carbon atoms and the nitrogen atom shown in ring B; and ring B is substituted with 0-4 $R^2$;

$R^1$ is independently

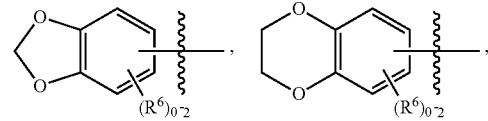

phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-4}$ alkyl substituted with 0-1 $R^{12}$, $C_{1-4}$ alkoxy substituted with 0-1 $R^{12}$, $C_{1-4}$ haloalkyl, $C_{1-4}$ haloalkoxy, and benzyl;

when two $R^2$ groups are attached to two different carbon atoms, they may combine to form a 1- to 3-membered carbon atom bridge over ring B;

when two $R^2$ groups are attached to the same carbon, they may combine, together with the carbon atom to which they are attached, to form a 3- to 6-membered carbon atom containing spiro ring;

$R^3$ is independently selected from: $C_{1-4}$ alkyl substituted with $R^{10}$, $C_{1-4}$ alkoxy substituted with $R^{10}$, $C_{1-4}$ haloalkyl substituted with $R^{10}$, $C_{1-4}$ haloalkoxy substituted with $R^{10}$, $OR^9$, and $-O(CH_2)_{1-2}O(CH_2)_{1-4}R^{10}$;

$R^{4a}$ is independently selected from: H, halogen, $C_{1-4}$ alkyl, $C_{1-4}$ alkoxy, and $-(CH_2)_m-C_{3-6}$ carbocycle;

$R^5$, at each occurrence, is independently selected from: halogen, $C_{1-6}$ alkyl, $C_{1-6}$ haloalkyl, $C_{1-6}$ alkoxy, and $C_{1-6}$ haloalkoxy;

$R^6$, at each occurrence, is independently selected from: halogen, OH, $C_{1-4}$ alkylthio, CN, $SO_2(C_{1-2}$ alkyl), $N(C_{1-4}$ alkyl)$_2$, $C_{1-4}$ haloalkyl, $C_{1-4}$ haloalkoxy, $C_{1-8}$ alkyl substituted with 0-1 $R^7$, $C_{1-4}$ alkoxy substituted with 0-1 $R^7$, $-(O)_n-(CH_2)_m-(C_{3-6}$ carbocycle substituted with 0-2 $R^7$), $-(CH_2)_m$-(naphthyl substituted with 0-2 $R^7$), and $-(CH_2)_m$-(5- to 10-membered heteroaryl containing carbon atoms and 1-4 heteroatoms selected from N, O, and S; wherein said heteroaryl is substituted with 0-2 $R^7$);

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl)$_2$, $SO_2(C_{1-2}$ alkyl), and phenyl;

$R^9$, at each occurrence, is independently selected from: $C_{1-6}$ alkyl substituted with substituted with $R^{10}$, and $C_{1-4}$ haloalkyl substituted with $R^{10}$;

$R^{10}$, at each occurrence, is independently selected from: CN, $C_{1-4}$ alkoxy, $C_{1-4}$ haloalkoxy, $CO_2(C_{1-4}$ alkyl), $SO_2(C_{1-4}$ alkyl), and tetrazolyl;

$R^{11}$, at each occurrence, is independently selected from: H, $C_{1-4}$ alkyl and benzyl;

$R^{12}$, at each occurrence, is independently selected from: halogen, CN, $C_{1-4}$ alkyl, $C_{1-4}$ alkoxy, $C_{1-4}$ haloalkyl, $C_{1-4}$ haloalkoxy, $CO_2(C_{1-4}$ alkyl), and tetrazolyl;

m, at each occurrence, is independently 0, 1, or 2; and n, at each occurrence, is independently 0 or 1.

In a third aspect, the present disclosure includes a compound of Formula (I) or (II), or a stereoisomer, a tautomer, a pharmaceutically acceptable salt, a polymorph, or a solvate thereof, within the scope of the first or second aspect, wherein ring A is independently

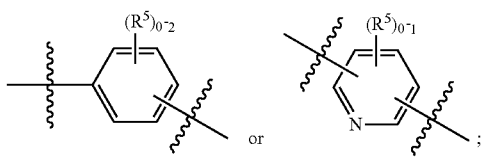

or ring B is independently selected from:

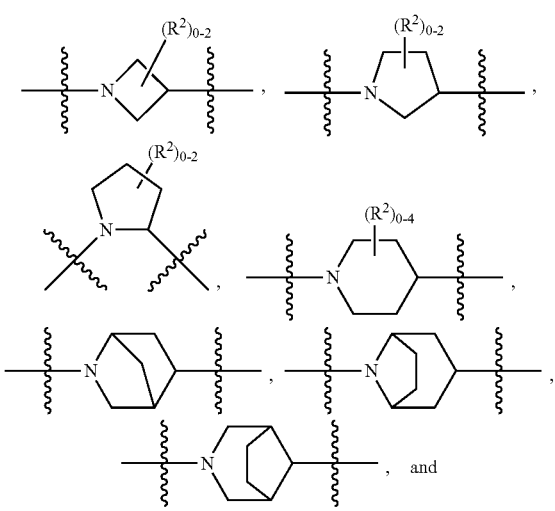

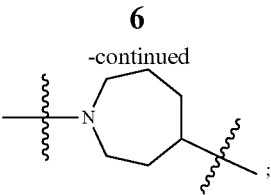

$R^1$ is independently

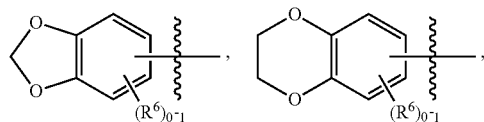

phenyl substituted with 0-3 $R^6$ or a heteroaryl substituted with 0-2 $R^6$; wherein said heteroaryl is selected from: furanyl, oxazolyl, thiazolyl, pyrazolyl, oxadiazolyl, pyridinyl, pyrimidinyl, pyrazinyl,

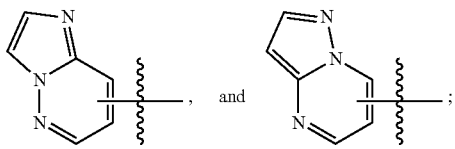

$R^2$, at each occurrence, is independently selected from: OH, halogen, $C_{1-4}$ alkyl substituted with 0-1 $R^{12}$, $C_{1-4}$ alkoxy substituted with 0-1 $R^{12}$, and benzyl;

$R^3$ is independently selected from: $C_{1-4}$ alkyl substituted with 1 $R^{10}$, $C_{1-4}$ alkoxy substituted with 1 $R^{10}$, $C_{1-4}$ haloalkyl substituted with 1 $R^{10}$, $OR^9$ and $C_{1-4}$ haloalkoxy substituted with 1 $R^{10}$;

$R^{4a}$ is independently selected from: H, halogen $C_{1-4}$ alkyl, $C_{1-4}$ alkoxy, and $C_{3-6}$ cycloalkyl;

$R^6$, at each occurrence, is independently selected from: halogen, OH, $C_{1-6}$ alkyl substituted with 0-1 OH, $C_{1-4}$ alkoxy, $C_{1-4}$ alkylthio, $C_{1-4}$ haloalkyl, $C_{1-4}$ haloalkoxy, CN, $SO_2(C_{1-2}$ alkyl), $N(C_{1-4}$ alkyl)$_2$, $C_{3-6}$ cycloalkyl substituted with 0-2 $C_{1-4}$ alkyl, $C_{5-6}$ cycloalkenyl substituted with 0-2 $C_{1-4}$ alkyl, $-O-C_{3-6}$ cycloalkyl, benzyl, and oxazolyl;

$R^9$, at each occurrence, is independently selected from: $C_{1-6}$ alkyl substituted with substituted with $R^{10}$, and $C_{1-4}$ haloalkyl substituted with $R^{10}$;

$R^{10}$, at each occurrence, is independently selected from: CN, $C_{1-4}$ alkoxy, $C_{1-4}$ haloalkoxy, $CO_2(C_{1-4}$ alkyl), $SO_2(C_{1-4}$ alkyl), and tetrazolyl; and $R^{12}$, at each occurrence, is independently selected from: halogen, CN, $C_{1-4}$ alkyl, $C_{1-4}$ alkoxy, $C_{1-4}$ haloalkyl, $C_{1-4}$ haloalkoxy, $CO_2(C_{1-2}$ alkyl), and tetrazolyl.

In a fourth aspect, the present invention includes a compound of Formula (I) or (II), or a stereoisomer, a tautomer, a pharmaceutically acceptable salt, a polymorph, or a solvate thereof, within the scope of the first, second or third aspect, wherein $R^1$ is independently

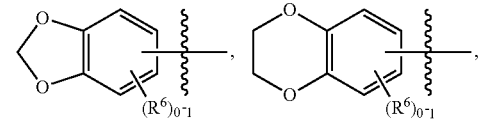

phenyl substituted with 0-3 R⁶, or a heteroaryl substituted with 0-2 R⁶; wherein said heteroaryl is selected from: thiazolyl, pyridinyl, pyrimidinyl, pyrazinyl,

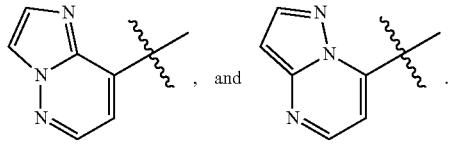 [SMILES: *c1ccnn2ccnc12 ; *c1ccnc2ccnn12]

In a fifth aspect, the present disclosure includes a compound of Formula (I) or (II), or a stereoisomer, a tautomer, a pharmaceutically acceptable salt, a polymorph, or a solvate thereof, within the scope of any of the above aspect, wherein ring B is independently selected from:

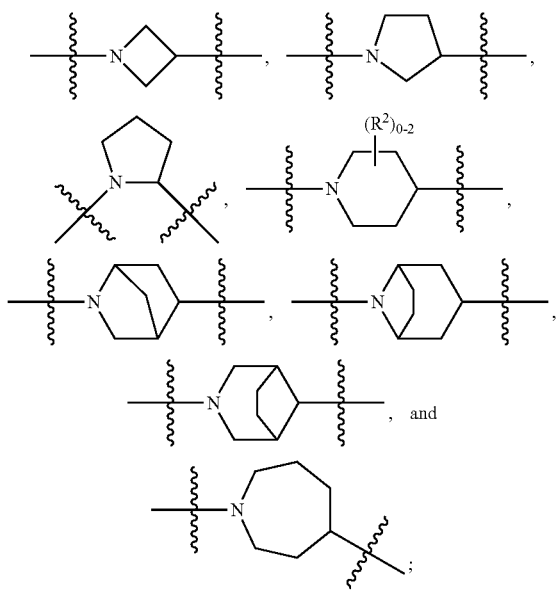

$R^1$ is independently phenyl substituted with 0-3 $R^6$, pyridinyl substituted with 0-2 $R^6$, pyrazinyl substituted with 0-2 $R^6$, pyrimidinyl substituted with 0-2 $R^6$, thiazolyl substituted with 0-2 $R^6$,

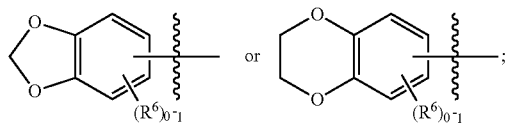

and $R^2$, at each occurrence, is independently selected from: OH, halogen, $C_{1-4}$ alkyl substituted with 0-1 CN, $C_{1-4}$ alkoxy, benzyl, and tetrazolylmethyl.

In a sixth aspect, the present disclosure includes a compound of Formula (I) or (II), or a stereoisomer, a tautomer, a pharmaceutically acceptable salt, a polymorph, or a solvate thereof, within the scope of any of the above aspect, wherein ring B is independently selected from:

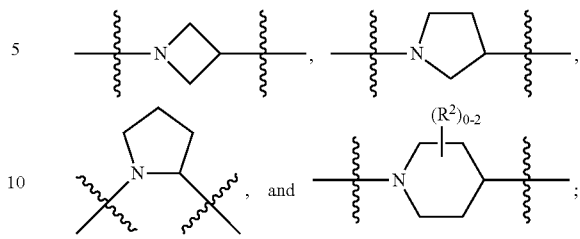

$R^1$, at each occurrence, is independently phenyl substituted with 0-3 $R^6$ or pyridinyl substituted with 0-2 $R^6$;

$R^2$, at each occurrence, is independently selected from: halogen, $C_{1-4}$ alkyl, $C_{1-4}$ alkoxy and tetrazolylmethyl;

$R^3$, at each occurrence, is independently selected from: $C_{1-4}$ alkyl substituted with $R^{10}$, $C_{1-4}$ alkoxy substituted with $R^{10}$, $OR^9$ and $-O(CH_2)_{1-2}O(CH_2)_{1-4}R^{10}$; and $R^6$, at each occurrence, is independently selected from: halogen, $C_{1-6}$ alkyl, $C_{1-4}$ alkoxy, $C_{1-4}$ haloalkyl, $C_{1-4}$ haloalkoxy, $C_{3-6}$ cycloalkyl substituted with 0-2 $C_{1-4}$ alkyl, $C_{5-6}$ cycloalkenyl substituted with 0-2 $C_{1-4}$ alkyl, and benzyl;

$R^9$, at each occurrence, is independently selected from: $C_{1-6}$ alkyl substituted with substituted with $R^{10}$, and $C_{1-4}$ haloalkyl substituted with $R^{10}$; and $R^{10}$, at each occurrence, is independently selected from: CN, $C_{1-4}$ alkoxy, $C_{1-4}$ haloalkoxy, $CO_2(C_{1-4}$ alkyl), $SO_2(C_{1-4}$ alkyl), and tetrazolyl.

In a seventh aspect, the present disclosure includes a compound of Formula (III), (IIIa), (IIIb) or (IIIc):

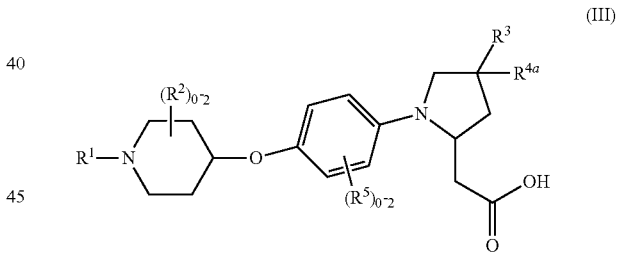

(III)

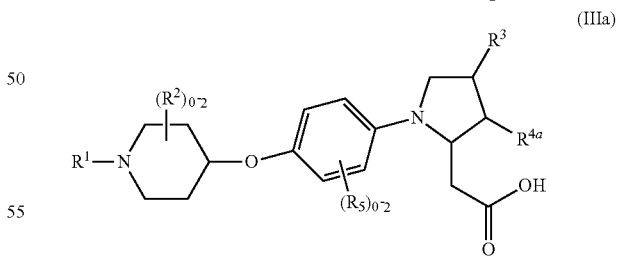

(IIIa)

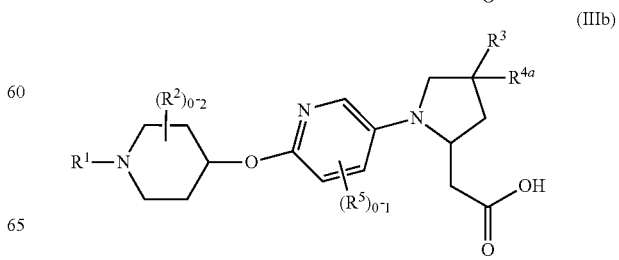

(IIIb)

-continued

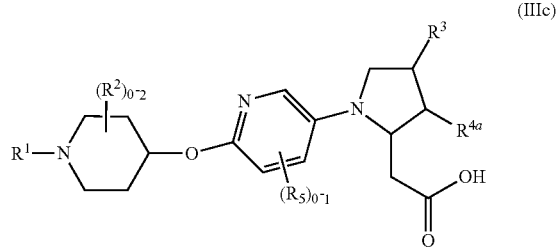
(IIIc)

or a stereoisomer, a tautomer, a pharmaceutically acceptable salt, a polymorph, or a solvate thereof, wherein $R^1$, at each occurrence, is independently phenyl substituted with 0-3 $R^6$ or pyridinyl substituted with 0-2 $R^6$;

$R^2$, at each occurrence, is independently selected from: halogen, $C_{1-4}$ alkyl, and $C_{1-4}$ alkoxy;

$R^3$, at each occurrence, is independently selected from: $C_{1-4}$ alkyl substituted with $C_{1-4}$ alkoxy, and $C_{1-4}$ alkoxy substituted with $C_{1-4}$ alkoxy;

$R^{4a}$, at each occurrence, is independently selected from: H, halogen, $C_{1-4}$ alkyl, $C_{1-4}$ alkoxy, and cyclopropyl;

$R^5$, at each occurrence, is independently selected from: halogen, $C_{1-4}$ haloalkyl, and $C_{1-6}$ alkoxy; and $R^6$, at each occurrence, is independently selected from: halogen, $C_{1-6}$ alkyl, $C_{1-4}$ alkoxy, $C_{3-6}$ cycloalkyl substituted with 0-2 $C_{1-4}$ alkyl, and $C_{5-6}$ cycloalkenyl substituted with 0-2 $C_{1-4}$ alkyl.

In an eighth aspect, the present disclosure includes a compound of Formula (I) (II), (III), (IIIa), (IIIb) or (IIIc), or a stereoisomer, a tautomer, a pharmaceutically acceptable salt, a polymorph, or a solvate thereof, within the scope of any of the above aspect, wherein $R^1$, at each occurrence, is independently phenyl substituted with 0-3 $R^6$ or pyridinyl substituted with 0-2 $R^6$;

$R^2$, at each occurrence, is independently selected from: halogen and $C_{1-2}$ alkyl;

$R^3$, at each occurrence, is independently selected from: $C_{1-4}$ alkyl substituted with $C_{1-4}$ alkoxy, and $C_{1-4}$ alkoxy substituted with $C_{1-4}$ alkoxy;

$R^{4a}$, at each occurrence, is independently selected from: H and methyl;

$R^5$, at each occurrence, is independently selected from: halogen, $C_{1-4}$ haloalkyl, and $C_{1-6}$ alkoxy; and $R^6$, at each occurrence, is independently selected from: halogen, $C_{1-6}$ alkyl, and $C_{1-4}$ alkoxy.

In a ninth aspect, the present disclosure includes a compound selected from the exemplified examples or a stereoisomer, a tautomer, a pharmaceutically acceptable salt, a polymorph, or a solvate thereof.

In another aspect, the present disclosure includes a compound selected from any subset list of compounds or a single compound from the exemplified examples within the scope of any of the above aspects.

In another embodiment, the compounds of the present invention have hGPR40 $EC_{50}$ values ≤5 µM.

In another embodiment, the compounds of the present invention have hGPR40 $EC_{50}$ values ≤1 µM.

In another embodiment, the compounds of the present invention have hGPR40 $EC_{50}$ values ≤0.5 µM.

In another embodiment, the compounds of the present invention have hGPR40 $EC_{50}$ values ≤0.2 µM.

In another embodiment, the compounds of the present invention have hGPR40 $EC_{50}$ values ≤0.1 µM.

II. Other Embodiments of the Invention

In another embodiment, the present invention provides a composition comprising at least one of the compounds of the present invention or a stereoisomer, a tautomer, a pharmaceutically acceptable salt, a polymorph, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, a polymorph, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, a polymorph, or a solvate thereof.

In another embodiment, the present invention provides a process for making a compound of the present invention or a stereoisomer, a tautomer, a pharmaceutically acceptable salt, a polymorph, or a solvate thereof.

In another embodiment, the present invention provides an intermediate for making a compound of the present invention or a stereoisomer, a tautomer, a pharmaceutically acceptable salt, a polymorph, or a solvate thereof.

In another embodiment, the present invention provides a pharmaceutical composition further comprising additional therapeutic agent(s). Examples of additional therapeutic agent(s), according to the present invention include, but are not limited to, anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, and appetite suppressants.

In a preferred embodiment, the present invention provides pharmaceutical composition, wherein the additional therapeutic agents are, for example, a DPP4 inhibitor (for example a member selected from saxagliptin, sitagliptin, vildagliptin, linagliptin, and alogliptin).

In a preferred embodiment, the present invention provides pharmaceutical composition, wherein the additional therapeutic agents are, for example, an SGLT2 inhibitor (for example a member selected from dapagliflozin, canagliflozin, empagliflozin and remagliflozin).

In another embodiment, the present invention provides a method for the treatment of multiple diseases or disorders associated with GPR40, comprising administering to a patient in need of such treatment a therapeutically effective amount of at least one of the compounds of the present invention, alone, or, optionally, in combination with another compound of the present invention and/or at least one other type of therapeutic agent.

Examples of diseases or disorders associated with the activity of the GPR40 that can be prevented, modulated, or treated according to the present invention include, but are not limited to, diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), non-cardiac ischemia, pancreatitis, lipid disorders, and liver diseases such as NASH (Non-Alcoholic SteatoHepatitis), NAFLD (Non-Alcoholic Fatty Liver Disease), liver cirrhosis, inflammatory bowel diseases incorporating ulcerative colitis and Crohn's disease, celiac disease, osteoarthritis, nephritis, psoriasis, atopic dermatitis, and skin inflammation.

In another embodiment, the present invention provides a method for the treatment of diabetes, hyperglycemia, gestational diabetes, obesity, dyslipidemia, hypertension and cognitive impairment, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of diabetes, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of hyperglycemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of obesity, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of dyslipidemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of hypertension, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of cognitive impairment, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of multiple diseases or disorders associated with GPR40.

In another embodiment, the present invention also provides the use of a compound of the present invention for the manufacture of a medicament for the treatment of multiple diseases or disorders associated with GPR40.

In another embodiment, the present invention provides a method for the treatment of multiple diseases or disorders associated with GPR40, comprising administering to a patient in need thereof a therapeutically effective amount of a first and second therapeutic agent, wherein the first therapeutic agent is a compound of the present invention. Preferably, the second therapeutic agent, for example, a DPP4 inhibitor (for example a member selected from saxagliptin, sitagliptin, vildagliptin, linagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of multiple diseases or disorders associated with GPR40.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR40 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the GPR40 receptor modulator of the present invention include, but are not limited to, insulin secretagogues or insulin sensitizers, other GPR40 receptor modulators, or other antidiabetic agents. These agents include, but are not limited to, DPP4 inhibitors (for example, sitagliptin, saxagliptin, alogliptin, linagliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, tesaglitazar and aleglitazar), glucokinase activators, GPR119 receptor modulators (for example, MBX-2952, PSN821, and APD597), GPR120 receptor modulators (for example, as described in Shimpukade, B. et al., *J. Med. Chem.*, 55(9):4511-4515 (2012)), SGLT2 inhibitors (for example, dapagliflozin, canagliflozin, empagliflozin and remagliflozin), MGAT inhibitors (for example, as described in Barlind, J. G. et al., *Bioorg. Med. Chem. Lett.*, 23(9): 2721-2726 (2013)), amylin analogs such as pramlintide, and/or insulin.

The GPR40 receptor modulator of the present invention may also be optionally employed in combination with agents for treating complication of diabetes. These agents include PKC inhibitors and/or AGE inhibitors.

The GPR40 receptor modulator of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The GPR40 receptor modulator of the present invention may also be employed in combination with an agonist of the glucagon-like peptide-1 receptor (GLP-1 R), such as exenatide, liraglutide, GLP-1 (1-36) amide, GLP-1(7-36) amide, GLP-1(7-37), which may be administered via injection, intranasal, or by transdermal or buccal devices.

Additional embodiments provide compounds having the structures:

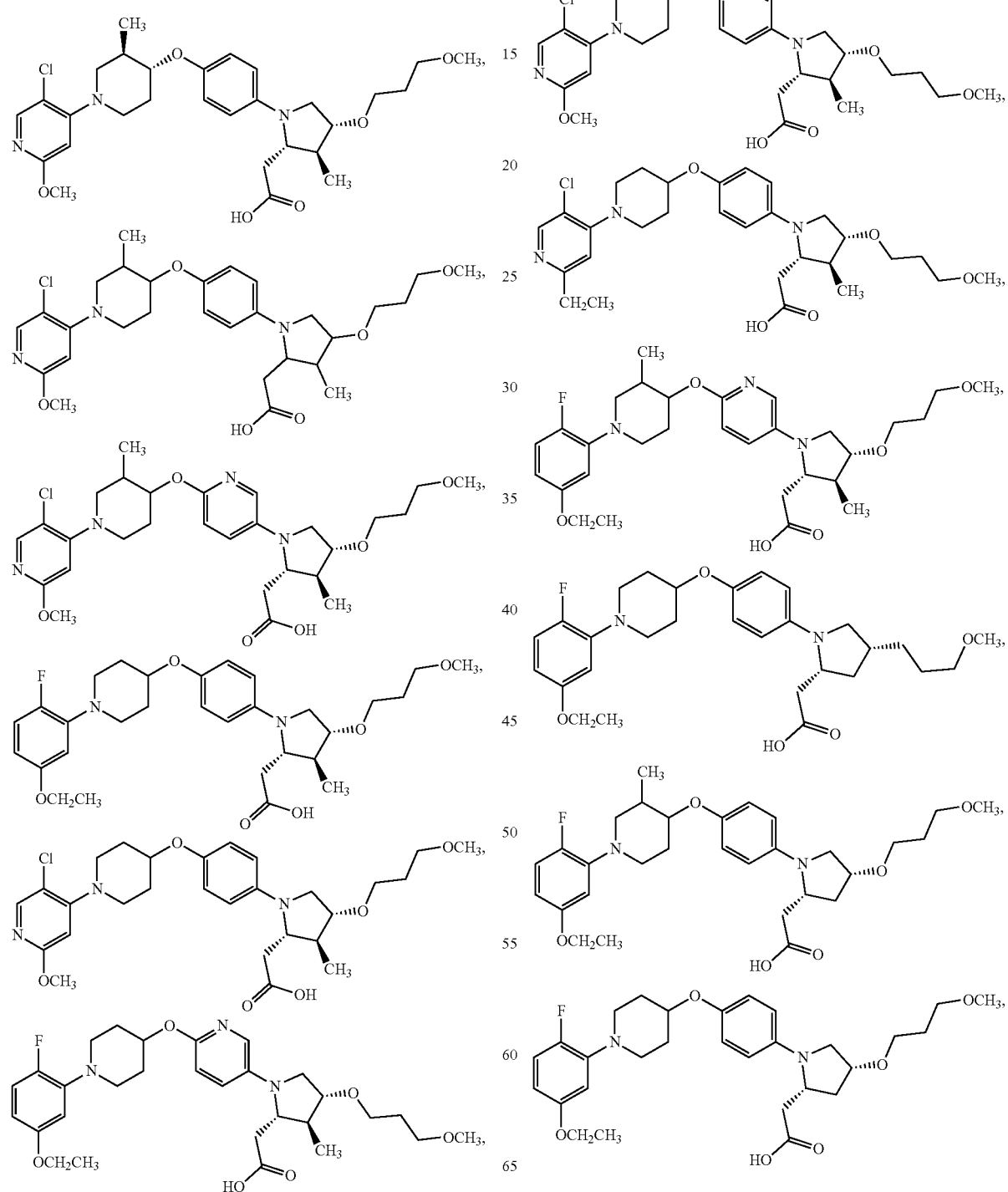

15
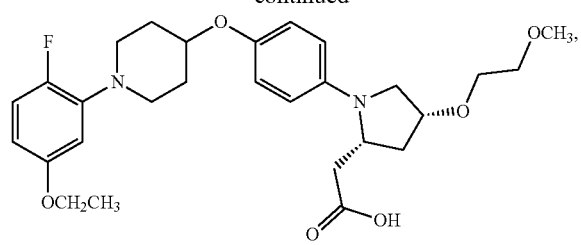
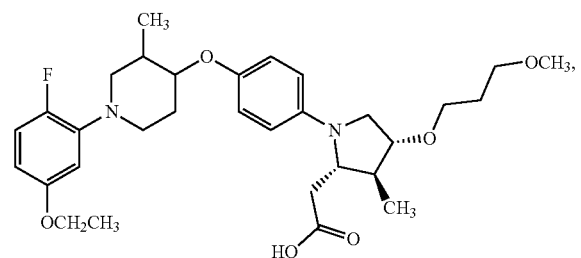
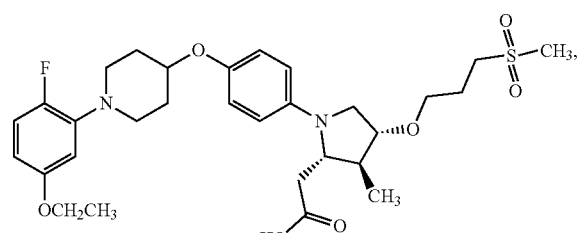
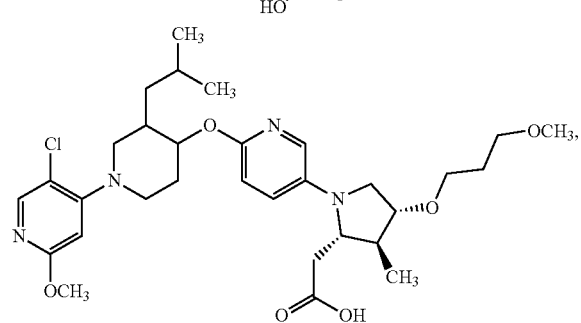
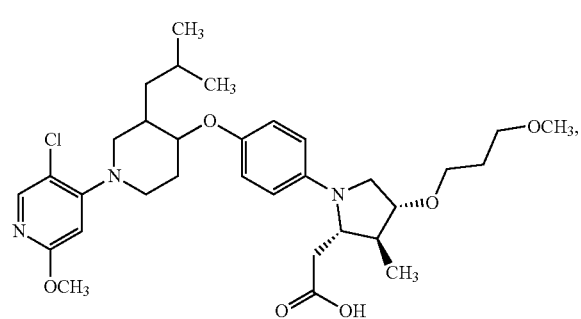
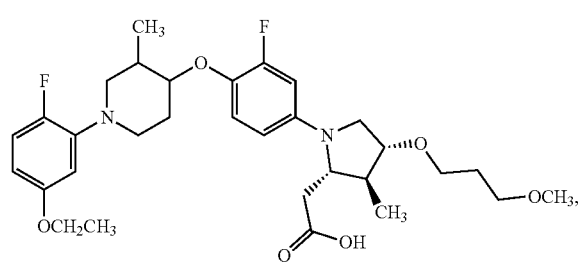
16
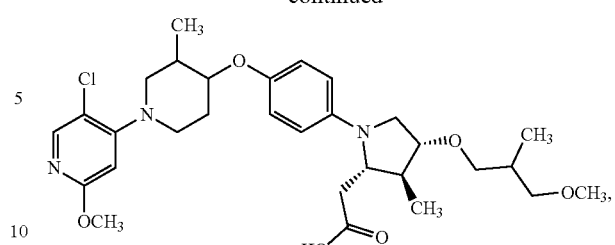
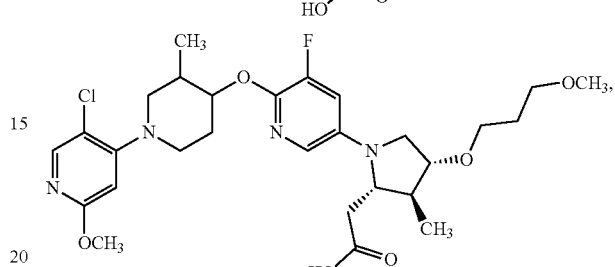
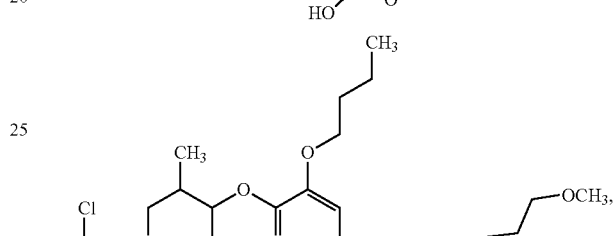
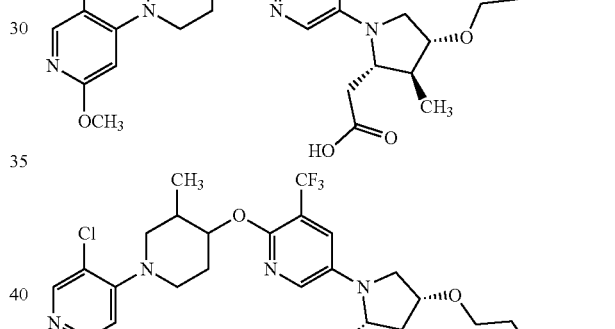
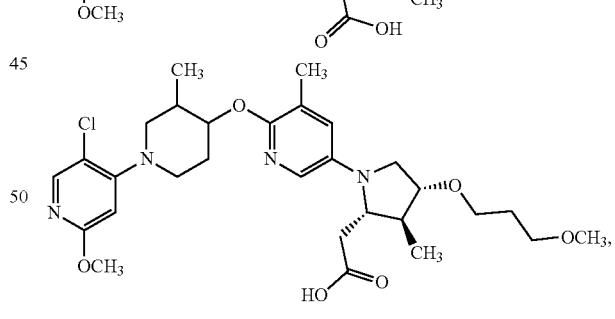
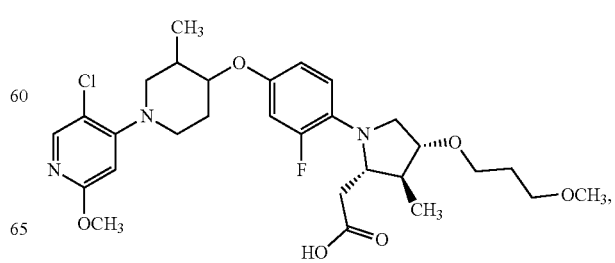

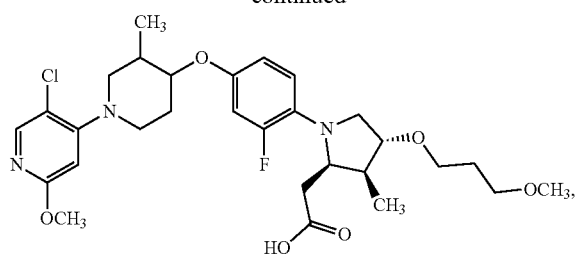

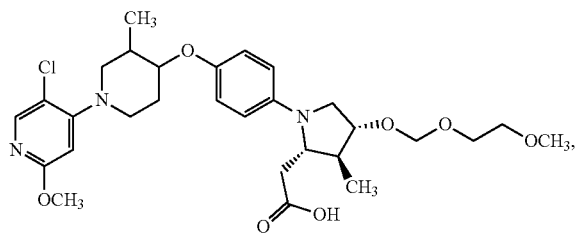

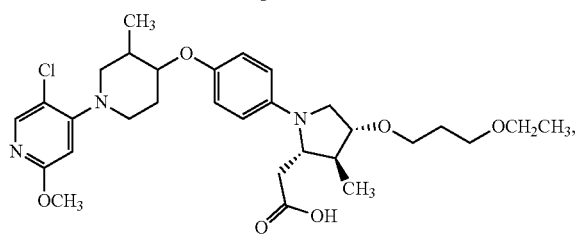

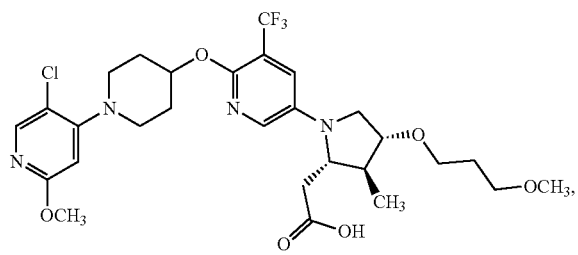

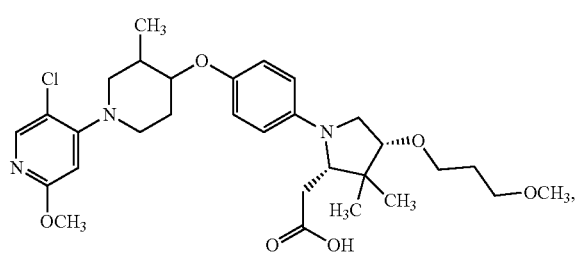

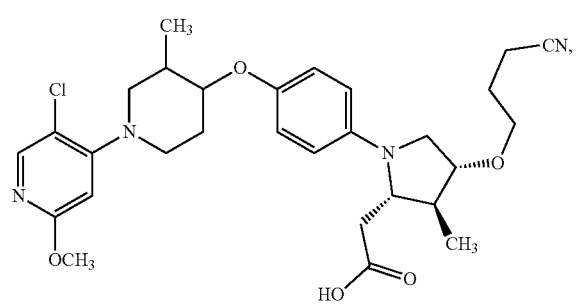

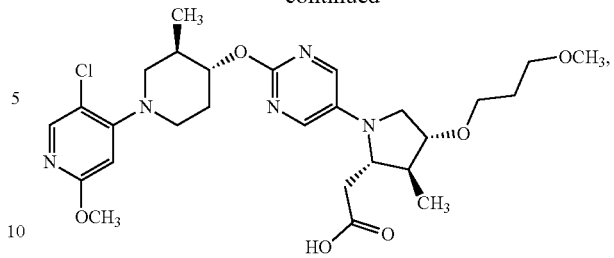

or a stereoisomer, a tautomer, a pharmaceutically acceptable salt, a polymorph, or a solvate thereof.

Another embodiment of the present invention includes the compound having the structure:

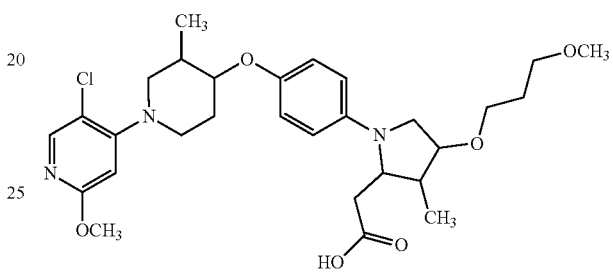

or a stereoisomer, a tautomer, a pharmaceutically acceptable salt, a polymorph, or a solvate thereof.

Another embodiment of the present invention includes the compound having the structure:

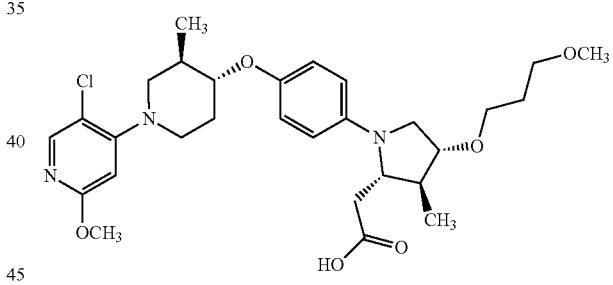

or a stereoisomer, a tautomer, a pharmaceutically acceptable salt, a polymorph, or a solvate thereof.

Another embodiment of the present invention includes the compound having the structure:

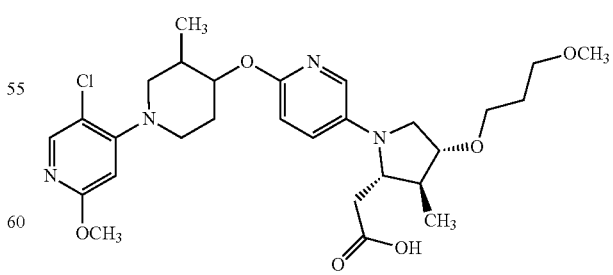

or a stereoisomer, a tautomer, a pharmaceutically acceptable salt, a polymorph, or a solvate thereof.

Another embodiment of the present invention includes the compound having the structure:

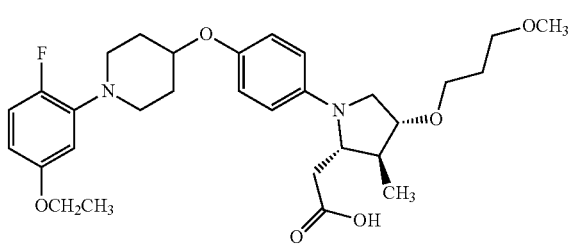 [SMILES: CCOc1ccc(F)c(N2CCC(Oc3ccc(N4C[C@H](OCCCOC)[C@@H](C)[C@@H]4CC(=O)O)cc3)CC2)c1]

or a stereoisomer, a tautomer, a pharmaceutically acceptable salt, a polymorph, or a solvate thereof.

Another embodiment of the present invention includes the compound having the structure:

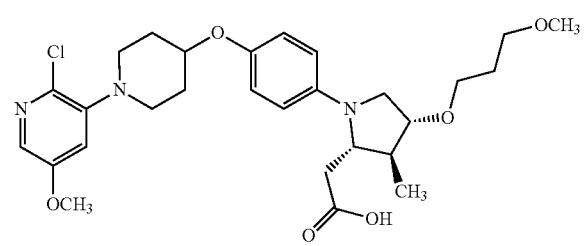 [SMILES: COCCCO[C@H]1CN(c2ccc(OC3CCN(c4cc(OC)cnc4Cl)CC3)cc2)[C@@H](CC(=O)O)[C@@H]1C]

or a stereoisomer, a tautomer, a pharmaceutically acceptable salt, a polymorph, or a solvate thereof.

Another embodiment of the present invention includes the compound having the structure:

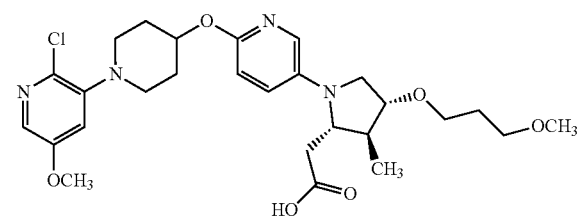 [SMILES: COCCCO[C@H]1CN(c2ccc(OC3CCN(c4cc(OC)cnc4Cl)CC3)nc2)[C@@H](CC(=O)O)[C@@H]1C]

or a stereoisomer, a tautomer, a pharmaceutically acceptable salt, a polymorph, or a solvate thereof.

Another embodiment of the present invention includes the compound having the structure:

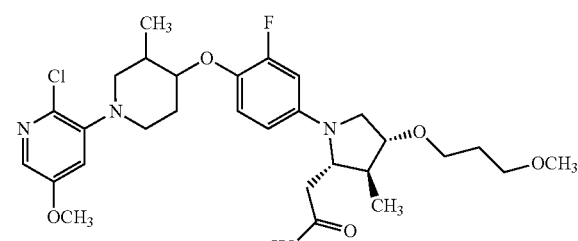

or a stereoisomer, a tautomer, a pharmaceutically acceptable salt, a polymorph, or a solvate thereof.

Another embodiment of the present invention includes the compound having the structure:

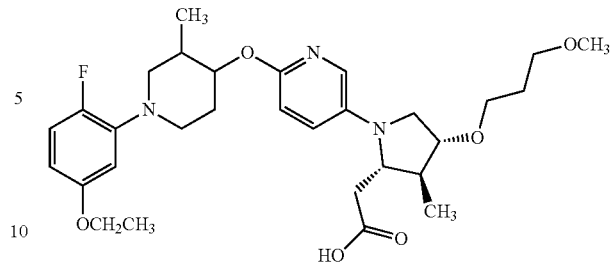

or a stereoisomer, a tautomer, a pharmaceutically acceptable salt, a polymorph, or a solvate thereof.

Another embodiment of the present invention includes the compound having the structure:

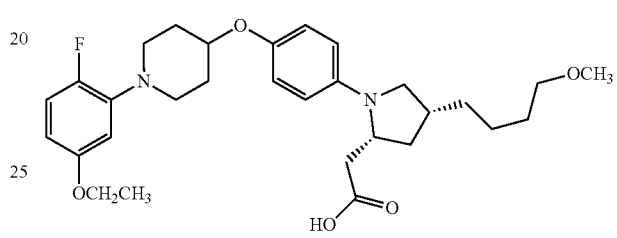

or a stereoisomer, a tautomer, a pharmaceutically acceptable salt, a polymorph, or a solvate thereof.

Another embodiment of the present invention includes the compound having the structure:

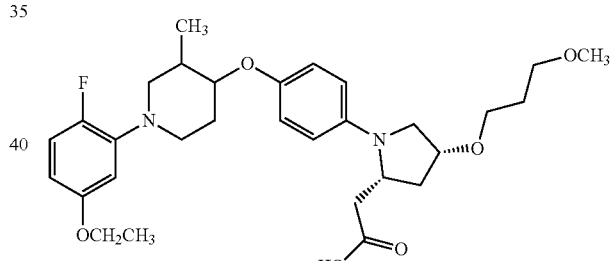

or a stereoisomer, a tautomer, a pharmaceutically acceptable salt, a polymorph, or a solvate thereof.

Another embodiment of the present invention includes the compound having the structure:

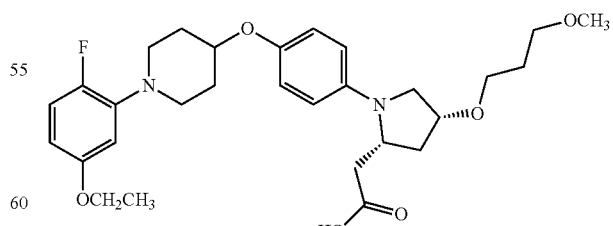

or a stereoisomer, a tautomer, a pharmaceutically acceptable salt, a polymorph, or a solvate thereof.

Another embodiment of the present invention includes the compound having the structure:

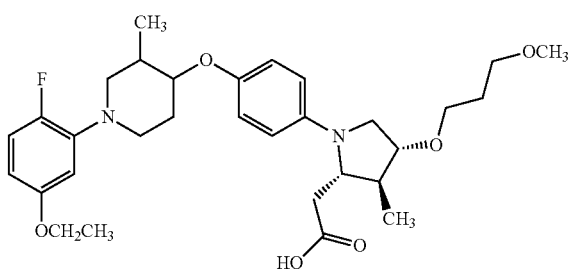 [SMILES: CCOc1ccc(F)c(N2CCC(Oc3ccc(N4C[C@H](OCCCOC)[C@@H](C)[C@@H]4CC(=O)O)cc3)C(C)C2)c1]

or a stereoisomer, a tautomer, a pharmaceutically acceptable salt, a polymorph, or a solvate thereof.

Another embodiment of the present invention includes the compound having the structure:

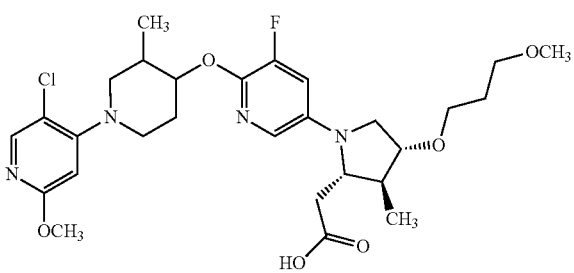 [SMILES: COCCCO[C@H]1CN(c2cnc(OC3CCN(c4cc(OC)ncc4Cl)CC3C)c(F)c2)[C@@H](CC(=O)O)[C@@H]1C]

or a stereoisomer, a tautomer, a pharmaceutically acceptable salt, a polymorph, or a solvate thereof.

Another embodiment of the present invention includes the compound having the structure:

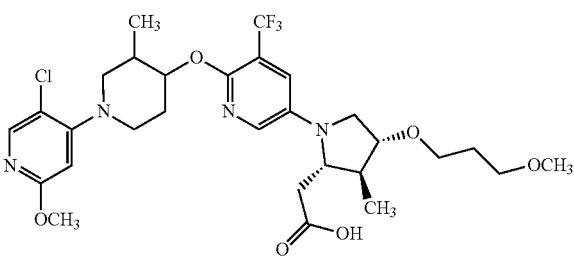 [SMILES: COCCCO[C@H]1CN(c2cnc(OC3CCN(c4cc(OC)ncc4Cl)CC3C)c(C(F)(F)F)c2)[C@@H](CC(=O)O)[C@@H]1C]

or a stereoisomer, a tautomer, a pharmaceutically acceptable salt, a polymorph, or a solvate thereof.

Another embodiment of the present invention includes the compound having the structure:

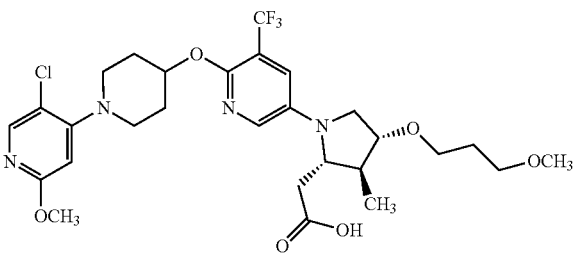 [SMILES: COCCCO[C@H]1CN(c2cnc(OC3CCN(c4cc(OC)ncc4Cl)CC3)c(C(F)(F)F)c2)[C@@H](CC(=O)O)[C@@H]1C]

or a stereoisomer, a tautomer, a pharmaceutically acceptable salt, a polymorph, or a solvate thereof.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment.

Furthermore, any element of an embodiment is meant to be combined with any and all other elements from any embodiment to describe an additional embodiment.

III. Chemistry

Throughout the specification, examples and the appended claims, a given chemical formula or name shall encompass all stereo and optical isomers and racemates thereof where such isomers exist. The term "stereoisomer(s)" refers to compound(s) which have identical chemical constitution, but differ with regard to the arrangement of the atoms or groups in space. Unless otherwise indicated, all chiral (enantiomeric and diastereomeric) and racemic forms are within the scope of the invention. The term "chiral" refers to molecules which have the property of non-superimposability of the mirror image partner, while the term "achiral" refers to molecules which are superimposable on their mirror image partner. The terms "racemic mixture" and "racemate" refer to an equimolar mixture of two enantiomeric species, devoid of optical activity.

Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms.

The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Unless otherwise indicated, any heteroatom with unsatisfied valences is assumed to have hydrogen atoms sufficient to satisfy the valences.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl"

denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and butoxy (e.g., n-butoxy, isobutoxy and t-butoxy). Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, imidazopyridazinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolopyrimidinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, pyrimidinyl, pyrazolyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, imidazolopyridinyl, imidazopyridazinyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, pyrazolopyridinyl and pyrazolopyrimidinyl.

Examples of 5- to 6-membered heterocycles include, but are not limited to, pyridinyl, furanyl, thienyl, pyrrolyl, pyrazolyl, pyrazinyl, piperazinyl, piperidinyl, pyrimidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), calcium ($Ca^{2+}$)ammonium ($R_nNH_m$+ where n=0-4 and m=0-4) and the like.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis*, Fourth Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of the present invention can form salts which are also within the scope of this invention. Unless otherwise indicated, reference to an inventive compound is understood to include reference to one or more salts thereof. Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of Formula (I)) is a prodrug within the scope and spirit of the invention. Various forms of prodrugs are well known in the art. For examples of such prodrug derivatives, see a) Bundgaard, H., ed., *Design of Prodrugs*, Elsevier (1985);

b) Widder, K. et al., eds., *Methods in Enzymology*, 112: 309-396, Academic Press (1985);

c) Bundgaard, H., Chapter 5, "Design and Application of Prodrugs", *A Textbook of Drug Design and Development*, pp. 113-191, Krosgaard-Larsen, P. et al., eds., Harwood Academic Publishers, publ. (1991);

d) Bundgaard, H., *Adv. Drug Deliv. Rev.*, 8:1-38 (1992);

e) Nielsen, N. M. et al., *J. Pharm. Sci.*, 77:285 (1988);

f) Kakeya, N. et al., *Chem. Pharm. Bull.*, 32:692 (1984); and g) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield Formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ (also represented as 'D' for deuterium) and $^3H$, carbon such as $^{11}C$, $^{13}C$, and $^{14}C$, nitrogen, such as $^{13}N$ and $^{15}N$, oxygen, such as $^{15}O$, $^{17}O$, and $^{18}O$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increase in vivo half-life or reduced dosage requirements, and hence may be preferred in some circumstances. Substitution with positron emitting isotopes, such as $^{11}C$, $^{15}O$, and $^{13}N$, can be useful in Positron Emission Topography (PET) studies for examining substrate receptor occupancy. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form (s) having the same chemical structure/composition but different spatial arrangements of the molecules and/or ions forming the crystals. Compounds of the present invention can be provided as amorphous solids or crystalline solids. Lyophilization can be employed to provide the compounds of the present invention as a solid.

Abbreviations as used herein, are defined as follows: "1×" for once, "2×" for twice, "3×" for thrice, "A" for "Angstroms", "° C." for degrees Celsius, "eq" for equivalent or equivalents, "g" for gram or grams, "mg" for milligram or milligrams, "L" for liter or liters, "mL or ml" for milliliter or milliliters, "L" for microliter or microliters, "N" for normal, "M" for molar, "N" for normal, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "RP-Prep. HPLC" for reverse phase preparative HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

AcCl acetyl chloride
$Ac_2O$ acetic anhydride
AcOH acetic acid
ADDP 1,1'-(azodicarbonyl)dipiperidine
$Ag_2O$ silver oxide
$AlMe_3$ trimethylaluminum
atm atmosphere
9-BBN 9-borabicyclo[3.3.1]nonane
$BF_3.OEt_2$ boron trifluoride diethyl etherate
$BF_3.SMe_2$ boron trifluoride dimethyl sulfide
$BH_3.DMS$ borane dimethyl sulfide complex
Bn benzyl
Boc tert-butyloxycarbonyl
$Boc_2O$ di-tert-butyl dicarbonate
Bu butyl
$Bu_2BOTf$ dibutylboron trifluoromethanesulfonate
n-BuOH n-butanol
$Bu_3P$ tributylphosphine
$CBr_4$ carbon tetrachloride
$CDCl_3$ deutero-chloroform
$CD_2Cl_2$ deutero-dichloromethane
cDNA complimentary DNA
$CH_2Cl_2$ or DCM dichloromethane
$CH_3CN$ or MeCN acetonitrile
$CHCl_3$ chloroform
$CO_2$ carbon dioxide
CSA camphorsulfonic acid
$Cs_2CO_3$ cesium carbonate
$Cu(OAc)_2$ copper(II) acetate
CuI copper(I) iodide
$CuBr.SMe_2$ copper(I) bromide dimethylsulfide complex
DAST (diethylamino)sulfur trifluoride
DBAD di-tert-butyl azodicarboxylate
DEAD diethyl azodicarboxylate
DIAD diisopropyl azodicarboxylate
DIBAL-H diisobutylaluminum hydride
DIPEA diisopropylethylamine
DMAP 4-(dimethylamino)pyridine
DMF dimethyl formamide
DMSO dimethyl sulfoxide
DtBPF 1,1'-bis(di-tert-butylphosphino)ferrocene EDTA ethylenediaminetetraacetic acid
Et ethyl
$Et_2O$ diethyl ether
EtOAc ethyl acetate
EtOCOCl ethyl chloroformate
EtOH ethanol
$H_2$ molecular Hydrogen
$H_2O_2$ hydrogen peroxide
$H_2SO_4$ sulfuric acid
HCl hydrochloric acid
Hex hexanes
i-Bu isobutyl
i-Pr isopropyl
i-PrOH or IPA isopropanol
KCN potassium cyanide
$K_2CO_3$ potassium carbonate
$K_2HPO_4$ dipotassium phosphate
$KHSO_4$ potassium bisulfate
KI potassium iodide
KOH potassium hydroxide
KOtBu potassium tert-butoxide
$K_3PO_4$ tripotassium phosphate
LAH lithium aluminum hydride
LDA lithium diisopropylamide
L.G. leaving group
LHMDS lithium hexamethyldisilazide
$LiBH_4$ lithium borohydride
LiOH lithium hydroxide
L-Selectride lithium tri-sec-butylborohydride
Me methyl
MeI iodomethane
MeLi methyl lithium
MeOH methanol
$MgSO_4$ magnesium sulfate
MSA methanesulfonic acid
MsCl methanesulfonyl chloride
MTBE methyl tert-butylether
$NaBH(OAc)_3$ sodium triacetoxyborohydride
NaDCC sodium dichloroisocyanurate
NaHMDS sodium hexamethyldisilazide
$NaNO_2$ sodium nitrite
$Na_2SO_4$ sodium sulfate
$Na_2S_2O_3$ sodium thiosulfate
$NaBH_4$ sodium borohydride
NaCl sodium chloride
NaCN sodium cyanide
NCS N-chlorosuccinimide
NaH sodium hydride
$NaHCO_3$ sodium bicarbonate
NaOH sodium hydroxide
NaOtBu sodium tert-butoxide
$NH_3$ ammonia
$NH_4Cl$ ammonium chloride
$NH_4OH$ ammonium hydroxide
$Pd(OAc)_2$ palladium(II) acetate
$Pd(OH)_2$ palladium hydroxide
Pd/C palladium on carbon
$PdCl_2(dppf)$ 1,1'-bis(diphenylphosphino)ferrocene-palladium(II)dichloride
$PdCl_2(dtbpf)$ [1,1'-bis(di-tert-butylphosphino)ferrocene]dichloropalladium(II)
$PdCl_2(PPh_3)_2$ bis(triphenylphosphine)palladium(II) dichloride
$Pd_2(dba)_3$ tris(dibenzylideneacetone)dipalladium(0)
$Pd(Ph_3P)_4$ tetrakis(triphenylphosphine)palladium(0)
P.G. protecting group
Ph phenyl
$Ph_3P$ triphenylphosphine
Pr propyl
PS polystyrene
$PtO_2$ platinum(IV) oxide
SFC supercritical fluid chromatography
$SiO_2$ silica oxide
SPhos 2-dicyclohexylphosphino-2',6'-dimethoxy-1,1'-biphenyl
SPhos precatalyst chloro(2-dicyclohexylphosphino-2',6'-dimethoxy-1,1'-biphenyl) [2-(2-aminoethylphenyl)]palladium(II)—methyl-t-butyl ether adduct
TBAF tetrabutylammonium fluoride
t-Bu tert-butyl
TBDPS-Cl tert-butylchlorodiphenylsilane
TBS-Cl tert-butyldimethylsilyl chloride
TBSOTf tert-butyldimethylsilyl trifluoromethanesulfonate
TCCA trichloroisocyanuric acid
TEA or $NEt_3$ triethylamine
TEMPO 2,2,6,6-tetramethyl-1-piperidinyloxy
TFA trifluoroacetic acid
$Tf_2O$ trifluoromethanesulfonic anhydride
THF tetrahydrofuran
$TiCl_4$ titanium tetrachloride
TMS-Cl chlorotrimethylsilane
TsCl 4-methylbenzene-1-sulfonyl chloride
TsOH orpTsOH para-toluenesulfonic acid
XPhos 2-dicyclohexylphosphino-2',4',6'-triisopropylbiphenyl The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and de-protection in the processes below may be carried out by procedures generally known in the art (see, for example, Wuts, P. G. M. et al., *Protecting Groups in Organic Syn-* thesis, Fourth Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*. Sixth Edition, Wiley & Sons, New York, N.Y. (2007); Katritzky, A. R. et al., eds., *Comprehensive Organic Functional Groups Transformations II*, Second Edition, Elsevier Science Inc., Tarrytown, N.Y. (2004); Larock, R. C., *Comprehensive Organic Transformations*, VCH Publishers, Inc., New York, N.Y. (1999), and references therein.

Methods for synthesis of a large variety of substituted pyrrolidine compounds useful as starting materials for the preparation of compounds of the present invention are well known in the art. For examples of methods useful for the preparation of pyrrolidine materials see the following references and citations therein: Katritzky et al., eds., *Comprehensive Heterocyclic Chemistry*, Pergamon Press Inc., New York (1996); Bellina, F. et al., *Tetrahedron*, 62:7213 (2006); Wolfe, J. P., *Eur. J. Org. Chem.*, 571 (2007); Deng, Q.-H. et al., *Organic Letters*, 10:1529 (2008); Pisaneschi, F. et al., *Synlett*, 18:2882 (2007); Najera, C. et al., *Angewandte Chemie, International Edition*, 44(39):6272 (2005); Sasaki, N. A., *Methods in Molecular Medicine*, 23(Peptidomimetics Protocols):489 (1999); Zhou, J.-Q. et al., *Journal of Organic Chemistry*, 57(12):3328 (1992); Coldham, I. et al., *Tetrahedron Letters*, 38(43):7621 (1997); Schlummer, B. et al., *Organic Letters*, 4(9):1471 (2002); Larock, R. C. et al., *Journal of Organic Chemistry*, 59(15):4172 (1994); Galliford, C. V. et al., *Organic Letters*, 5(19):3487 (2003); Kimura, M. et al., *Angewandte Chemie, International Edition*, 47(31):5803 (2008); Ney, J. E. et al., *Adv. Synth. Catal.*, 347:1614 (2005); Paderes, M. C. et al., *Organic Letters*, 11(9):1915 (2009); Wang, Y.-G. et al., *Organic Letters*, 11(9):2027 (2009); Cordero, F. M. et al., *Journal of Organic Chemistry*, 74(11):4225 (2009); Hoang, C. T. et al., *Journal of Organic Chemistry*, 74(11):4177 (2009). Luly, J. R. et al., *Journal of the American Chemical Society*, 105:2859 (1983); Kimball, F. S. et al., *Bioorganic and Medicinal Chemistry*, 16:4367 (2008); Bertrand, M. B. et al., *Journal of Organic Chemistry*, 73(22):8851 (2008); Browning, R. G. et al., *Tetrahedron*, 60:359 (2004); Ray, J. K. et al., *Bioorganic and Medicinal Chemistry*, 2(12): 1417 (1994); Evans, G. L. et al., *Journal of the American Chemical Society*, 72:2727 (1950); Stephens, B. E. et al., *Journal of Organic Chemistry*, 74(1):254 (2009); Spangenberg, T. et al., *Organic Letters*, 11(2):261 (2008); and Qiu, X.-L. et al., *Journal of Organic Chemistry*, 67(20):7162 (2008).

Compounds of Formula (I) may be synthesized starting with pyrrolidines A via coupling to intermediate B using, for example, CuI and NaOH to give prolinol C, as depicted in Scheme 1. Activation of intermediate C, via methanesulfonyl chloride and base, for example, and displacement with sodium cyanide leads to nitrile D. Removal of P.G. on intermediate D, such as hydrogenolysis (when P.G. is a benzyl ether), gives phenol E. $R^1$ group of intermediate J is appended via displacement of L.G. in intermediate F via amine H using S-Phos precatalyst and base, such as LiHMDS or, optionally via uncatalyzed displacement of L.G. The hydroxyl of amine J can be activated with, for example, para-toluenesulfonyl chloride and base, such as pyridine, to give tosylate K. Intermediate K and phenol E can be coupled using a base, such as $Cs_2CO_3$, to give intermediate L. The cyano or methyl ester group can be hydrolyzed via NaOH, for example, to provide compounds of Formula (I).

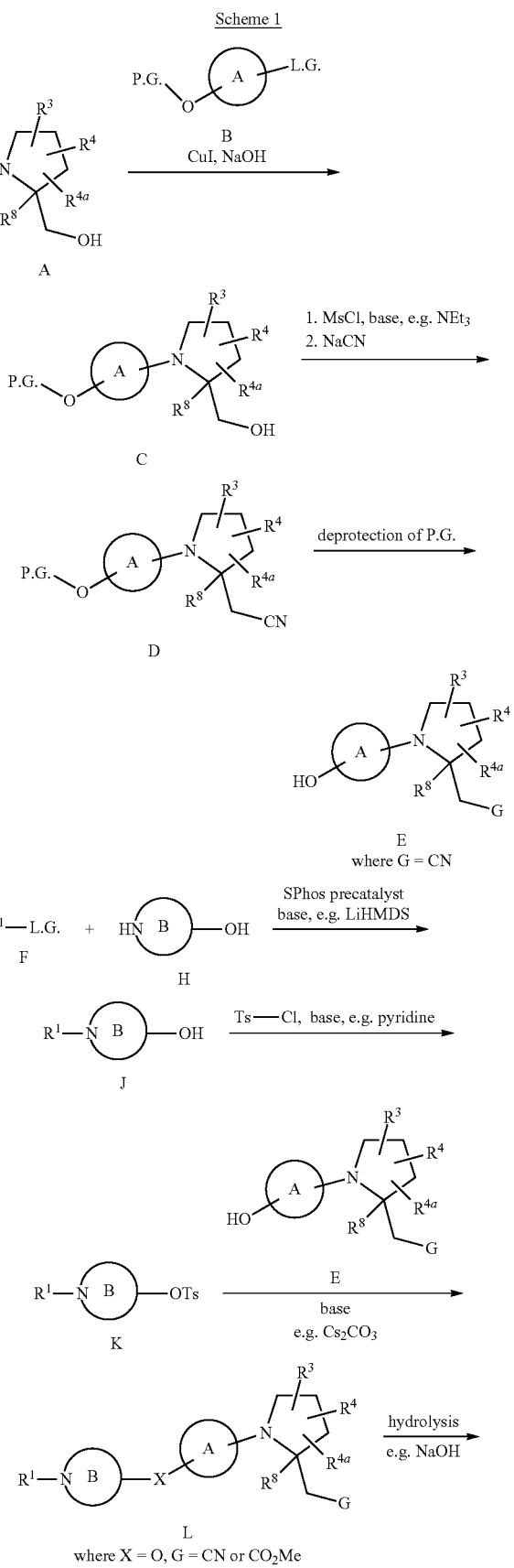

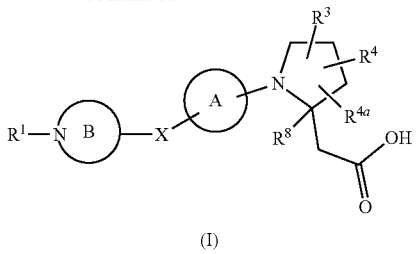

(I)

Compounds of Formula (I) can be synthesized by reaction of alcohol J with phenol E via a Mitsunobu reaction using an azodicarboxylate, such as ADDP, and a phosphine (e.g., Bu$_3$P) as demonstrated in Scheme 2 to give compound L. The intermediate L can be converted to compounds of Formula (I) by hydrolysis with base, such as NaOH.

Scheme 2

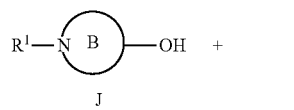

J

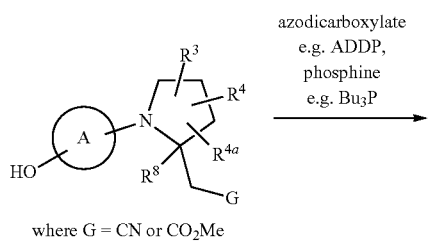

where G = CN or CO$_2$Me

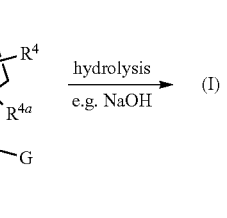

L
where X = O, G = CN or CO$_2$Me

Compounds of Formula (I) may be synthesized beginning with ketone CC, which can be reduced to alcohol H by a hydride source or dynamic kinetic resolution using glucose dehydrogenase, for example, followed by deprotection of the P.G. by hydrogenolysis (when P.G. is a benzyl group) as shown in Scheme 2.2. Displacement of a L.G., such as a chloride, on compound F using a base, such as K$_2$CO$_3$, provides compound J. The hydroxyl of compound J can displace a L.G. on intermediate DD using a base, such as KOtBu, to give compound EE. The nitro group can be reduced via Fe and NH$_4$Cl, for example, to give amine FF.

Acylated chiral auxiliary HH can be reacted with 2,2-dimethoxyacetaldehyde GG using a Lewis acid, such as TiCl$_4$ or Bu$_2$BOTf along with a base, such as DIPEA, to give aldol product JJ. The chiral auxiliary is removed using AlMe$_3$ and N,O-dimethylhydroxylamine hydrochloride to provide Weinreb amide KK. Intermediate KK can be alkylated with intermediate LL using a base, such as NaH, and a phase transfer reagent, such as TBAF, to give intermediate MM. The Weinreb amide MM can be reacted with a hydride reagent, such as DIBAL-H, to give aldehyde NN. Intermediate NN can undergo reaction with CBr$_4$ and Ph$_3$P to give dibromide OO. The dibromide OO can be reacted with a base, such as n-BuLi, and an acylating reagent, such as ethyl chloroformate, to give alkyne PP. The alkyne can be hydrogenated using a Pd catalyst, such as Lindlar catalyst, to give alkene QQ. The acetal group of intermediate QQ can be removed using aqueous acid, such as HCl, to give aldehyde RR. This aldehyde can undergo reductive amination with amine FF using a hydride source, such as NaBH(OAc)$_3$, to provide amine SS. Amine SS can undergo cyclization to intermediate L using a base, such as NaOtBu. Hydrolysis of ester L via LiOH, for example, can provide compounds of Formula (I).

Scheme 2.2

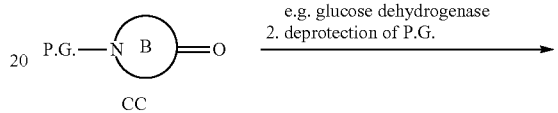

1. [H] or dynamic kinetic resolution
   e.g. glucose dehydrogenase
2. deprotection of P.G.

CC

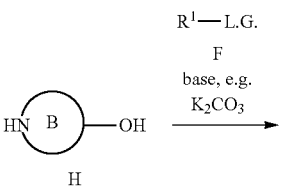

H

R$^1$—L.G.
F
base, e.g.
K$_2$CO$_3$

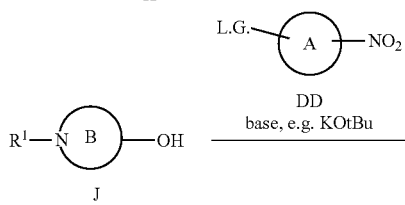

J

DD
base, e.g. KOtBu

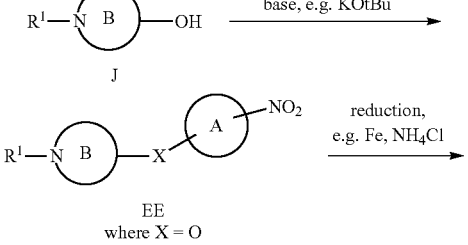

EE
where X = O reduction,
e.g. Fe, NH$_4$Cl

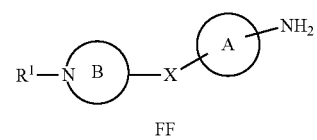

FF

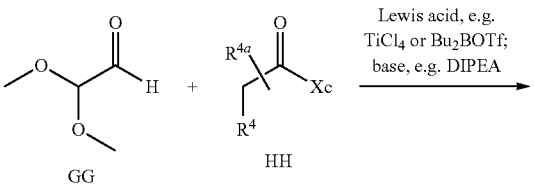

GG    HH

Lewis acid, e.g.
TiCl$_4$ or Bu$_2$BOTf;
base, e.g. DIPEA

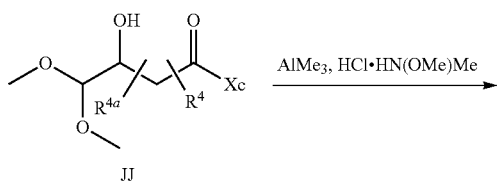

JJ

AlMe$_3$, HCl·HN(OMe)Me

-continued

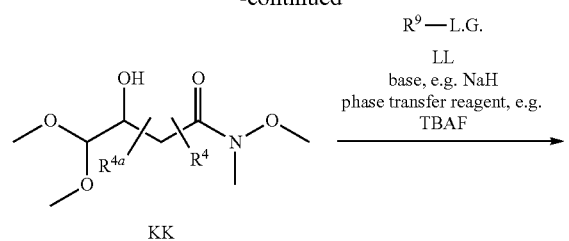

KK

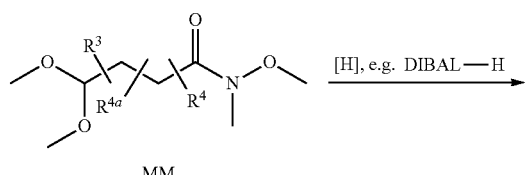

MM

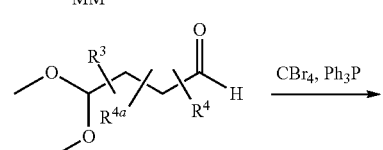

NN

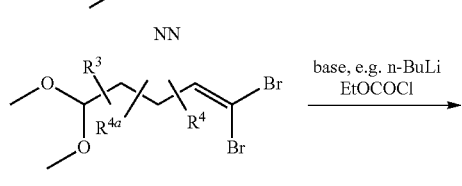

OO

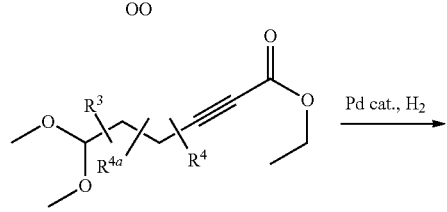

PP

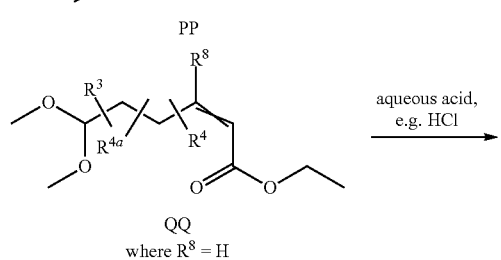

QQ
where $R^8$ = H

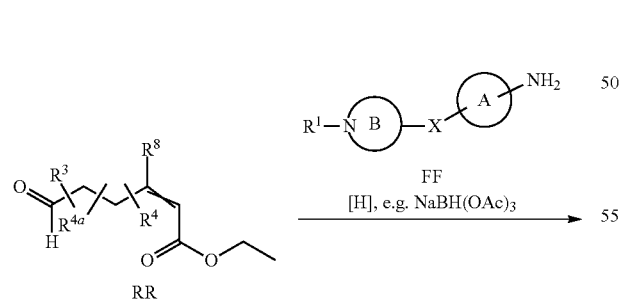

RR

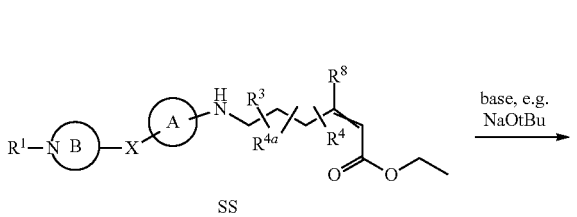

SS

-continued

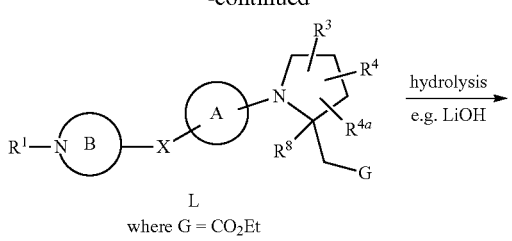

L
where G = $CO_2Et$

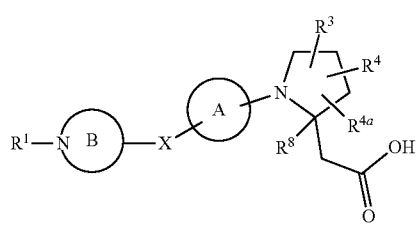

(I)

Alternatively, compounds of Formula (I) may be synthesized starting with ethyl 1-benzyl-4-oxopiperidine-3-carboxylate (intermediate M), which can be reacted with $R^2$-L.G., as an intermediate N, using a base, such as KOtBu, to provide β-ketoester O as depicted in Scheme 3. The ester can be removed via decarboxylation with acid, e.g., HCl, to provide piperidinone P. The methyl iodonium salt Q can be formed from piperidinone P using MeI. The salt Q can be converted to the piperidinone S by reaction with an amine R and base (e.g., $K_2CO_3$). The ketone S can be reduced using a hydride source, such as $NaBH_4$, to give alcohol J. Alcohol J can be converted to compounds of Formula (I) according to the sequence depicted in Scheme 1 or Scheme 2.

Scheme 3

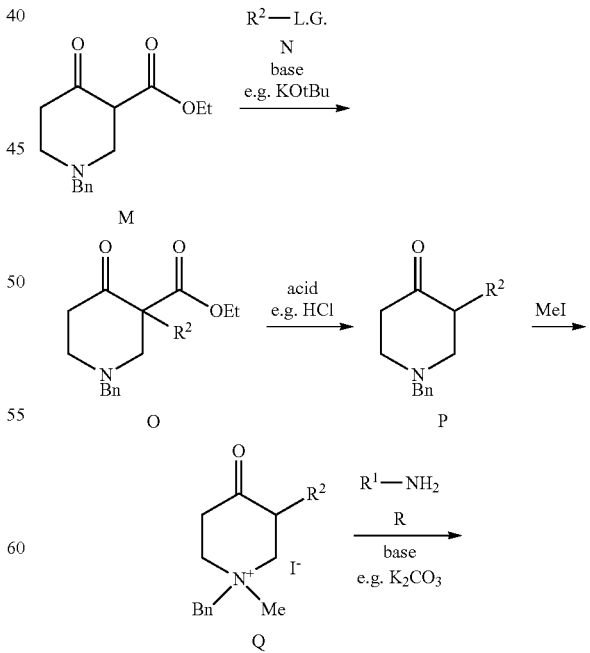

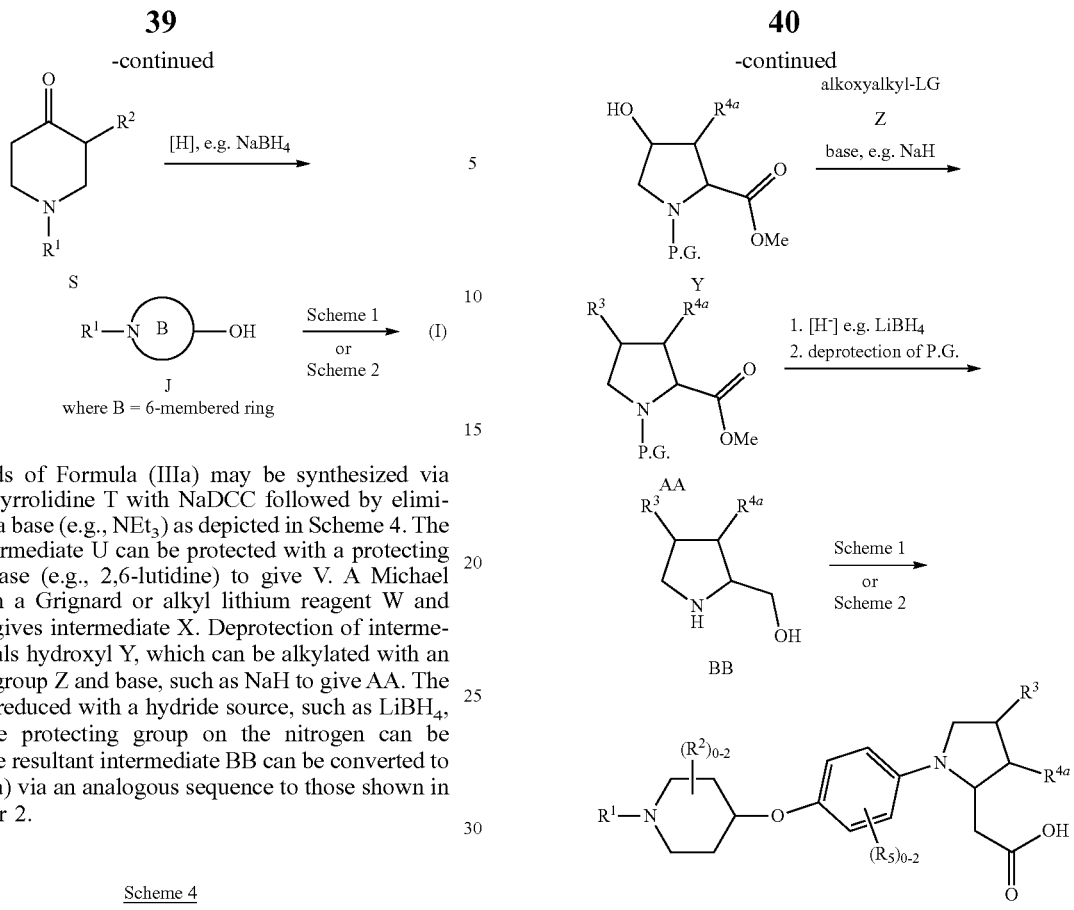

Compounds of Formula (IIIa) may be synthesized via reaction of pyrrolidine T with NaDCC followed by elimination using a base (e.g., NEt₃) as depicted in Scheme 4. The resultant intermediate U can be protected with a protecting group and base (e.g., 2,6-lutidine) to give V. A Michael reaction with a Grignard or alkyl lithium reagent W and CuBr.SMe₂ gives intermediate X. Deprotection of intermediate X reveals hydroxyl Y, which can be alkylated with an alkoxyalkyl group Z and base, such as NaH to give AA. The ester can be reduced with a hydride source, such as LiBH₄, and then the protecting group on the nitrogen can be removed. The resultant intermediate BB can be converted to Formula (IIIa) via an analogous sequence to those shown in Schemes 1 or 2.

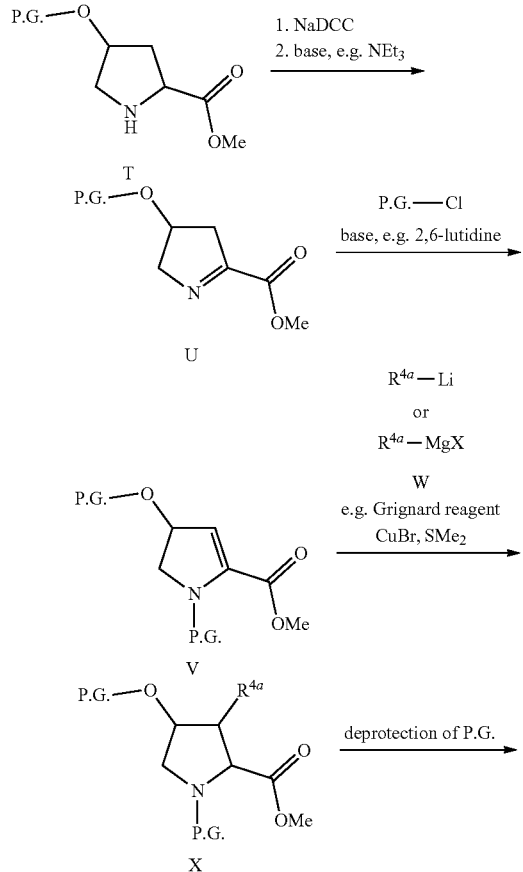

IV. Biology

Diabetes mellitus is a serious disease afflicting over 100 million people worldwide. It is diagnosed as a group of disorders characterized by abnormal glucose homeostasis resulting in elevated blood glucose. Diabetes is a syndrome with interrelated metabolic, vascular, and neuropathic components. The metabolic abnormality is generally characterized by hyperglycemia and alterations in carbohydrate, fat and protein metabolism caused by absent or reduced insulin secretion and/or ineffective insulin secretion. The vascular syndrome consists of abnormalities in the blood vessels leading to cardiovascular, retinal and renal complications. Abnormalities in the peripheral and autonomic nervous systems are also part of diabetic syndrome. Strikingly, diabetes is the fourth leading cause of global death by disease, the largest cause of kidney failure in developed countries, the leading cause of vision loss in industrialized countries and has the greatest prevalence increase in developing countries.

Type 2 diabetes, which accounts for 90% of diabetes cases, is characterized by increasing insulin resistance associated with inadequate insulin secretion after a period of compensatory hyperinsulinemia. The reasons for β cell secondary failure are not completely understood. Acquired pancreatic islet damage or exhaustion and/or genetic factors causing susceptibility to islet secretory insufficiency have been hypothesized.

Free fatty acids (FFAs) are evidenced to influence insulin secretion from β cells primarily by enhancing glucose-stimulated insulin secretion (GSIS). Although glucose is recognized as the major stimulator of insulin secretion from 1 cells, other stimuli, such as amino acids, hormones, and FFAs, also regulate insulin secretion. Thus, under normal settings, insulin secretion from β cells in response to food intake is evoked by the collective stimuli of nutrients, such as glucose, amino acids, and FFAs, and hormones like the incretin glucagon-like peptide 1 (GLP-1). Fatty acids are also known to stimulate the secretion of several gut satiety hormones, including cholocystokinine (CCK), GLP-1, and peptide YY (PYY).

G-protein coupled receptors (GPCRs) expressed in β cells are known to modulate the release of insulin in response to changes in plasma glucose levels. GPR40, also known as fatty acid receptor 1 (FFAR1), is a membrane-bound FFA receptor which is preferentially expressed in the pancreatic islets and specifically in β cells. GPR40 (e.g., human GPR40, RefSeq mRNA ID NM_005303; e.g., mouse GPR40 RefSeq mRNA ID NM_194057) is a GPCR located at chromosome 19q13.12. GPR40 is activated by medium to long chain fatty acids and thereby triggering a signaling cascade that results in increased levels of $[Ca^{2+}]_i$ in β cells and subsequent stimulation of insulin secretion (Itoh et al., *Nature*, 422:173-176 (2003)). Selective small molecule agonists of GPR40 have been shown to promote GSIS and reduce blood glucose in mice (Tan et al., *Diabetes*, 57:2211-2219 (2008)). Briefly, when activators of GPR40 are administered to either normal mice or mice that are prone to diabetes due to genetic mutation, prior to a glucose tolerance test, improvements in glucose tolerance are observed. A short-lived increase in plasma insulin levels are also observed in these treated mice. It has also been shown that GPR40 agonists restore GSIS in pancreatic β-cells from the neonatal STZ rats suggesting that GPR40 agonists will be efficacious in diabetics with compromised β-cell function and mass. Fatty acids are known to stimulate the secretion of several gut satiety hormones, including cholocystokinine (CCK), GLP-1, and peptide YY (PYY), and GPR40 has been shown to colocalize with cells that secrete such hormones (Edfalk et al., *Diabetes*, 57:2280-2287 (2008); Luo et al., *PLoS ONE*, 7:1-12 (2012)). Fatty acids are also known to play a role in neuronal development and function, and GPR40 has been reported as a potential modulator of the fatty acid effects on neurons (Yamashima, T., *Progress in Neurobiology*, 84:105-115 (2008)).

Given the increase in the worldwide patient population afflicted by type 2 diabetes, there is a need for novel therapies which are effective with minimal adverse events. To decrease medical burden of type 2 diabetes through enhanced glycemic control, GPR40 modulator compounds of the present invention are being investigated here for their incretin effect to promote GSIS as well as the potential combination with a broad range of anti-diabetic drugs.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a GPR40 modulator. Exemplary subjects include human beings of any age with risk factors for metabolic disease. Common risk factors include, but are not limited to, age, sex, weight, family history, or signs of insulin resistance such as acanthosis nigricans, hypertension, dislipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; (b) relieving the disease-state, i.e., causing regression of the disease state; and/or (c) preventing the disease-state from occurring in a mammal, in particular, when such mammal is predisposed to the disease-state but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate GPR40 and/or to prevent or treat the disorders listed herein. When applied to a combination, the term refers to combined amounts of the active ingredients that result in the preventive or therapeutic effect, whether administered in combination, serially, or simultaneously.

In Vitro GPR40 Assays

FDSS-Based Intracellular Calcium Assay

Cell lines expressing GPR40 are generated using the pDEST-3×FLAG gene expression system and are cultured in culture medium comprising the following components: F12 (Gibco #11765), 10% lipid deprived fetal bovine serum, 250 μg/ml zeocin and 500 μg/ml G418. To conduct the fluorescent imaging plate reader (FLIPR)-based calcium flux assay to measure intracellular $Ca^{2+}$ response, cells expressing GPR40 are plated on 384 well plates (BD Biocoat #356697) at a density of 20,000 cells/20 μL medium per well in phenol red and serum-free DMEM (Gibco #21063-029) and incubated overnight. Using BD kit #s 80500-310 or -301, the cells are incubated with 20 μL per well of Hank's buffered salt solution with 1.7 mM probenecid and Fluo-3 at 37° C. for 30 min. Compounds are dissolved in DMSO and diluted to desired concentrations with assay buffer and added to the cells as 3× solution (20 μL per well). Run fluorescence/luminescence reader FDSS (Hamamatsu) to read intracellular $Ca^{2+}$ response.

The exemplified Examples disclosed below were tested in the Human GRP40 In Vitro assay described above and found having hGRP40 modulating activity.

GPR40 IP-One HTRF Assays in HEK293/GPR40 Inducible Cell Lines

Human, mouse and rat GPR40-mediated intracellular IP-One HTRF assays were established using human embryonic kidney HEK293 cells stably transfected with a tetracycline-inducible human, mouse or rat GPR40 receptor. Cells were routinely cultured in growth medium containing DMEM (Gibco Cat. #12430-047), 10% qualified FBS (Sigma, Cat. #F2442), 200 μg/mL hygromycin (Invitrogen, Cat. #16087-010) and 1.5 μg/mL blasticidin (Invitrogen, Cat. #R210-01). About 12-15 million cells were passed into a T175 tissue culture flask (BD Falcon 353112) with growth medium and incubated for 16-18 hours (overnight) at 37° C. with 5% $CO_2$. The next day, assay medium was exchanged with growth medium containing 1000 ng/mL of tetracycline (Fluka Analytical, Cat. #87128) to induce GPR40 expression for 18-24 hours at 37° C. incubator with 5% $CO_2$. After induction, the cells were washed with PBS (Gibco, Cat. #14190-036) and detached with Cell Stripper (Cellgro, Cat. #25-056-CL). 10-20 mL growth medium were added to the flask and cells were collected in 50 mL tubes (Falcon, Cat. #352098) and spun at 1000 RPM for 5 minutes. Culture medium was aspirated and the cells were resuspended in 10 mL of 1×IP-One Stimulation Buffer from the Cisbio IP-One kit (Cisbio, Cat. #62IPAPEJ). The cells were diluted to 1.4×106 cells/mL in Stimulation Buffer.

Test compounds were 3-fold, 11-point serially diluted in DMSO in a REMP assay plate (Matrix Cat. #4307) by Biocel (Agilent). The compounds were transferred into an Echo plate (Labcyte, Cat. #LP-0200) and 20 nL of diluted compounds were transferred to an assay plate (proxi-plate from Perkin Elmer, Cat. #6008289) by Echo acoustic nano dispenser (Labcyte, model ECHO550). 14 μL of the diluted cells were then added to the assay plate by Thermo (SN 836 330) CombiDrop and incubated at room temperature for 45 minutes. Then 3 μL of IP1 coupled to dye D2 from the Cisbio IP-One kit were added to the assay plate followed by 3 μL of Lumi4-Tb cryptate K from the kit. The plate was further incubated at room for 1 hour before reading on the Envision (Perkin Elmer Model2101) with an HTRF protocol. Activation data for the test compound over a range of concentrations was plotted as percentage activation of the test compound (100%=maximum response). After correcting for background [(sample read−mean of low control)/(mean of high control−mean of low control)] (low control is DMSO without any compound), $EC_{50}$ values were determined. The $EC_{50}$ is defined as the concentration of test compound which produces 50% of the maximal response and was quantified using the 4 parameter logistic equation to fit the data. The maximal Y value observed (% Ymax) was calculated relative to a BMS standard reference compound at a final concentration of 0.625 μM.

Some of the exemplified Examples disclosed below were tested in the Human GRP40 In Vitro assay described above and found having hGRP40 modulating activity reported as hGPR40 IP1 $EC_{50}$.

The compounds of the present invention possess activity as modulators of GPR40, and, therefore, may be used in the treatment of diseases associated with GPR40 activity. Via modulation of GPR40, the compounds of the present invention may preferably be employed to modulate the production/secretion of insulin and/or gut hormones, such as GLP-1, GIP, CCK and amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, fatty liver disease, dyslipidemia, hyperlipidemia, hypertriglyceridemia, hypercholesterolemia, low HDL, high LDL, vascular restenosis, peripheral arterial disease, lipid disorders, liver diseases such as NASH (Non-Alcoholic SteatoHepatitis), NAFLD (Non-Alcoholic Fatty Liver Disease) and liver cirrhosis, neurodegenerative disease, cognitive impairment, dementia, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.-Imm., Endoc. & Metab. Agents*, 1:1-24 (2001).

GPR40 is expressed in neuronal cells, and is associated with development and maintenance of neuronal health in brain, as described in Yamashima, T., *Progress in Neurobiology*, 84:105-115 (2008).

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR40 modulators or one or more other suitable therapeutic agents useful in the treatment of the aforementioned disorders including: antidiabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, and appetite suppressants.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR40 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the compound of the present invention include, but are not limited to, insulin secretagogues or insulin sensitizers, other GPR40 receptor modulators, or other antidiabetic agents. These agents include, but are not limited to, dipeptidyl peptidase IV inhibitors (DPP4i; for example, sitagliptin, saxagliptin, alogliptin, vildagliptin), biguanides (for example, metformin, phenformin), sulfonyl ureas (for example, gliburide, glimepiride, glipizide), glucosidase inhibitors (for example, acarbose, miglitol), PPARγ agonists such as thiazolidinediones (for example, rosiglitazone, pioglitazone), PPAR α/γ dual agonists (for example, muraglitazar, tesaglitazar, aleglitazar), glucokinase activators (as described in Fyfe, M. C. T. et al., *Drugs of the Future*, 34(8):641-653 (2009) and incorporated herein by reference), other GPR40 receptor modulators (e.g., TAK-875), GPR119 receptor modulators (for example, MBX-2952, PSN821, APD597), GPR120 receptor modulators (for example, as described in Shimpukade, B. et al., *J. Med. Chem.*, 55(9): 4511-4515 (2012)), sodium-glucose transporter-2 (SGLT2) inhibitors (for example dapagliflozin, canagliflozin, empagliflozin, remagliflozin), 11b-HSD-1 inhibitors (for example MK-0736, BI35585, BMS-823778, and LY2523199), MGAT inhibitors (for example, as described in Barlind, J. G. et al., *Bioorg. Med. Chem. Lett.* (2013), doi: 10.1016/j.bmcl.2013.02.084), amylin analogs such as pramlintide, and/or insulin. Reviews of current and emerging therapies for the treatment of diabetes can be found in: Mohler, M. L.

et al., *Medicinal Research Reviews,* 29(1):125-195 (2009), and Mizuno, C. S. et al., *Current Medicinal Chemistry,* 15:61-74 (2008).

The GPR40 receptor modulator of formula I may also be optionally employed in combination with agents for treating complication of diabetes. These agents include PKC inhibitors and/or AGE inhibitors.

The GPR40 receptor modulator of formula I way also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The compound of structure I may also be employed in combination with an agonist of the glucagon-like peptide-1 receptor (GLP-1 R), such as exenatide, liraglutide, GPR-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., *Nature Reviews Drug Discovery,* 5:369-370 (2006); Jones, D., *Nature Reviews: Drug Discovery,* 8:833-834 (2009); Obici, S., *Endocrinology,* 150(6):2512-2517 (2009); and Elangbam, C. S., *Vet. Pathol.,* 46(1):10-24 (2009).

The above other therapeutic agents, when employed in combination with the compounds of the present invention may be used, for example, in those amounts indicated in the *Physicians' Desk Reference,* as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the GPR40 receptor. Such compounds may be provided in a commercial kit, for example, for use in pharmaceutical research involving GPR40 or anti-diabetic activity. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving GPR40.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof, and, (c) a package insert stating that the pharmaceutical composition can be used for the treatment of multiple diseases or disorders associated with GPR40 (as defined previously). In another embodiment, the package insert states that the pharmaceutical composition can be used in combination (as defined previously) with a second therapeutic agent for the treatment of multiple diseases or disorders associated with GPR40. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

EXAMPLES

The following Examples are offered as illustrative, as a partial scope and particular embodiments of the invention and are not meant to be limiting of the scope of the invention. Compounds of this invention may have one or more asymmetric centers. Throughout the examples and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention.

Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS and Preparatory/Analytical HPLC Methods Employed in Characterization or Purification of Examples Analytical HPLC/MS (unless otherwise noted) was performed on Shimadzu SCL-10A liquid chromatographs and Waters MICROMASS® ZQ Mass Spectrometers (Desolvation Gas: Nitrogen; Desolvation Temp. 250° C.; Ion Source Temp: 120° C.; Positive Electrospray conditions) using the following method Linear Gradient of 0% to 100% solvent B over 2 min, with 1 minute hold at 100% B;
UV visualization at 220 nm;
Column: PHENOMENEX® Luna C18 (2) 30 mm×4.60 mm; 5 m particle (Heated to Temp. 40° C.);
Flow rate: 5 ml/min;
Solvent A: 10% MeCN-90% $H_2O$-0.1% TFA; or, 10% MeOH-90% $H_2O$-0.1% TFA; and
Solvent B: 90% MeCN-10% $H_2O$-0.1% TFA; or, 90% MeOH-10% $H_2O$-0.1% TFA.

Preparatory HPLC (unless otherwise noted) was performed on a Shimadzu SCL-10A liquid chromatograph with a linear gradient of 20-100% Solvent B over 10 or 30 min, with either a 2 or 5 min (respectively) hold at 100% Solvent B;

UV visualization at 220 nm;
Column: PHENOMENEX® Luna Axia 5µ C18 30×100 mm;
Flow rate: 20 mL/min;
Solvent A: 10% MeCN-90% $H_2O$-0.1% TFA; and
Solvent B: 90% MeCN-10% $H_2O$-0.1% TFA.

Analytical HPLC (unless otherwise noted) was performed to determine compound purity on a Shimadzu SIL-10A using the following method (Unless otherwise stated, retention times listed in Examples refer the retention times of Column 1)

Linear Gradient of 10% to 100% solvent B over 15 min;
UV visualization at 220 nm and 254 nm;
Column 1: SunFire C18 3.5 µm, 4.6×150 mm;
Column 2: XBridge Phenyl 3.5 µm, 4.6×150 mm;
Flow rate: 1 ml/min (for both columns);
Solvent A: 5% MeCN-95% $H_2O$-0.05% TFA; and
Solvent B: 95% MeCN-5% $H_2O$-0.05% TFA.

or

Linear Gradient of stated starting percentage to 100% solvent B over 8 min;
UV visualization at 220 nm;
Column: ZORBAX® SB C18 3.5 µm, 4.6×75 mm;
Flow rate: 2.5 ml/min;
Solvent A: 10% MeOH-90% $H_2O$-0.2% $H_3PO_4$; and
Solvent B: 90% MeOH-10% $H_2O$-0.2% $H_3PO_4$.

NMR Employed in Characterization of Examples $^1$H NMR spectra (unless otherwise noted) were obtained with JEOL® or Bruker FOURIER® transform spectrometers operating at 400 MHz or 500 MHz. $^1$H-nOe experiments were performed in some cases for regiochemistry elucidation with a 400 MHz Bruker FOURIER® Transform spectrometer.

Spectral data are reported as chemical shift (multiplicity, number of hydrogens, coupling constants in Hz) and are reported in ppm (δ units) relative to either an internal standard (tetramethylsilane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$).

Example 1

2-((2S,3S,4R)-1-(4-(((3R,4R)-1-(5-Chloro-2-methoxypyridin-4-yl)-3-methylpiperidin-4-yl)oxy) phenyl)-4-(3-methoxypropoxy)-3-methylpyrrolidin-2-yl)acetic acid

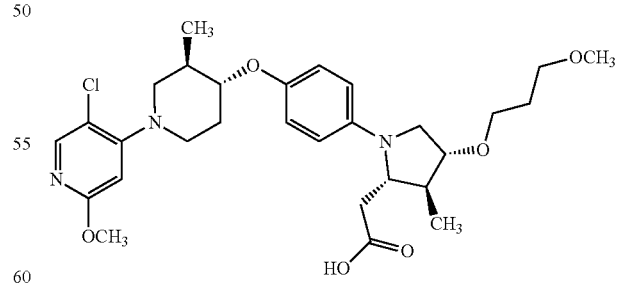

1A. (R)-1-Benzyl 2-methyl 4-((tert-butyldimethylsilyl)oxy)-4,5-dihydro-1H-pyrrole-1,2-dicarboxylate To a solution of (2S,4R)-methyl 4-hydroxypyrrolidine-2-carboxylate, HCl (10.0 g, 55.3 mmol) in $CH_2Cl_2$ (76 mL) at rt was added imidazole (8.66 g, 127 mmol) and TBS-Cl (9.17 g, 60.8 mmol). The reaction mixture was stirred at rt overnight. The reaction mixture was washed with 10% aq. Na$_2$CO$_3$ (75 mL). The layers were separated and the aqueous layer was extracted with CH$_2$Cl$_2$ (75 mL). The combined organic layers were concentrated to a small volume and then toluene was added and the fractions were concentrated to ~75 mL. The toluene phase was washed with water and then used directly in the next step. To the solution of (2S,4R)-methyl 4-((tert-butyldimethylsilyl)oxy)pyrrolidine-2-carboxylate in toluene cooled to 0° C. was added water (25 mL) followed by NaDCC (6.69 g, 30.4 mmol). After 30 min, the reaction mixture was filtered through CELITE®, washed with toluene (30 mL), and the phases were separated. The organic phase was washed with water, cooled to 0° C., and NEt$_3$ (9.3 mL, 66 mmol) was added. The reaction mixture was stirred for 1 h at 0° C. and then overnight at rt. The organic solution was washed with water (2×), dried (MgSO$_4$), and concentrated. The crude material was used directly in the next step without further purification. To a solution of (R)-methyl 3-((tert-butyldimethylsilyl)oxy)-3,4-dihydro-2H-pyrrole-5-carboxylate in CH$_2$Cl$_2$ (101 mL) at −10° C. was added 2,6-lutidine (11.8 mL, 101 mmol) followed by the dropwise addition of benzyl chloroformate (7.9 mL, 56 mmol) and the reaction mixture was warmed to rt and stirred overnight. Ethylenediamine (0.50 mL, 7.4 mmol) was added to the reaction mixture, which was stirred for 15 min at rt and then washed with 1 N aq. citric acid (60 mL) and 1 N aq. HCl (50 mL). The organic layer was washed with water, 1.5 N aq. KH$_2$PO$_4$, and brine. The organic layer was dried (Na$_2$SO$_4$), filtered, and concentrated. The crude product was purified by silica chromatography to provide 1A (16.3 g, 41.6 mmol, 82% yield) as a colorless oil. LC-MS Anal. Calc'd for C$_{20}$H$_{29}$NO$_5$Si: 391.55, found [M+H] 392.0. $^1$H NMR (500 MHz, CDCl$_3$) δ 7.40-7.29 (m, 5H), 5.69-5.62 (m, 1H), 5.20-5.11 (m, 2H), 4.94 (dt, J=7.7, 3.2 Hz, 1H), 3.98 (dd, J=12.4, 8.0 Hz, 1H), 3.79 (dd, J=12.2, 3.4 Hz, 1H), 3.71-3.62 (m, 3H), 0.88 (s, 9H), 0.07 (d, J=3.3 Hz, 6H).

1B. (2R,3S,4R)-1-Benzyl 2-methyl 4-((tert-butyldimethylsilyl)oxy)-3-methylpyrrolidine-1,2-dicarboxylate CuBr.SMe$_2$ (4.78 g, 23.2 mmol) was suspended in anhydrous Et$_2$O (51 mL) and cooled to −40° C. A 1.6 M solution of MeLi in Et$_2$O (29.1 mL, 46.5 mmol) was added dropwise via addition funnel. The solution was stirred for 1 h and then a solution of 1A (7.00 g, 17.9 mmol) in Et$_2$O (20.4 mL) was added dropwise via addition funnel. The reaction mixture was stirred for 45 min at −45° C. and then transferred via cannula to a vigorously stirred solution of sat. aq. NH$_4$Cl and stirred for 30 min. The organic layer was separated and washed with sat. aq. NH$_4$Cl. The combined aqueous layers were extracted with hexanes. The combined organic layers were dried (MgSO$_4$) and concentrated. The crude material was purified by silica chromatography to obtain 1B (5.11 g, 12.5 mmol, 70% yield) as a colorless oil. LC-MS Anal. Calc'd for C$_{21}$H$_{33}$NO$_5$Si: 407.58, found [M+H] 408.2. $^1$H NMR (500 MHz, CDCl$_3$) δ (two rotamers) 7.40-7.27 (m, 5H), 5.21-5.00 (m, 2H), 4.01-3.90 (m, 1H), 3.87-3.80 (m, 1.6H), 3.77-3.71 (s and m, 1.8H), 3.57 (s, 1.6H), 3.36-3.28 (m, 1H), 2.33-2.25 (m, 1H), 1.11 (dd, J=7.2, 2.2 Hz, 3H), 0.86 (s, 9H), 0.08-0.01 (m, 6H).

1C. (2R,3S,4R)-1-Benzyl 2-methyl 4-hydroxy-3-methylpyrrolidine-1,2-dicarboxylate To a solution of 1B (5.10 g, 12.5 mmol) in THF (42 mL) was added a 1 M solution of TBAF in THF (19 mL, 19 mmol) and the reaction mixture was stirred at rt for 1 h. The reaction mixture was diluted with EtOAc and washed with water and brine, dried (MgSO$_4$), and concentrated. The crude material was purified by silica chromatography to obtain 1C (3.61 g, 12.3 mmol, 98% yield) as a colorless oil, which crystallized to a white solid upon standing. LC-MS Anal. Calc'd for C$_{15}$H$_{19}$NO$_5$: 293.32, found [M+H] 294.0. $^1$H NMR (400 MHz, CDCl$_3$) δ 7.41-7.27 (m, 5H), 5.25-4.97 (m, 2H), 4.09-3.96 (m, 1H), 3.95-3.87 (m, 1H), 3.86-3.70 (m, 3H), 3.69-3.57 (m, 2H), 3.10-2.83 (m, 1H), 2.37 (td, J=6.9, 2.9 Hz, 1H), 1.12 (d, J=7.3 Hz, 3H).

1D. (2R,3S,4R)-1-Benzyl 2-methyl 4-(allyloxy)-3-methylpyrrolidine-1,2-dicarboxylate To a solution of 1C (0.405 g, 1.38 mmol) in DMF (6.9 mL) at 0° C. was added 60% NaH (0.083 g, 2.1 mmol). The reaction mixture was stirred for 30 min and then allyl bromide (0.18 mL, 2.1 mmol) was added. The reaction mixture was warmed to rt and stirred for 1 h. The reaction mixture was quenched with water and diluted with EtOAc. The layers were separated and the organic layer was washed with water (4×). The organic layer was washed with brine, dried (MgSO$_4$), and concentrated. The crude product was purified by silica chromatography to provide 1D (0.446 g, 1.34 mmol, 97% yield) as a colorless oil. LC-MS Anal. Calc'd for C$_{18}$H$_{23}$NO$_5$: 333.38, found [M+H]334.0. $^1$H NMR (500 MHz, CDCl$_3$) δ (two rotamers) 7.41-7.27 (m, 5H), 5.90-5.77 (m, 1H), 5.29-4.99 (m, 4H), 4.09-3.90 (m, 3H), 3.86 and 3.80 (2 dd, J=11.3, 5.6 Hz, 1H), 3.73 and 3.57 (2 s, 3H), 3.67-3.61 (m, 1H), 3.46 (ddd, J=11.0, 6.1, 4.7 Hz, 1H), 2.59-2.44 (m, 1H), 1.14 (dd, J=7.2, 1.1 Hz, 3H).

1E. (2R,3S,4R)-1-Benzyl 2-methyl 4-(3-hydroxypropoxy)-3-methylpyrrolidine-1,2-dicarboxylate To a solution of 1D (2.74 g, 8.20 mmol) in THF (4.1 mL) at 0° C. was added a 1 M solution of BH$_3$.THF (2.8 mL, 2.8 mmol) in THF. After 15 min, the reaction mixture was stirred at rt for 2.2 h. Additional BH$_3$.THF (1 M in THF) (0.2 mL, 0.2 mmol) was added and the reaction mixture was stirred for an additional 15 min. Water (4.1 mL) and sodium perborate-4H$_2$O (1.29 g, 8.37 mmol) were added. After stirring for 2 h, the reaction mixture was diluted with EtOAc, washed with brine, dried (MgSO$_4$), and concentrated. The crude product was purified by silica chromatography to provide 1E (2.17 g, 6.18 mmol, 75% yield) as a colorless oil. LC-MS Anal. Calc'd for C$_{18}$H$_{25}$NO$_6$: 351.39, found [M+H] 352.0. $^1$H NMR (500 MHz, CDCl$_3$) δ (two rotamers) 7.43-7.27 (m, 5H), 5.26-5.00 (m, 2H), 4.18-3.98 (m, 1H), 3.84-3.76 (m, 1H), 3.75 and 3.61 (two s, 3H), 3.73-3.66 (m, 2H), 3.61-3.50 (m, 4H), 2.62-2.50 (m, 1H), 2.04-2.00 (m, 1H), 1.77 (quind, J=5.7, 2.9 Hz, 2H), 1.12 (d, J=7.2 Hz, 3H).

1F. (2R,3S,4R)-1-Benzyl 2-methyl 4-(3-methoxypropoxy)-3-methylpyrrolidine-1,2-dicarboxylate To a solution of 1E (2.17 g, 6.18 mmol) in MeCN (7.7 mL) was added Ag$_2$O (3.58 g, 15.4 mmol) and MeI (3.9 mL, 62 mmol). The reaction mixture was stirred at 50° C. for 18 h. The mixture was filtered and concentrated. The crude product was purified by silica chromatography to provide 1F (2.71 g, 7.42 mmol, 81% yield). LC-MS Anal. Calc'd for C$_{19}$H$_{27}$NO$_6$: 365.42, found [M+H] 367.0. $^1$H NMR (500 MHz, CDCl$_3$) δ 7.41-7.27 (m, 5H), 5.24-4.99 (m, 2H), 4.08-3.94 (m, 1H), 3.89-3.76 (m, 1H), 3.73, 3.58 (2 s, 3H), 3.57-3.53 (m, 1H), 3.51-3.42 (m, 3H), 3.40 (t, J=6.2 Hz, 2H), 3.32, 3.3 (2 s, 3H), 2.49 (dtd, J=6.9, 4.7, 2.2 Hz, 1H), 1.76 (quind, J=6.3, 2.1 Hz, 2H), 1.13 (dd, J=7.2, 3.0 Hz, 3H).

1G. (2R,3S,4R)-Benzyl 2-(hydroxymethyl)-4-(3-methoxypropoxy)-3-methylpyrrolidine-1-carboxylate To a solution of 1F (4.13 g, 11.3 mmol) in THF (57 mL) at 0° C. was added a 2 M solution of LiBH$_4$ (11.3 mL, 22.6 mmol) in THF. The reaction mixture was warmed to rt and stirred for 17 h. The reaction mixture was cooled to 0° C., carefully quenched with sat. aq. NH$_4$Cl, and diluted with EtOAc/water. The layers were separated and the organic layer was washed with brine, dried (MgSO$_4$), and concentrated. The crude product was purified by silica chromatography to provide 1G (3.25 g, 9.15 mmol, 81%) as a colorless oil. LC-MS Anal. Calc'd for $C_{18}H_{27}NO_5$: 337.41, found [M+H] 338.0. $^1$H NMR (500 MHz, CDCl$_3$) δ 7.40-7.28 (m, 5H), 5.14 (s, 2H), 4.41-4.31 (m, 1H), 3.85-3.70 (m, 3H), 3.69-3.61 (m, 1H), 3.57-3.47 (m, 3H), 3.46-3.39 (m, 2H), 3.34-3.26 (m, 3H), 2.06-1.94 (m, 1H), 1.81 (quin, J=6.4 Hz, 2H), 1.09 (dd, J=9.9, 7.2 Hz, 3H).

1H. ((2R,3S,4R)-4-(3-Methoxypropoxy)-3-methylpyrrolidin-2-yl)methanol

A mixture of 1G (3.25 g, 9.63 mmol) and Pd/C (0.820 g, 0.771 mmol) in MeOH (193 mL) was purged with argon (3×) and then H$_2$ (3×). The reaction mixture was stirred under H$_2$ (1 atm) at rt for 3.5 h. The mixture was filtered through CELITE® and concentrated to give 1H (2.03 g, 9.99 mmol, 100% yield). LC-MS Anal. Calc'd for $C_{10}H_{21}NO_3$: 203.28, found [M+H] 204.1. $^1$H NMR (500 MHz, CDCl$_3$) δ 3.63 (dd, J=11.1, 3.4 Hz, 1H), 3.55-3.49 (m, 2H), 3.47 (t, J=6.3 Hz, 2H), 3.43 (td, J=6.3, 2.1 Hz, 2H), 3.31 (s, 3H), 3.06-3.00 (m, 1H), 2.98-2.90 (m, 1H), 2.85-2.76 (m, 1H), 1.85 (dt, J=6.9, 3.4 Hz, 1H), 1.83-1.75 (m, 2H), 1.05 (d, J=7.2 Hz, 3H).

1I. 4-Bromo-2-methoxypyridine

A heterogeneous reaction mixture of 4-bromo-2-fluoropyridine (2.64 mL, 25.6 mmol) and NaOMe (8.29 g, 153 mmol) in MeOH (36.5 mL) was reacted in a pressure tube at 155° C. for 5 h. The reaction mixture was cooled to rt and the solids were filtered and washed with EtOAc. The filtrate was concentrated to a pale yellow oil with some white solids. The oil yellow was decanted and diluted with water and the solution was extracted with EtOAc (2×). The combined organic layers were washed with water and brine, dried over MgSO$_4$, filtered, and concentrated to obtain 1I (4.43 g, 21.20 mmol, 83% yield) as a yellow oil. LC-MS Anal. Calc'd for $C_6H_6BrNO$: 188.02, found [M+H] 187.9, 189.9. $^1$H NMR (400 MHz, CDCl$_3$) δ 7.98 (d, J=5.5 Hz, 1H), 7.02 (dd, J=5.5, 1.5 Hz, 1H), 6.94 (d, J=1.8 Hz, 1H), 3.92 (s, 3H).

1J. 4-Bromo-5-chloro-2-methoxypyridine

To a solution of 1I (2.00 g, 10.6 mmol) in DMF (21 mL) was added NCS (2.98 g, 22.3 mmol). The reaction mixture was stirred at rt overnight. The reaction mixture was quenched with water, diluted with EtOAc, and the layers were separated. The aqueous layer was extracted with EtOAc and the combined organic extracts were washed with brine, dried over MgSO$_4$, and concentrated. The crude product was purified by silica chromatography to provide 1J (2.15 g, 9.18 mmol, 86% yield) as a white solid. LC-MS Anal. Calc'd for $C_6H_5BrClNO$: 220.92, found [M+H] 223.8. $^1$H NMR (400 MHz, CDCl$_3$) δ 8.15 (s, 1H), 7.05 (s, 1H), 3.91 (s, 3H).

1K. (3,4-cis)-1-Benzyl-3-methylpiperidin-4-ol

To a solution of 1-benzyl-3-methylpiperidin-4-one (24.8 g, 122 mmol) in THF (102 mL) at −78° C. was added dropwise a 1 M solution of L-Selectride (183 mL, 183 mmol) in THF. The reaction mixture was stirred at −78° C. for 90 min. EtOH (22 mL), water (55 mL), and 1 M aq. NaOH (55 mL) were added sequentially. The reaction mixture was warmed to 0° C. and 30% aq. H$_2$O$_2$ (55 mL) was added dropwise. The cold bath was removed and the reaction mixture was stirred at rt for 2 h. The reaction mixture was diluted with EtOAc and the insoluble white solid was discarded. The organic layer was washed with sat. aq. NaHCO$_3$ and brine, dried (MgSO$_4$), and concentrated to give the crude product as an oil. Purification via silica chromatography gave 1K as a white solid (22.2 g, 88% yield). LC-MS Anal. Calc'd for $C_{13}H_{19}NO$: 205.30, found [M+H] 206.2. $^1$H NMR (500 MHz, CDCl$_3$) δ 7.40-7.20 (m, 5H), 3.84 (s, 1H), 3.55 (s, 2H), 2.60-1.73 (m, 7H), 0.97 (d, 3H).

1L. (3,4-cis)-1-Benzyl-4-((tert-butyldimethylsilyl)oxy)-3-methylpiperidine

To a solution of 1K (21.86 g, 106.5 mmol) and NEt$_3$ (44.5 mL, 320 mmol) in CH$_2$Cl$_2$ (107 mL) at 0° C. was added TBSOTf (29.4 mL, 128 mmol). The reaction mixture was stirred at 0° C. for 1 h. Sat. aq. NaHCO$_3$ (180 mL) was added slowly to the reaction mixture. The mixture was concentrated, diluted with EtOAc, washed with water and brine, dried (MgSO$_4$), and concentrated. Purification via silica chromatography gave 1 L as an oil (31.48 g, 92% yield). LC-MS Anal. Calc'd for $C_{19}H_{33}NOSi$: 319.56, found [M+H] 320.3.

1M. (3,4-cis)-4-((tert-Butyldimethylsilyl)oxy)-3-methylpiperidine

A mixture of 1 L (15.7 g, 49.3 mmol) and 10% Pd/C (3.15 g) in MeOH (493 mL) was purged with argon (3×) and H$_2$ (3×). The reaction mixture was stirred under H$_2$ (1 atm) at rt for 24 h. The mixture was filtered through CELITE® and the filtrate was concentrated to give 1M (11.3 g, 49.3 mmol, 100% yield). $^1$H NMR (500 MHz, CDCl$_3$) δ 3.80 (s, 1H), 2.90 (m, 1H), 2.70-2.50 (m, 4H), 1.60-1.50 (m, 3H), 0.86 (s, 9H), 0.80 (d, 3H), 0.00 (s, 6H).

1N. 4-((3,4-cis)-4-((tert-Butyldimethylsilyl)oxy)-3-methylpiperidin-1-yl)-5-chloro-2-methoxypyridine A mixture of 1J (9.70 g, 43.6 mmol), 1M (10.0 g, 43.6 mmol), and K$_2$CO$_3$ (12.0 g, 87.0 mmol) in DMSO (14.5 mL) was vigorously stirred at 110° C. overnight. The reaction mixture was diluted with water and extracted with EtOAc. The organic layer was washed with water and brine, dried (MgSO$_4$), and concentrated. Purification via silica chromatography gave 1N as an oil (14.3 g, 38.6 mmol, 77% yield). LC-MS Anal. Calc'd for $C_{18}H_{31}ClN_2O_2Si$: 370.18, found [M+H] 371.2. $^1$H NMR (400 MHz, CDCl$_3$) δ 7.94 (s, 1H), 6.27 (s, 1H), 3.90-3.85 (m, 4H), 3.25 (dtd, J=11.7, 3.9, 1.8 Hz, 1H), 3.14-3.02 (m, 2H), 2.84 (t, J=11.0 Hz, 1H), 2.00-1.88 (m, 1H), 1.88-1.81 (m, 1H), 1.80-1.71 (m, 1H), 0.94-0.89 (m, 12H), 0.06 (s, 6H).

1O. (3,4-cis)-1-(5-Chloro-2-methoxypyridin-4-yl)-3-methylpiperidin-4-ol

To a solution of 10 (10.0 g, 27.0 mmol)) in THF (27 mL) was added a 1 M solution of TBAF in THF (81 mL, 81 mmol). The reaction mixture was stirred at 23° C. for 16 h. Sat. aq. NaHCO$_3$ (100 mL) was added slowly to the reaction mixture. The mixture was extracted with EtOAc (2×100 mL) and the combined organic extracts were washed with water (50 mL) and brine (50 mL), dried (Na$_2$SO$_4$), filtered, and concentrated. Purification via silica chromatography gave 10 as white foam (7.00 g, 27.0 mmol, 99% yield). LC-MS Anal. Calc'd for C$_{12}$H$_{17}$ClN$_2$O$_2$: 256.10, found [M+H] 257.0. $^1$H NMR (400 MHz, CDCl$_3$) δ 7.96 (s, 1H), 6.27 (s, 1H), 3.98-3.91 (m, 1H), 3.88 (s, 3H), 3.26-3.18 (m, 1H), 3.16-3.06 (m, 2H), 2.90 (dd, J=11.7, 9.9 Hz, 1H), 2.11-2.00 (m, 1H), 2.00-1.84 (m, 2H), 1.40 (d, J=3.7 Hz, 1H), 1.03 (d, J=6.8 Hz, 3H).

1P. (3,4-cis)-1-(5-Chloro-2-methoxypyridin-4-yl)-3-methylpiperidin-4-ol, Isomer 1 and Isomer 2

10 (8.8 g, 34.2 mmol) was separated by chiral SFC to give 1P as single isomers. 1P, Isomer 1 (3.00 g, 11.7 mmol, 34% yield) was isolated as a colorless oil. LC-MS Anal. Calc'd for C$_{12}$H$_{17}$ClN$_2$O$_2$: 256.10, found [M+H] 257.0. $^1$H NMR (400 MHz, CDCl$_3$) δ 7.96 (s, 1H), 6.27 (s, 1H), 3.97-3.91 (m, 1H), 3.88 (s, 3H), 3.27-3.17 (m, 1H), 3.16-3.04 (m, 2H), 2.90 (dd, J=11.7, 9.9 Hz, 1H), 2.05 (dd, J=6.9, 2.9 Hz, 1H), 2.00-1.83 (m, 2H), 1.42 (d, J=3.8 Hz, 1H), 1.03 (d, J=7.0 Hz, 3H). 1P, Isomer 2 (3.00 g, 11.7 mmol, 34% yield) was isolated as a colorless oil. LC-MS Anal. Calc'd for C$_{12}$H$_{17}$ClN$_2$O$_2$: 256.10, found [M+H] 257.0. $^1$H NMR (400 MHz, CDCl$_3$) δ 7.96 (s, 1H), 6.27 (s, 1H), 3.97-3.91 (m, 1H), 3.88 (s, 3H), 3.27-3.17 (m, 1H), 3.16-3.04 (m, 2H), 2.90 (dd, J=11.7, 9.9 Hz, 1H), 2.05 (dd, J=6.9, 2.9 Hz, 1H), 2.00-1.83 (m, 2H), 1.42 (d, J=3.8 Hz, 1H), 1.03 (d, J=7.0 Hz, 3H).

1Q. 5-Chloro-4-((3,4-trans)-4-(4-iodophenoxy)-3-methylpiperidin-1-yl)-2-methoxypyridine To a solution of 1P, Isomer 1 (0.519 g, 2.02 mmol), 4-iodophenol (0.579 g, 2.63 mmol), and Bu$_3$P (0.80 mL, 3.2 mmol) in toluene (25 mL) was added ADDP (0.817 g, 3.24 mmol). The reaction mixture was sonicated for 99 min. The reaction mixture was poured into hexanes, filtered, and concentrated. The crude product was purified by silica chromatography to provide 1Q (0.482 g, 1.05 mmol, 52% yield) as a colorless oil. LC-MS Anal. Calc'd for C$_{18}$H$_{20}$ClIN$_2$O$_2$: 458.72, found [M+H] 459.0. $^1$H NMR (400 MHz, CDCl$_3$) δ 7.98 (s, 1H), 7.61-7.50 (m, 2H), 6.75-6.66 (m, 2H), 6.27 (s, 1H), 3.99-3.90 (m, 1H), 3.89 (s, 3H), 3.56-3.46 (m, 2H), 2.93-2.82 (m, 1H), 2.65 (dd, J=12.3, 9.0 Hz, 1H), 2.23-2.08 (m, 2H), 1.82 (dtd, J=13.1, 9.7, 3.9 Hz, 1H), 1.10 (d, J=6.6 Hz, 3H).

1R. ((2R,3S,4R)-1-(4-(((3,4-trans)-1-(5-Chloro-2-methoxypyridin-4-yl)-3-methylpiperidin-4-yl)oxy)phenyl)-4-(3-methoxypropoxy)-3-methylpyrrolidin-2-yl)methanol 1Q (0.191 g, 0.416 mmol), 1H (0.0770 g, 0.379 mmol), CuI (0.014 g, 0.076 mmol), and NaOH (0.045 g, 1.1 mmol) were combined in a microwave tube, which was purged with argon. n-BuOH (1.9 mL) was added and the reaction mixture was heated to 90° C. overnight. The reaction mixture was cooled to rt and quenched with sat. aq. NH$_4$Cl. The product was extracted with CH$_2$Cl$_2$ (3×). The combined organic layers were washed with brine, dried (MgSO$_4$), and concentrated. The crude product was purified by silica chromatography to provide 1R (0.144 g, 0.269 mmol, 71% yield) as an amber oil. LC-MS Anal. Calc'd for C$_{28}$H$_{40}$ClN$_3$O$_5$: 534.09, found [M+H] 534.2. $^1$H NMR (400 MHz, CDCl$_3$) δ 7.96 (s, 1H), 6.86 (d, J=9.0 Hz, 2H), 6.59 (d, J=9.0 Hz, 2H), 6.26 (s, 1H), 3.95-3.89 (m, 1H), 3.88 (s, 3H), 3.77 (td, J=8.6, 4.1 Hz, 1H), 3.74-3.67 (m, 2H), 3.65-3.54 (m, 3H), 3.54-3.49 (m, 3H), 3.48-3.40 (m, 3H), 3.33 (s, 3H), 2.86-2.77 (m, 2H), 2.62 (dd, J=12.1, 9.2 Hz, 1H), 2.46 (q, J=7.3 Hz, 1H), 2.20-2.07 (m, 2H), 1.89-1.75 (m, 3H), 1.14 (d, J=6.6 Hz, 3H), 1.05 (d, J=7.3 Hz, 3H).

1S. 2-((2S,3S,4R)-1-(4-(((3,4-trans)-1-(5-Chloro-2-methoxypyridin-4-yl)-3-methylpiperidin-4-yl)oxy)phenyl)-4-(3-methoxypropoxy)-3-methylpyrrolidin-2-yl)acetonitrile 1R (0.144 g, 0.269 mmol) was dissolved in CH$_2$Cl$_2$ (2.7 mL) and the solution was cooled to 0° C. MsCl (0.031 mL, 0.40 mmol) and NEt$_3$ (0.075 mL, 0.54 mmol) were added sequentially and the reaction mixture was stirred at 0° C. for 40 min. The reaction mixture was diluted with EtOAc and washed with 1 N aq. HCl, sat. aq. NaHCO$_3$, and brine. The organic layer was dried (MgSO$_4$) and concentrated. The crude product was redissolved in DMSO (2.7 mL) and NaCN (0.053 g, 1.1 mmol) was added. The reaction mixture was stirred at 50° C. overnight. The reaction mixture was cooled to rt and quenched with water. The product was extracted with EtOAc (3×). The combined organic layers were washed with brine, dried (MgSO$_4$), and concentrated. The crude product was purified by silica chromatography to provide 1S (0.1294 g, 0.238 mmol, 88% yield) as a colorless oil. LC-MS Anal. Calc'd for C$_{29}$H$_{39}$ClN$_4$O$_4$: 543.10, found [M+H] 543.2. $^1$H NMR (400 MHz, CDCl$_3$) δ 7.97 (s, 1H), 6.90 (d, J=9.0 Hz, 2H), 6.49 (d, J=9.0 Hz, 2H), 6.26 (s, 1H), 3.89 (s, 3H), 3.83-3.72 (m, 2H), 3.69 (dd, J=9.1, 3.4 Hz, 1H), 3.63-3.46 (m, 6H), 3.44 (t, J=6.2 Hz, 2H), 3.35-3.32 (m, 3H), 2.90-2.71 (m, 3H), 2.68-2.49 (m, 2H), 2.22-2.08 (m, 2H), 1.89-1.74 (m, 3H), 1.14 (d, J=6.6 Hz, 3H), 1.05 (d, J=7.3 Hz, 3H).

1T. 2-((2S,3S,4R)-1-(4-(((3,4-trans)-1-(5-Chloro-2-methoxypyridin-4-yl)-3-methylpiperidin-4-yl)oxy)phenyl)-4-(3-methoxypropoxy)-3-methylpyrrolidin-2-yl)acetate A ~3 M HCl/MeOH/CH$_2$Cl$_2$ solution [25.2 mL, prepared by addition of AcCl (5.2 mL) to a 3/2 CHCl$_2$/MeOH solution (20 mL) at 0° C. and then stirring at rt for 20 min] was added to 1S (0.129 g, 0.238 mmol). The resulting solution was allowed to stand at rt for 72 h. The reaction mixture was concentrated and rotovapped down with MeOH (2×). Then a ~3M HCl/MeOH solution [25.2 mL, prepared by addition of AcCl (5.2 mL) to a 3/2 CHCl$_2$/MeOH solution (20 mL) at 0° C. and then stirring at rt for 20 min] was added to the residue, which was heated to 40° C. overnight without stirring. The reaction mixture was concentrated and neutralized with sat. aq. Na$_2$CO$_3$. The product was extracted with CH$_2$Cl$_2$ (3×). The combined organic layers were washed with brine, dried (MgSO$_4$), and concentrated. The crude product was purified by silica chromatography followed by RP-Prep HPLC and neutralized with sat. aq. NaHCO$_3$ to provide 1T (0.0809 g, 0.140 mmol, 59% yield) as a colorless oil. LC-MS Anal. Calc'd for C$_{30}$H$_{42}$ClN$_3$O$_6$: 576.12, found [M+] 576.3. $^1$H NMR (500 MHz, CDCl$_3$) δ 7.97 (s, 1H), 6.88 (d, J=9.1 Hz, 2H), 6.51 (d, J=9.1 Hz, 2H), 6.26 (s, 1H), 3.88 (s, 3H), 3.80-3.74 (m, 2H), 3.72 (br. s, 1H), 3.71 (s, 3H), 3.60-3.48 (m, 4H), 3.47-3.42 (m, 4H), 3.34-3.31 (m, 3H), 2.85-2.77 (m, 2H), 2.75-2.67 (m, 1H), 2.62 (dd, J=12.4, 9.4 Hz, 1H), 2.36 (q, J=7.4 Hz, 1H), 2.19-2.08 (m, 2H), 1.87-1.76 (m, 3H), 1.14 (d, J=6.6 Hz, 3H), 1.01 (d, J=7.4 Hz, 3H).

Example 1

To a solution of 1T (0.0809 g, 0.140 mmol) in THF (3.9 mL), i-PrOH (0.39 mL), and water (0.39 mL) was added 1 M aq. LiOH (0.70 mL, 0.70 mmol). The reaction mixture was stirred at rt overnight. The reaction mixture was mostly concentrated and then diluted with water/hexanes. The layers were separated and the aqueous layer was acidified to pH 2 with 1 M aq. HCl. The product was extracted with CH$_2$Cl$_2$ (3×). The combined organic layers were dried (MgSO$_4$) and concentrated to provide Example 1 (0.0773 g, 0.136 mmol, 97% yield) as a white foam as a single isomer. LC-MS Anal. Calc'd for C$_{29}$H$_{40}$ClN$_3$O$_6$: 562.10, found [M+] 562.2. $^1$H NMR (500 MHz, CD$_2$Cl$_2$) δ 7.95 (s, 1H), 6.89 (d, J=9.1 Hz, 2H), 6.63 (d, J=8.8 Hz, 2H), 6.29 (s, 1H), 3.86 (s, 3H), 3.81 (td, J=8.7, 4.0 Hz, 1H), 3.75-3.70 (m, 1H), 3.65 (br. s, 1H), 3.60-3.54 (m, 1H), 3.54-3.40 (m, 7H), 3.30 (s, 3H), 2.87-2.80 (m, 1H), 2.80-2.68 (m, 2H), 2.63 (dd, J=12.1, 9.4 Hz, 1H), 2.39-2.32 (m, J=7.2 Hz, 1H), 2.20-2.13 (m, 1H), 2.13-2.05 (m, 1H), 1.86-1.79 (m, 2H), 1.79-1.72 (m, 1H), 1.12 (d, J=6.6 Hz, 3H), 1.04 (d, J=7.2 Hz, 3H). Analytical HPLC: RT=10.0 min, HI: 98.9%. hGPR40 EC$_{50}$=56 nM. hGPR40 IP1 EC$_{50}$=5 nM.

1U. (3R,4R)-1-Benzyl-3-methylpiperidin-4-ol

A 20 L reactor was sequentially rinsed with 2.0 L of MeOH and 2.0 L of MILLI-Q® water. The reactor was charged with 1.0 kg of 1-benzyl-3-methylpiperidin-4-one and 7.8 L of water under a nitrogen atmosphere at 25° C. The vessel was charged with 1.2 kg of D-(+)-glucose, 1.0 L of pH 7.0 phosphate buffer, and 0.5 L of pH 7.4 tris-chloride buffer. The mixture was stirred for 10 min. To the solution was added 6.64 g of nicotinamide adenine dinucleotide and 20 g of glucose dehydrogenase (GDH-105, Codexis). The reaction temperature was gradually raised to 30° C. and the solution was agitated for 36 h. The reaction mixture was cooled to 10° C. and the pH was adjusted to 11 with NaOH. The resulting solution was stirred for 1 h and then filtered though a 10 m filter cloth. The solids were washed with water and allowed to suction dry for 3 h. The residue was dissolved in 20 L of MTBE and the insoluble material was removed via filtration. The organic layer was concentrated to 3.0 kg weight and 5.0 L of heptane was added. The solution was concentrated at 45° C. to 5 kg weight followed by stirring for 1 h during crystallization. The mixture was filtered and the solids were dried to give 0.785 kg (78% yield) of 1U as a pale yellow solid. LC-MS Anal. Calc'd for C$_{13}$H$_{19}$NO: 205.30, found [M+H] 206.1. $^1$H NMR (400 MHz, CDCl$_3$) δ 7.33-7.24 (m, 5H), 3.48 (s, 2H), 3.14-3.13 (m, 1H), 2.88-2.77 (m, 2H), 2.05 (dd, J=2.8, 12 Hz, 1H), 1.99-1.87 (m, 1H), 1.73-1.58 (m, 4H), 0.95 (d, J=6.4, 3H).

1V. (3R,4R)-1-(5-Chloro-2-methoxypyridin-4-yl)-3-methylpiperidin-4-ol, MSA salt

MeOH (23.9 kg) was charged into a 250 L hydrogenator. 1U (2.92 kg) was dissolved in MeOH (14.6 kg) and charged into the above hydrogenator. Nitrogen gas pressure (0.5 kg/cm$^2$) was applied. The reaction mixture was stirred for 5 min followed by the release of nitrogen gas pressure. This operation was repeated (3×). A slurry of 10% Pd(OH)$_2$ (290 g) in MeOH (10.8 L) was charged into the above hydrogenator at rt. Nitrogen gas pressure (0.5 kg/cm$^2$) was applied. The reaction mixture was stirred for 5 min followed by the release of nitrogen gas pressure. This operation was repeated (3×). Acetic acid (0.15 L) and MeOH (4.0 L) were charged into the above hydrogenator. Nitrogen gas pressure (0.5 kg/cm$^2$) was applied. The reaction mixture was stirred for 5 min followed by the release of nitrogen gas pressure. This operation was repeated (3×). The hydrogenator was pressurized with 4.7 kg/cm$^2$ of hydrogen gas pressure. The reaction mixture was stirred under 4.0-5.0 kg/cm$^2$ of hydrogen gas pressure at ambient temperature (20-35° C.) for 16 h. The hydrogen gas pressure was released. Nitrogen gas pressure (0.5 kg/cm$^2$) was applied to the hydrogenate. The reaction mixture was stirred for 5 min followed by the release of nitrogen gas pressure. This operation was repeated (4×). The reaction mixture was filtered through CELITE® and washed with MeOH (69.29 kg). The combined filtrates were charged through a cartridge filter into a hallar lined reactor and concentrated to 9 L under vacuum, maintaining the temperature below 60° C. Toluene (25.31 kg) was charged and the crude product was concentrated, maintaining the temperature below 60° C. This procedure was repeated (2×). Dimethyl sulfoxide (25.5 kg) was charged into the above reactor, maintaining the temperature below 70° C. and the reaction mixture was concentrated to 26.5 L under vacuum, maintaining the temperature below 70° C. The reaction mixture was cooled to rt. 1J (3.8 kg, 1.2 eq) and K$_2$CO$_3$ (7.0 kg, 3.5 eq) were charged into the above reaction mixture at ambient temperature (20-35° C.). The reaction mixture was heated to 115-120° C. for 20 h. The reaction mixture was cooled to ambient temperature (below 30° C.). Water (53.0 kg) was added into reaction mixture while maintaining the temperature below 30° C. and the reaction mixture was stirred for 30 min. EtOAc (21.0 kg) was charged and the reaction mixture was stirred for 15 min. The layers were separated. EtOAc (21.0 kg) was added to the aqueous layer and the mixture was stirred for 15 min. The layers were separated. To the combined organic layers was added 1.5 N aq. HCl (18 kg) and the mixture was stirred for 10 min. The layers were separated. To the organic layer was added 1.5 N aq. HCl (12.55 kg) and the solution was stirred for 10 min. The layers were separated. The combined acidic aqueous layers were basified to pH 8.1 from pH 0.8 by charging 10% aq. NaHCO$_3$ (16.5 kg). To the aqueous solution was added EtOAc (26.2 kg) and the solution was stirred for 10 min. The layers were separated. This procedure was repeated (2×). To the combined organic layers was added 34 wt % aq. NaCl (15 kg) and the mixture was stirred for 10 min. The layers were separated and the organic layer was dried over Na$_2$SO$_4$ (292 g), filtered through a nutsche filter, and the filtrate was charged into hallar lined reactor. The mixture was concentrated to 15 L under vacuum maintaining the temperature below 60° C. to obtain a dark brown viscous liquid. EtOAc (26.2 kg) was charged into the above reactor, maintaining the temperature below 60° C. EtOAc swapping was continued until the water content reached <1.0% by KF titration. The reaction mixture was cooled to 45-50° C. A solution of MSA (1.5 kg, 1.1 eq.) in EtOAc (14.0 kg) was added to the reaction mixture at 45-50° C. over 1 h. The reaction mixture was stirred for 20 min at 45-50° C. The reaction mixture was cooled to ambient temperature (20-35° C.) and stirred for 30 min. The reaction mixture was filtered through a pressure nutsche filter and the solid was washed with EtOAc (6.0 L) and suction dried for 20 min. The product was then dried under at 50-55° C. under vacuum for 15 h to obtain 1V (2.89 kg, 56% yield) as a pale brown solid. $^1$H NMR (400 MHz, DMSO) δ 8.08 (s, 1H), 6.42 (s, 1H), 3.87 (s, 3H), 3.64-3.43 (m, 2H), 3.22-3.09 (m, 1H), 2.92-2.78 (m, 1H), 2.59-2.51 (m, 1H), 2.44 (s, 3H), 1.95-1.83 (m, 1H), 1.66-1.42 (m, 2H), 0.94 (d, J=7.0 Hz, 3H).

1W. 5-Chloro-2-methoxy-4-((3R,4R)-3-methyl-4-(4-nitrophenoxy)piperidin-1-yl)pyridine A stirred solution of 1V (100 g, 283 mmol) in water (500 mL) and EtOAc (500 mL) was basified with 10% aq. NaHCO$_3$ to adjust the pH to ~7.5. The reaction mixture was stirred for 15 min at rt. The layers were separated and the aqueous layer was extracted with EtOAc (200 mL). The combined organic layers were washed with water (250 mL) and brine (200 mL), dried over anhydrous Na$_2$SO$_4$, and concentrated to obtain crude (3R,4R)-1-(5-chloro-2-methoxypyridin-4-yl)-3-methylpiperidin-4-ol (74 g), which was used without further purification. To a stirred solution of (3R,4R)-1-(5-chloro-2-methoxypyridin-4-yl)-3-methylpiperidin-4-ol (74 g) in THF (1.25 L) under a nitrogen atmosphere was added a 1 M solution of KOtBu in THF (595 mL, 595 mmol) dropwise at 27° C. over 15 min. A solution of 1-fluoro-4-nitrobenzene (44.0 g, 312 mmol) in THF (250 mL) was added dropwise into the reaction mixture over 15 min. The reaction mixture was stirred for 1 h at 27° C. The reaction was quenched with water (3.0 L) and the product was extracted with EtOAc (2×2.0 L). The combined organic layers were washed with brine (500 mL), dried (Na$_2$SO$_4$), and concentrated. The crude product was purified by silica chromatography to afford 1W (80.0 g, 210 mmol, 74% yield) as a yellow solid. LC-MS Anal. Calc'd for C$_{18}$H$_{20}$ClN$_3$O$_4$: 377.11, found [M+H] 378.0. $^1$H NMR (400 MHz, CDCl$_3$) δ 8.28-8.17 (m, 2H), 8.02 (s, 1H), 7.09-6.88 (m, 2H), 6.31 (s, 1H), 4.17 (td, J=8.5, 4.1 Hz, 1H), 3.92 (s, 3H), 3.56 (dq, J=12.3, 1.9 Hz, 2H), 2.96 (ddd, J=12.5, 10.1, 2.9 Hz, 1H), 2.72 (dd, J=12.4, 9.1 Hz, 1H), 2.35-2.18 (m, 2H), 1.96-1.83 (m, 1H), 1.15 (d, J=6.6 Hz, 3H).

1X. 4-((3R,4R)-1-(5-Chloro-2-methoxypyridin-4-yl)-3-methylpiperidin-4-yloxy)aniline To a suspension of 1W (6.23 g, 16.5 mmol) in MeOH (100 mL) was added NH$_4$Cl (8.82 g, 165 mmol) and water (25 mL), followed by iron powder (4.6 g, 82 mmol). The suspension was purged with a stream of nitrogen for 2 min and then vigorously stirred at 95° C. for 2 h. After cooling to rt, the reaction mixture became a thick black slurry, which was filtered via a pad of CELITE®. The pad was washed with MeOH and EtOAc and the combined filtrates were concentrated to remove most of the MeOH. The remaining aqueous phase was extracted with EtOAc (3×). The combined organic extracts were washed with water and brine, dried (Na$_2$SO$_4$), and concentrated. The obtained residue was dried under high vacuum for 2 h to afford 1× (5.73 g, 16.3 mmol, 99% yield) as a light brown foam. LC-MS Anal. Calc'd for C$_{18}$H$_{22}$ClN$_3$O$_2$: 347.14, found [M+H] 348.1. $^1$H NMR (400 MHz, CDCl$_3$) δ 7.99 (s, 1H), 6.90-6.76 (m, 2H), 6.71-6.59 (m, 2H), 6.29 (s, 1H), 4.15 (d, J=7.0 Hz, 1H), 3.91 (s, 3H), 3.81 (td, J=8.6, 4.1 Hz, 1H), 3.60-3.47 (m, 3H), 2.91-2.77 (m, 1H), 2.67-2.59 (m, 1H), 2.22-2.11 (m, 2H), 1.82 (dd, J=13.1, 2.8 Hz, 1H), 1.16 (d, J=6.8 Hz, 3H).

1Z. (R)-4-Benzyl-3-((2R,3R)-3-hydroxy-4,4-dimethoxy-2-methylbutanoyl) oxazolidin-2-one To a 1 L flask was added a 60% aq. solution of 2,2-dimethoxyacetaldehyde (250 g, 1441 mmol) and benzene (300 mL). The mixture was refluxed and water was removed by a Dean-Stark trap. 130 mL of water was removed over 3 h. After cooling under nitrogen, the benzene solution was transferred to a clean 1 L flask with 4 Å mol. sieves and diluted with anhydrous CH$_2$Cl$_2$ (300 mL) to obtain a 14.6 weight % solution of 2,2-dimethoxyacetaldehyde. $^1$H NMR (400 MHz, CDCl$_3$) δ 9.49 (d, J=1.3 Hz, 1H), 4.50 (d, J=1.5 Hz, 1H), 3.48 (s, 6H). (R)-4-Benzyl-3-propionyloxazolidin-2-one (10.0 g, 42.9 mmol) was dissolved in anhydrous CH$_2$Cl$_2$ (50.0 mL) in a dry 3-neck 500 mL flask. The solution was cooled to below −20° C. A 1 M solution of TiCl$_4$ in CH$_2$Cl$_2$ (45.0 mL, 45.0 mmol) was added slowly. After the addition, the reaction mixture was warmed to 0° C. Once the internal temperature reached 0° C., the reaction mixture was recooled to −20° C. TMEDA (9.70 mL, 64.3 mmol) was added slowly. DIPEA (7.49 mL, 42.9 mmol) was added slowly. The reaction mixture was warmed to 0° C. for 5-10 min. The dark red solution was recooled to below −40° C. A cold 14.6 weight % solution of 2,2-dimethoxyacetaldehyde (45.6 mL, 72.9 mmol) was added via addition funnel as a stream. After the addition, the internal temperature was raised to 0° C. and then carefully to 15° C. The reaction mixture was recooled to −20° C. and quenched with sat. aq. NH$_4$Cl (150 mL) and then stirred at rt for 30 min. Most of the clear CH$_2$Cl$_2$ phase separated out. The remaining solution with yellow sticky precipitates was filtered though a CELITE® pad. The filtrate was extracted with CH$_2$Cl$_2$. The CH$_2$Cl$_2$ phases were combined, washed with sat. aq. NH$_4$Cl (2×50 mL) and brine, dried (MgSO$_4$), and concentrated. Hexane (400 mL) was added and the reaction mixture was stirred for 30 min. The product crystallized out. The solid was filtered and then dissolved in a minimal amount of CH$_2$Cl$_2$ (~30 mL). Hexane (400 mL) was added while stirring to recrystallize the product. The solid was filtered to obtain 1Z (10.5 g, 31.1 mmol, 73% yield) as a white solid. LC-MS Anal. Calc'd for C$_{17}$H$_{23}$NO$_6$: 337.37, found [M-MeOH+H] 306.1. $^1$H NMR (400 MHz, CDCl$_3$) δ 7.36-7.30 (m, 2H), 7.30-7.27 (m, 1H), 7.23-7.18 (m, 2H), 4.74-4.63 (m, 1H), 4.33 (d, J=6.0 Hz, 1H), 4.23-4.14 (m, 2H), 4.07-3.95 (m, 2H), 3.42 (s, 3H), 3.38 (s, 3H), 3.27 (dd, J=13.4, 3.1 Hz, 1H), 2.78 (dd, J=13.3, 9.5 Hz, 1H), 2.55 (d, J=3.5 Hz, 1H), 1.32 (d, J=6.8 Hz, 3H).

1AA. (2R,3R)-3-Hydroxy-N,4,4-trimethoxy-N,2-dimethylbutanamide

To a suspension of N,O-dimethylhydroxylamine hydrochloride (147 g, 1510 mmol) in THF (750 mL) at −40° C. was added a 2 M solution of trimethylaluminum in toluene (756 mL, 1510 mmol). After the addition, the reaction mixture was cooled to −78° C. and a solution of 1Z (170 g, 504 mmol) in THF (750 mL) was added. The reaction mixture was warmed to 0° C. and stirred for 1 h. To a 5 L beaker with sat. aq. Rochelle's salt cooled by dry ice was added the reaction mixture in portions. After stirring for 15 min, sat. aq. NH$_4$Cl was added. The mixture was diluted with CH$_2$Cl$_2$ and the layers were separated. The aqueous layer was extracted with CH$_2$Cl$_2$. The combined organic layers were washed with brine, dried over Na$_2$SO$_4$, and concentrated. The crude product was purified by chiral SFC (Column: Luxcellulose-2 (250×30 mm, 5 μM); 70% CO$_2$, Mobile phase: 0.25% DEA in MeOH; Total flow: 100 g/min;

back pressure: 100 bar; 25° C.; Sample prep: 173 mg/mL). The product was collected and concentrated to provide 1AA (85 g, 38 mmol, 75% yield). LC-MS Anal. Calc'd for $C_9H_{19}NO_5$: 221.25, found [M-MeOH+H] 190.1. $^1$H NMR (300 MHz, CDCl$_3$) δ 4.31 (d, J=6.0 Hz, 1H), 3.94-3.85 (m, 1H), 3.70 (s, 3H), 3.43 (s, 3H), 3.40 (s, 3H), 3.23 (d, J=2.6 Hz, 1H), 3.18 (s, 3H), 3.15-3.04 (m, 1H), 1.22 (d, J=6.8 Hz, 3H).

1BB. (2R,3R)—N,4,4-Trimethoxy-3-(3-methoxypropoxy)-N,2-dimethylbutanamide

To a 5 L round bottom flask was added 1AA (104 g, 470 mmol), THF (800 mL), 3-methoxypropyl methanesulfonate (158 g, 940 mmol), THF (200 mL), and a 1 M solution of TBAF in THF (705 mL, 705 mmol). The solution was cooled to 0° C. and then 60% NaH (75.0 g, 1800 mmol) was added portionwise. After the addition was complete, the reaction mixture was stirred for 1 h, holding the temperature below 20° C. The mixture was poured into 5 L beaker containing ice/water. Sat. aq. NH$_4$Cl was added until the pH ~8. The product was extracted with EtOAc and CH$_2$Cl$_2$ (3×250 mL). The combined organic layers were dried over Na$_2$SO$_4$ and concentrated. The crude product was purified by silica chromatography to give 1BB (125 g, 426 mmol, 91% yield) as a red oil. LC-MS Anal. Calc'd for $C_{13}H_{27}NO_6$: 293.36, found [M-MeOH+H]262.1. $^1$H NMR (400 MHz, CDCl$_3$) δ 4.24 (d, J=4.8 Hz, 1H), 3.82 (dt, J=9.1, 6.2 Hz, 1H), 3.68 (s, 3H), 3.66-3.56 (m, 2H), 3.47 (t, J=6.4 Hz, 2H), 3.40 (s, 3H), 3.38 (s, 3H), 3.32 (s, 3H), 3.17 (s, 3H), 3.15-3.07 (m, 1H), 1.92-1.75 (m, 2H), 1.20 (d, J=7.0 Hz, 3H).

1CC. (2R,3R)-4,4-Dimethoxy-3-(3-methoxypropoxy)-2-methylbutanal

To a solution of 1BB (240 g, 818 mmol) in THF (2500 mL) was added a 1 M solution of DIBAL-H in THF (1227 mL, 1227 mmol) over 10 min at −78° C. The reaction mixture was stirred for 2 h. A 0° C. solution of sat. aq. Rochelle's salt was added to the reaction mixture. The reaction mixture was extracted with EtOAc. The combined organic layers were washed with brine, dried over Na$_2$SO$_4$, and concentrated to provide 1CC (170 g, 726 mmol, 89% yield), which was used without further purification. $^1$H NMR (400 MHz, CDCl$_3$) δ 9.78-9.51 (m, 1H), 4.29 (d, J=5.9 Hz, 1H), 3.81-3.75 (m, 1H), 3.72 (dd, J=6.1, 4.7 Hz, 1H), 3.55-3.48 (m, 2H), 3.46 (s, 3H), 3.40 (s, 3H), 3.41 (t, J=6.3 Hz, 1H), 3.31 (s, 3H), 2.67-2.57 (m, 1H), 1.84-1.74 (m, 2H), 1.14 (d, J=7.0 Hz, 3H). 1DD. (3S,4R)-1,1-Dibromo-5,5-dimethoxy-4-(3-methoxypropoxy)-3-methylpent-1-ene: To a solution of CBr$_4$ (299 g, 901 mmol) in CH$_2$Cl$_2$ (2000 mL) at 0° C. was added Ph$_3$P (472 g, 1800 mmol) in portions. The solution was stirred at 0° C. for 10 min and then a solution of 1CC (176 g, 751 mmol) in CH$_2$Cl$_2$ (1000 mL) was added dropwise. The solution was vigorously stirred at 0° C. for 1 h. The excess dibromophosphorane was quenched by the sequential addition of Et$_3$N (253 mL, 1800 mmol) followed by MeOH (76 mL, 1900 mmol) and the solution was stirred at rt. The solution was then added to a solution of 5:1 hexane:Et$_2$O (1800 mL), resulting in the precipitation of the triphenylphosphine oxide. The light brown solid was removed by filtration and washed with hexane (750 mL). The filtrate was evaporated and purified by silica chromatography to give 1DD (212 g, 543 mmol, 72% yield) as a red oil. $^1$H NMR (400 MHz, CDCl$_3$) δ 6.39 (d, J=9.7 Hz, 1H), 4.22 (d, J=6.4 Hz, 1H), 3.82 (dt, J=9.2, 5.9 Hz, 1H), 3.45 (s, 3H), 3.55-3.43 (m, 3H), 3.39 (s, 3H), 3.34 (s, 3H), 3.22 (dd, J=6.4, 4.2 Hz, 1H), 2.75 (dqd, J=9.6, 6.8, 4.2 Hz, 1H), 1.89-1.75 (m, 2H), 1.03 (d, J=6.8 Hz, 3H). $^{13}$C NMR (126 MHz, CDCl$_3$) δ 141.5, 105.6, 87.7, 81.0, 69.5, 69.5, 58.6, 55.7, 54.1, 39.8, 30.4, 13.2.

1EE. (4S,5R)-Ethyl 6,6-dimethoxy-5-(3-methoxypropoxy)-4-methylhex-2-ynoate

To a solution of 1DD (212 g, 543 mmol) in THF (2000 mL) at −78° C. was added a solution of 2.5 M solution of n-BuLi in hexanes (456 mL, 1141 mmol). The reaction mixture was stirred at −78° C. for 30 min and then ethyl chloroformate (110 mL, 1140 mmol) was added. The reaction mixture was warmed to rt and stirred for 1 h. The reaction mixture was quenched with sat. aq. NH$_4$Cl and extracted with EtOAc. The combined organic layers were washed with brine, dried over Na$_2$SO$_4$, and concentrated. The crude product was purified by silica chromatography to provide 1EE (142 g, 446 mmol, 82% yield) as a colorless oil. $^1$H NMR (400 MHz, CDCl$_3$) δ 4.31 (d, J=5.5 Hz, 1H), 4.20 (q, J=7.3 Hz, 2H), 3.86-3.76 (m, 1H), 3.69 (dt, J=9.4, 6.3 Hz, 1H), 3.46 (s, 3H), 3.49-3.43 (m, 2H), 3.39 (s, 3H), 3.41-3.37 (m, 1H), 3.31 (s, 3H), 2.88 (qd, J=7.0, 4.6 Hz, 1H), 1.89-1.79 (m, 2H), 1.29 (t, J=7.1 Hz, 3H), 1.23 (d, J=7.0 Hz, 3H). $^{13}$C NMR (126 MHz, CDCl$_3$) δ 153.7, 105.2, 91.0, 81.2, 73.8, 69.8, 69.6, 61.7, 58.5, 55.9, 55.0, 30.3, 27.7, 14.6, 14.0.

1FF. (4S,5R,Z)-Ethyl 6,6-dimethoxy-5-(3-methoxypropoxy)-4-methylhex-2-enoate To a solution of 1EE (53.0 g, 175 mmol) in THF (500 mL) and pyridine (42.5 mL, 526 mmol) was added Lindlar Catalyst (44.8 g, 21.0 mmol). The reaction mixture was degassed and stirred at rt under H$_2$ (1 atm) for 8 h. The reaction mixture was filtered though CELITE® and concentrated. The crude material was purified by silica chromatography to provide 1FF (45.5 g, 148 mmol, 84% yield) as a colorless oil. $^1$H NMR (300 MHz, CDCl$_3$) δ 6.18 (dd, J=11.7, 10.2 Hz, 1H), 5.71 (dd, J=11.7, 1.1 Hz, 1H), 4.24 (d, J=6.8 Hz, 1H), 4.15 (q, J=7.1 Hz, 2H), 3.84-3.69 (m, 2H), 3.52-3.44 (m, 3H), 3.43 (s, 3H), 3.37 (s, 3H), 3.32 (s, 3H), 3.22 (dd, J=6.8, 4.2 Hz, 1H), 1.86-1.75 (m, 2H), 1.27 (t, J=7.2 Hz, 3H), 1.03 (d, J=6.8 Hz, 3H). $^{13}$C NMR (101 MHz, CHLOROFORM-d) δ 166.2, 152.6, 118.3, 105.9, 82.1, 77.2, 69.7, 69.5, 59.8, 58.5, 55.5, 53.9, 34.3, 30.5, 14.2.

1GG. (4S,5R,Z)-Ethyl 5-(3-methoxypropoxy)-4-methyl-6-oxohex-2-enoate

To a solution of 1FF (9.91 g, 32.6 mmol) in THF (65 mL) was added 1 N aq. HCl (67.8 mL, 67.8 mmol). The reaction mixture was heated to 50° C. overnight. The reaction mixture was cooled to rt and diluted with EtOAc. The layers were separated. The aqueous layer was extracted with EtOAc. The combined organic extracts were washed with brine, dried (MgSO$_4$), and concentrated to give 1GG (8.41 g, 32.6 mmol, 100% yield) as a colorless oil, which was used without further purification. LC-MS Anal. Calc'd for $C_{13}H_{22}O_5$: 258.31, found [M+H] 259.0. $^1$H NMR (500 MHz, CDCl$_3$) δ 9.64 (d, J=1.9 Hz, 1H), 6.12 (dd, J=11.4, 10.0 Hz, 1H), 5.80 (dd, J=11.4, 1.0 Hz, 1H), 4.17 (q, J=7.0 Hz, 2H), 4.05-3.92 (m, 1H), 3.69 (dt, J=9.3, 6.1 Hz, 1H), 3.58 (dd, J=5.6, 2.1 Hz, 1H), 3.54-3.44 (m, 3H), 3.33 (s, 3H), 1.92-1.82 (m, 2H), 1.29 (t, J=7.2 Hz, 3H), 1.08 (d, J=6.9 Hz, 3H). $^{13}$C NMR (101 MHz, CDCl$_3$) δ 202.9, 165.9, 149.6, 120.3, 87.4, 69.3, 68.3, 60.1, 58.6, 34.0, 30.1, 15.1, 14.2.

1HH. Ethyl 2-((2S,3S,4R)-1-(4-(((3R,4R)-1-(5-chloro-2-methoxypyridin-4-yl)-3-methylpiperidin-4-yl)oxy)phenyl)-4-(3-methoxypropoxy)-3-methylpyrrolidin-2-yl)acetate To a solution of NaBH(OAc)$_3$ (11.0 g, 51.9 mmol) and 1× (12.0 g, 34.6 mmol) in CH$_2$Cl$_2$ (176 mL) vigorously stirring at rt was added a solution of 1GG (9.11 g, 35.3 mmol) in CH$_2$Cl$_2$ (88 mL) dropwise over 50 min. The reaction mixture was stirred at rt for 20 min. The reaction mixture was cooled to 0° C. and 1.5 M aq. K$_2$HPO$_4$ (150 mL) was added dropwise via addition funnel. The reaction mixture was stirred at rt for 15 min and extracted with CH$_2$Cl$_2$ (3×). The combined CH$_2$Cl$_2$ extracts were washed with brine, dried (MgSO$_4$), and concentrated to give the resulting crude product (4S,5R,Z)-ethyl 6-((4-(((3R,4R)-1-(5-chloro-2-methoxypyridin-4-yl)-3-methylpiperidin-4-yl)oxy)phenyl)amino)-5-(3-methoxypropoxy)-4-methylhex-2-enoate as a dark brown oil, which was used directly in the next step. To a solution of (4S,5R,Z)-ethyl 6-((4-(((3R,4R)-1-(5-chloro-2-methoxypyridin-4-yl)-3-methylpiperidin-4-yl)oxy)phenyl)amino)-5-(3-methoxypropoxy)-4-methylhex-2-enoate in THF (346 mL) at rt was added NaOtBu (3.66 g, 38.0 mmol) in several portions. After the addition, the reaction mixture was stirred at rt for 5 min. The reaction mixture was quenched with sat. aq. NH$_4$Cl. The product was extracted with EtOAc (3×). The combined organic layers were washed with brine, dried (Na$_2$SO$_4$), and concentrated. The crude product was purified by silica chromatography to afford ethyl 2-((2S,3S,4R)-1-(4-(((3R,4R)-1-(5-chloro-2-methoxypyridin-4-yl)-3-methylpiperidin-4-yl)oxy)phenyl)-4-(3-methoxypropoxy)-3-methylpyrrolidin-2-yl)acetate (14.9 g, 25.2 mmol, 73% yield) as a yellow oil. 137 g (232 mmol) of the material was further purified by chiral SFC (Lux Cellulose-4 column (3×25 cm, 5 µM); 100 bars; 50° C.; 160 mL/min; Mobile Phase: CO$_2$/MeOH (67/33); Detector Wavelength: 220 nM; Separation Program: sequence injection; Injection: 3.0 mL with cycle time 4.55 min; Sample preparation: 137 g/900 mL 3:1 MeOH:CH$_2$Cl$_2$ (15.2 mg/mL)) to provide ethyl 2-((2S,3S,4R)-1-(4-(((3R,4R)-1-(5-chloro-2-methoxypyridin-4-yl)-3-methylpiperidin-4-yl)oxy)phenyl)-4-(3-methoxypropoxy)-3-methylpyrrolidin-2-yl)acetate (120 g, 203 mmol, 88% yield) as a light orange oil. The material was repurified by silica chromatography to obtain quantitative yield of 1HH (120 g) as a light yellow oil. LC-MS Anal. Calc'd for C$_{31}$H$_{44}$ClN$_3$O$_6$: 589.29, found [M+H] 590.1. $^1$H NMR (400 MHz, CDCl$_3$) δ 7.96 (s, 1H), 6.88 (d, J=9.0 Hz, 2H), 6.51 (d, J=9.0 Hz, 2H), 6.26 (s, 1H), 4.17 (q, J=7.2 Hz, 2H), 3.88 (s, 3H), 3.80-3.73 (m, 2H), 3.72-3.68 (m, 1H), 3.61-3.55 (m, 3H), 3.55-3.48 (m, 3H), 3.48-3.39 (m, 4H), 3.36-3.28 (m, 3H), 2.86-2.73 (m, 2H), 2.73-2.55 (m, 2H), 2.36 (q, J=7.1 Hz, 1H), 2.21-2.05 (m, 2H), 1.88-1.73 (m, 3H), 1.28 (t, J=7.0 Hz, 3H), 1.14 (d, J=6.6 Hz, 3H), 1.00 (d, J=7.3 Hz, 3H). $^{13}$C NMR (101 MHz, CDCl$_3$) δ 172.6, 164.1, 157.6, 148.8, 146.6, 141.8, 118.8, 118.2, 112.5, 100.4, 84.7, 80.9, 69.6, 65.9, 62.3, 60.3, 58.6, 55.0, 53.6, 52.9, 48.3, 43.3, 37.2, 36.1, 30.1, 29.8, 18.6, 15.7, 14.3.

Example 1

To a stirred solution of 1HH (21.5 g, 36.4 mmol) in degassed THF (260 mL), IPA (52 mL), and water (52 mL) at 0° C. was added 1 M aq. LiOH (109 mL, 109 mmol) dropwise. The reaction mixture was warmed to rt slowly and stirred for 16 h. The reaction mixture was partitioned between water (500 mL) and hexane (600 mL) and the layers were separated. The aqueous layer was cooled to 0° C. and then acidified by addition of 1 M aq. HCl dropwise until pH ~4-5 with stirring. The product was extracted with CH$_2$Cl$_2$ (3×250 mL). The combined organic extracts were dried (MgSO$_4$), concentrated by rotary evaporation at rt, and then dried under high vacuum for 16 h while protecting from light to afford Example 1 (20.5 g, 36.5 mmol, 100% yield) as an off-white foam. LC-MS Anal. Calc'd for C$_{29}$H$_{40}$ClN$_3$O$_6$: 561.26, found [M+H] 562.2. $^1$H NMR (400 MHz, CDCl$_3$) δ 7.97 (s, 1H), 6.90 (d, J=9.0 Hz, 2H), 6.58 (d, J=9.0 Hz, 2H), 6.26 (s, 1H), 3.88 (s, 3H), 3.79 (td, J=8.7, 4.0 Hz, 1H), 3.76-3.69 (m, 2H), 3.63-3.41 (m, 8H), 3.34 (s, 3H), 2.89-2.70 (m, 3H), 2.62 (dd, J=12.1, 9.2 Hz, 1H), 2.40 (q, J=7.1 Hz, 1H), 2.22-2.06 (m, 2H), 1.89-1.75 (m, 3H), 1.14 (d, J=6.8 Hz, 3H), 1.04 (d, J=7.3 Hz, 3H). $^{13}$C NMR (126 MHz, DMSO-d$_6$) δ 173.2, 163.7, 157.2, 148.4, 146.3, 141.6, 118.3, 117.2, 112.3, 100.3, 83.8, 79.7, 68.9, 65.3, 62.2, 57.8, 54.2, 53.3, 52.6, 47.8, 42.8, 37.0, 36.0, 29.7, 29.6, 18.4, 15.3.

Example 1, MSA Salt

Example 1 (28.8 g, 51.2 mmol) was dissolved in CH$_3$CN (256 mL). The solution was cooled to 0° C. and MSA (4.92 g, 51.2 mmol) was added dropwise. After the addition, the solution was concentrated. The resulting residue was dissolved in CH$_2$Cl$_2$ (60 mL) and hexanes was added dropwise (~240 mL). A gummy solid was formed and the solution was decanted. The gummy solid was concentrated and dried under high vacuum with protection from light to obtain Example 1, MSA salt (33.0 g, 50.1 mmol, 98% yield) as a light beige solid. LC-MS Anal. Calc'd for C$_{29}$H$_{40}$ClN$_3$O$_6$: 561.26, found [M+H] 562.2. $^1$H NMR (500 MHz, CH$_3$CN-d$_3$) δ 8.04 (s, 1H), 7.17 (br d, J=8.0 Hz, 2H), 7.01 (d, J=9.1 Hz, 2H), 6.40 (s, 1H), 4.13-4.06 (m, 1H), 3.94 (s, 3H), 3.92-3.87 (m, 1H), 3.82-3.75 (m, 1H), 3.75-3.66 (m, 3H), 3.66-3.60 (m, 1H), 3.53 (td, J=6.4, 1.2 Hz, 2H), 3.43 (t, J=6.3 Hz, 2H), 3.27 (s, 3H), 3.10 (ddd, J=13.0, 10.5, 2.9 Hz, 1H), 2.88 (dd, J=12.9, 9.6 Hz, 1H), 2.82-2.74 (m, 1H), 2.73-2.65 (m, 1H), 2.63 (s, 3H), 2.38-2.31 (m, 1H), 2.25-2.16 (m, 1H), 2.11-2.01 (m, 1H), 1.78 (quin, J=6.3 Hz, 2H), 1.75-1.66 (m, 1H), 1.13 (d, J=7.2 Hz, 3H), 1.08 (d, J=6.9 Hz, 3H). $^{13}$C NMR (126 MHz, 120° C., DMSO-d$_6$) δ 172.1, 163.4, 156.8, 148.9, 145.6, 140.8, 135.6, 117.9, 116.5, 113.0, 99.4, 83.4, 79.5, 68.6, 65.3, 62.4, 57.2, 53.7, 53.0, 52.9, 47.2, 43.0, 36.4, 35.5, 29.3, 29.2, 17.5, 14.6.

Example 2

2-((2S,3S,4R)-1-(6-(((3,4-trans)-1-(5-Chloro-2-methoxypyridin-4-yl)-3-methylpiperidin-4-yl)oxy)pyridin-3-yl)-4-(3-methoxypropoxy)-3-methylpyrrolidin-2-yl)acetic acid, HCl

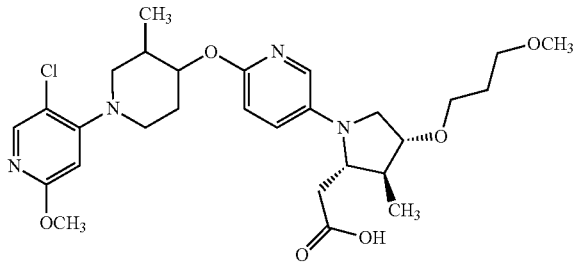 [SMILES: COCCCO[C@H]1CN(c2ccc(OC3CCN(c4cc(OC)ncc4Cl)CC3C)nc2)[C@@H](CC(=O)O)[C@@H]1C]

2A. 5-Chloro-4-((3,4-trans)-4-((5-iodopyridin-2-yl)oxy)-3-methylpiperidin-1-yl)-2-methoxypyridine To a solution of 1P, Isomer 1 (494 mg, 1.92 mmol) and 5-iodopyridin-2-ol (340 mg, 1.54 mmol) in toluene (8 mL) was added Bu$_3$P (0.58 mL, 2.3 mmol). ADDP (582 mg, 2.31 mmol) was added in three portions to the reaction mixture over 11 min and the reaction mixture became a thick slurry. The reaction mixture was sonicated for 1 h, stirred at 60° C. for 2 h, and then stirred at rt for 16 h. The reaction mixture was treated with hexanes (50 mL). After stirring for 5 min, the mixture was filtered and concentrated. The residue was purified by silica chromatography to provide 2A (534 mg, 1.05 mmol, 68% yield) as a white solid. LC-MS Anal. Calc'd for C$_{17}$H$_{19}$ClIN$_3$O$_2$: 459.71, found [M+H] 460.1, 461.9. $^1$H NMR (400 MHz, CDCl$_3$) δ 8.29 (dd, J=2.4, 0.7 Hz, 1H), 7.96 (s, 1H), 7.77 (dd, J=8.8, 2.4 Hz, 1H), 6.58 (dd, J=8.7, 0.6 Hz, 1H), 6.26 (s, 1H), 4.82 (td, J=9.3, 4.3 Hz, 1H), 3.88 (s, 3H), 3.60-3.46 (m, 2H), 2.99-2.84 (m, 1H), 2.61 (dd, J=12.3, 9.7 Hz, 1H), 2.33-2.22 (m, 1H), 2.20-2.07 (m, 1H), 1.84-1.73 (m, 1H), 1.02 (d, J=6.6 Hz, 3H).

2B. 2-((2S,3S,4R)-1-(6-(((3,4-trans)-1-(5-Chloro-2-methoxypyridin-4-yl)-3-methylpiperidin-4-yl)oxy)pyridin-3-yl)-4-(3-methoxypropoxy)-3-methylpyrrolidin-2-yl)acetonitrile 2B was prepared from 2A following the procedure of Example 1. LC-MS Anal. Calc'd for C$_{28}$H$_{38}$ClN$_5$O$_4$: 544.09, found [M+] 544.2. $^1$H NMR (400 MHz, CDCl$_3$) δ 7.97 (s, 1H), 7.47 (d, J=2.9 Hz, 1H), 6.94 (dd, J=9.0, 3.1 Hz, 1H), 6.70 (d, J=8.8 Hz, 1H), 6.28 (s, 1H), 4.73 (td, J=9.3, 4.3 Hz, 1H), 3.89 (s, 3H), 3.77 (d, J=2.0 Hz, 1H), 3.65 (dd, J=9.1, 3.6 Hz, 1H), 3.62-3.50 (m, 4H), 3.49-3.40 (m, 4H), 3.33 (s, 3H), 2.99-2.88 (m, 1H), 2.87-2.77 (m, 1H), 2.76-2.67 (m, 1H), 2.66-2.51 (m, 2H), 2.35-2.24 (m, 1H), 2.20-2.07 (m, 1H), 1.89-1.71 (m, 3H), 1.06 (d, J=3.5 Hz, 3H), 1.04 (d, J=2.9 Hz, 3H).

Example 2

To a solution of 2B (33 mg, 0.061 mmol) in EtOH (0.5 mL) was added 6 M aq. KOH (0.20 mL, 1.2 mmol). The reaction mixture was heated in a sealed microwave vial to 125° C. for 5 h and then cooled to rt. The reaction mixture was concentrated, acidified with 1 N aq. HCl, and extracted with CH$_2$Cl$_2$. The combined organic layers were washed with water and brine, dried (Na$_2$SO$_4$), and concentrated. The crude product was purified by RP-Prep. HPLC and the fractions containing product were lyophilized. The product was treated with CH$_3$CN (0.5 mL) and 3 N aq. HCl (0.5 mL) and concentrated. The procedure was repeated (2×) to yield Example 2 (11 mg, 0.018 mmol, 29% yield) as a green powder. LC-MS Anal. Calc'd for C$_{28}$H$_{39}$ClN$_4$O$_6$: 562.2, found [M+H] 563.2. $^1$H NMR (400 MHz, DMSO-d$_6$) δ 8.03 (s, 1H), 7.55-7.35 (m, 1H), 7.25-7.04 (m, 1H), 6.95-6.76 (m, 1H), 6.43 (s, 1H), 4.73-4.61 (m, 1H), 3.82 (s, 3H), 3.79-3.71 (m, 1H), 3.66-3.57 (m, 1H), 3.55-3.30 (m, 8H), 3.21 (s, 3H), 2.99-2.84 (m, 1H), 2.74-2.64 (m, 1H), 2.63-2.53 (m, 2H), 2.39-3.24 (m, 1H), 2.22-2.12 (m, 1H), 2.04-1.86 (m, 1H), 1.73 (s, 2H), 1.67-1.50 (m, 1H), 0.96 (dd, J=17.3, 6.9 Hz, 6H). Analytical HPLC: RT=8.15 min, HI: 95.7%. hGPR40 EC$_{50}$=180 nM. hGPR40 IP1 EC$_{50}$=27 nM.

Example 3

2-((2S,3S,4R)-1-(4-((1-(5-Ethoxy-2-fluorophenyl)piperidin-4-yl)oxy)phenyl)-4-(3-methoxypropoxy)-3-methylpyrrolidin-2-yl)acetic acid, HCl

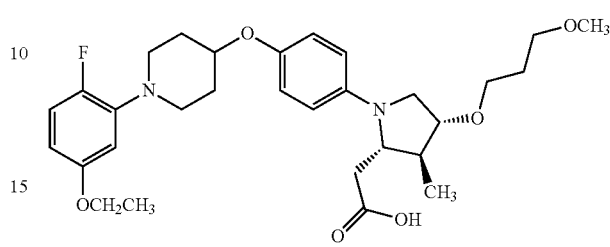

3A. 1-(5-Ethoxy-2-fluorophenyl)piperidin-4-ol

A mixture of 4-ethoxy-1,2-difluorobenzene (17.5 mL, 126 mmol), piperidin-4-ol (39.2 g, 379 mmol), DMSO (42 mL), and pyridine (21.1 mL) in a flask equipped with a reflux condenser under nitrogen was heated to 140° C. for 48 h. The reaction mixture was cooled to rt, diluted with 4/1 hexanes/EtOAc, and washed with 2% aq. NaHCO$_3$, water, and brine. The organic layer was dried (MgSO$_4$) and concentrated. The crude product was purified by silica chromatography to provide 3A (10.6 g, 44.2 mmol, 35% yield) as a yellow oil. LC-MS Anal. Calc'd for C$_{13}$H$_{18}$FNO$_2$: 239.29, found [M+H] 240.1. $^1$H NMR (400 MHz, CDCl$_3$) δ 6.90 (dd, J=12.3, 8.8 Hz, 1H), 6.51 (dd, J=7.4, 3.0 Hz, 1H), 6.39 (dt, J=8.8, 3.2 Hz, 1H), 3.97 (q, J=7.0 Hz, 2H), 3.89-3.78 (m, 1H), 3.41-3.30 (m, 2H), 2.82 (ddd, J=12.2, 9.5, 3.0 Hz, 2H), 2.04-1.95 (m, 2H), 1.74 (dtd, J=12.9, 9.2, 3.7 Hz, 2H), 1.53-1.46 (m, 1H), 1.39 (t, J=6.9 Hz, 3H).

3B. 1-(5-Ethoxy-2-fluorophenyl)piperidin-4-yl 4-methylbenzenesulfonate

To a solution of 3A (10.4 g, 43.4 mmol) and 4-methylbenzene-1-sulfonyl chloride (12.4 g, 65.1 mmol) in CH$_2$Cl$_2$ (108 mL), was added pyridine (35.1 mL, 434 mmol) dropwise. The reaction mixture was stirred at rt overnight. The reaction mixture was diluted with EtOAc, washed with water and brine, dried (MgSO$_4$), and concentrated. The crude product was purified by silica chromatography to provide 3B (13.4 g, 34.1 mmol, 79% yield) as a colorless oil. LC-MS Anal. Calc'd for C$_{20}$H$_{24}$FNO$_4$S: 393.47, found [M+H]394.1. $^1$H NMR (400 MHz, CDCl$_3$) δ 7.86-7.78 (m, 2H), 7.39-7.31 (m, 2H), 6.88 (dd, J=12.1, 8.8 Hz, 1H), 6.46 (dd, J=7.4, 3.0 Hz, 1H), 6.39 (dt, J=8.9, 3.2 Hz, 1H), 4.69 (tt, J=7.4, 3.8 Hz, 1H), 3.96 (q, J=6.9 Hz, 2H), 3.22 (ddd, J=11.8, 7.3, 4.0 Hz, 2H), 2.90 (ddd, J=11.8, 7.6, 3.9 Hz, 2H), 2.46 (s, 3H), 2.03-1.86 (m, 4H), 1.38 (t, J=6.9 Hz, 3H).

3C. 1-(5-Ethoxy-2-fluorophenyl)-4-(4-iodophenoxy)piperidine

A solution of 4-iodophenol (5.62 g, 25.6 mmol), 3B (6.704 g, 17.04 mmol), and Cs$_2$CO$_3$ (16.7 g, 51.1 mmol) in anhydrous DMF (43 mL) was heated to 55° C. for 16 h. The reaction mixture was diluted with EtOAc and water and extracted with EtOAc (3×). The combined organic layers were washed with water, dried (MgSO$_4$), and concentrated. The crude product was purified by silica chromatography to provide 3C (3.99 g, 9.04 mmol, 53% yield) as a white solid. LC-MS Anal. Calc'd for $C_{19}H_{21}FINO_2$: 441.28, found [M+H]442.0. $^1$H NMR (400 MHz, CDCl$_3$) δ 7.61-7.51 (m, 2H), 6.91 (dd, J=12.1, 8.8 Hz, 1H), 6.76-6.67 (m, 2H), 6.53 (dd, J=7.4, 3.0 Hz, 1H), 6.40 (dt, J=8.8, 3.2 Hz, 1H), 4.42 (tt, J=7.2, 3.6 Hz, 1H), 3.98 (q, J=6.9 Hz, 2H), 3.31 (ddd, J=11.6, 7.8, 3.5 Hz, 2H), 2.98 (ddd, J=11.8, 8.0, 3.5 Hz, 2H), 2.17-2.05 (m, 2H), 2.02-1.90 (m, 2H), 1.39 (t, J=6.9 Hz, 3H).

Example 3 (green powder, 13 mg) was prepared from 3C following the procedure of Example 1. LC-MS Anal. Calc'd for $C_{30}H_{41}FN_2O_6$: 544.3, found [M+H] 545.3. $^1$H NMR (400 MHz, DMSO-d$_6$) δ 7.01 (dd, J=12.5, 8.8 Hz, 1H), 6.90 (d, J=8.8 Hz, 2H), 6.60-6.42 (m, 4H), 4.30 (br. s., 1H), 3.97 (q, J=7.0 Hz, 2H), 3.74 (d, J=4.0 Hz, 1H), 3.62 (d, J=9.5 Hz, 1H), 3.54-3.40 (m, 3H), 3.37 (t, J=6.3 Hz, 2H), 3.30-3.22 (m, 2H), 3.21 (s, 3H), 2.90 (t, J=8.8 Hz, 2H), 2.70-2.57 (m, 1H), 2.27 (d, J=7.0 Hz, 1H), 2.27-2.20 (m, 1H), 2.27-2.20 (m, 1H), 2.07-1.93 (m, 2H), 1.80-1.66 (m, 4H), 1.30 (t, J=6.9 Hz, 3H), 0.95 (d, J=7.0 Hz, 3H). Analytical HPLC: RT=10.0 min, HI: 94.8%. hGPR40 EC$_{50}$=200 nM.

Example 4

2-((2S,3S,4R)-1-(4-((1-(5-Chloro-2-methoxypyridin-4-yl)piperidin-4-yl)oxy)phenyl)-4-(3-methoxypropoxy)-3-methylpyrrolidin-2-yl)acetic acid

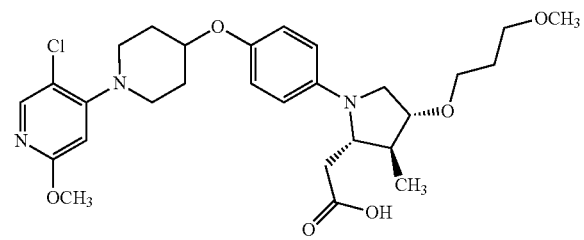 [SMILES: COCCCO[C@H]1CN(c2ccc(OC3CCN(c4cc(OC)ncc4Cl)CC3)cc2)[C@@H](CC(=O)O)[C@@H]1C]

4A.
1-(5-Chloro-2-methoxypyridin-4-yl)piperidin-4-ol

A solution of 1J (2.80 g, 12.6 mmol), piperidin-4-ol (1.40 g, 13.8 mmol), and K$_2$CO$_3$ (8.70 g, 62.9 mmol) in DMSO (30 mL) was stirred at 110° C. for 14 h. The reaction mixture was partitioned between water (150 mL) and EtOAc (150 mL). The organic layer was separated, washed with water (2×100 mL) and brine (100 mL), dried over MgSO$_4$, filtered, and concentrated. The residue was purified by silica chromatography to give 4A (2.70 g, 11.1 mmol, 88% yield) as a colorless oil. LC-MS Anal. Calc'd for $C_{11}H_{15}ClN_2O_2$: 242.70 found [M+H] 243.0. $^1$H NMR (400 MHz, CDCl$_3$) δ 7.97 (s, 1H), 6.27 (s, 1H), 3.94-3.84 (m, 4H), 3.51-3.37 (m, 2H), 2.90 (ddd, J=12.3, 9.2, 3.0 Hz, 2H), 2.07-1.95 (m, 2H), 1.84-1.66 (m, 2H).

Example 4 (white powder, 28 mg) was prepared from 4A following the procedure of Example 1. LC-MS Anal. Calc'd for $C_{28}H_{38}ClN_3O_6$: 547.2, found [M+H] 548.2. $^1$H NMR (400 MHz, CD$_3$CN) δ 7.96 (s, 1H), 6.87 (d, J=9.0 Hz, 2H), 6.54 (d, J=9.0 Hz, 2H), 6.35 (s, 1H), 4.48-4.14 (m, 1H), 3.82 (s, 3H), 3.75-3.70 (m, 1H), 3.68-3.61 (m, 1H), 3.57-3.43 (m, 2H), 3.40 (t, J=6.3 Hz, 4H), 3.24 (s, 3H), 3.07-2.90 (m, 2H), 2.73-2.51 (m, 2H), 2.37-2.24 (m, 1H), 2.20-1.98 (m, 4H), 1.76 (t, J=6.3 Hz, 4H), 0.96 (d, J=7.3 Hz, 3H). Analytical HPLC: RT=9.26 min, HI: 98.2%. hGPR40 EC$_{50}$=73 nM. hGPR40 IP1 EC$_{50}$=13 nM.

Example 5

2-((2S,3S,4R)-1-(6-((1-(5-Ethoxy-2-fluorophenyl)piperidin-4-yl)oxy)pyridin-3-yl)-4-(3-methoxypropoxy)-3-methylpyrrolidin-2-yl)acetic acid

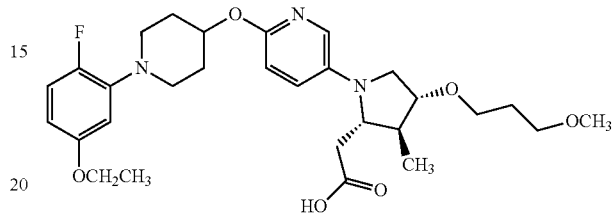

Example 5 (beige solid, 59 mg) was prepared from 3A and 5-iodopyridin-2-ol following the procedure of Example 2. LC-MS Anal. Calc'd for $C_{29}H_{40}FN_3O_6$: 545.64, found [M+H] 546.3. $^1$H NMR (400 MHz, CD$_3$CN) δ 7.48 (d, J=3.1 Hz, 1H), 7.04 (dd, J=8.9, 3.2 Hz, 1H), 6.93 (dd, J=12.4, 8.9 Hz, 1H), 6.64 (d, J=8.8 Hz, 1H), 6.54 (dd, J=7.4, 3.0 Hz, 1H), 6.42 (dt, J=8.9, 3.2 Hz, 1H), 4.97 (tt, J=8.2, 4.0 Hz, 1H), 3.97 (q, J=6.9 Hz, 2H), 3.77-3.72 (m, 1H), 3.71-3.64 (m, 1H), 3.57-3.44 (m, 2H), 3.43-3.35 (m, 4H), 3.34-3.26 (m, 2H), 3.25 (s, 3H), 2.92 (ddd, J=12.0, 9.1, 3.1 Hz, 2H), 2.75-2.58 (m, 2H), 2.34 (q, J=7.1 Hz, 1H), 2.15-2.02 (m, 2H), 1.88-1.70 (m, 4H), 1.32 (t, J=7.0 Hz, 3H), 0.97 (d, J=7.3 Hz, 3H). Analytical HPLC: RT=8.1 min, HI: 99.1%. hGPR40 EC$_{50}$=170 nM.

Example 6

2-((2S,3S,4R)-1-(6-((1-(5-Chloro-2-methoxypyridin-4-yl)piperidin-4-yl)oxy)pyridin-3-yl)-4-(3-methoxypropoxy)-3-methylpyrrolidin-2-yl)acetic acid

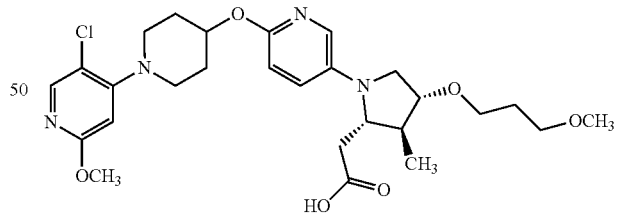

Example 6 was prepared from 4A and 5-iodopyridin-2-ol following the procedure of Example 2 to yield Example 6 (white solid, 21 mg). LC-MS Anal. Calc'd for $C_{27}H_{37}ClN_4O_6$: 549.06, found [M+H] 549.2. $^1$H NMR (400 MHz, CD$_3$CN) δ 7.96 (s, 1H), 7.48 (d, J=3.1 Hz, 1H), 7.04 (dd, J=9.0, 3.1 Hz, 1H), 6.64 (d, J=8.8 Hz, 1H), 6.35 (s, 1H), 5.04 (tt, J=7.8, 3.9 Hz, 1H), 3.83 (s, 3H), 3.75 (dt, J=4.6, 1.7 Hz, 1H), 3.68 (ddd, J=9.1, 4.0, 1.2 Hz, 1H), 3.58-3.46 (m, 2H), 3.46-3.34 (m, 6H), 3.25 (s, 3H), 3.04 (ddd, J=12.2, 8.7, 3.1 Hz, 2H), 2.75-2.59 (m, 2H), 2.34 (q, J=7.3 Hz, 1H), 2.15-2.04 (m, 2H), 1.89-1.80 (m, 2H), 1.77 (quin, J=6.3 Hz, 2H), 0.97 (d, J=7.3 Hz, 3H). Analytical HPLC: RT=7.2 min, HI: 97.9%. hGPR40 EC$_{50}$=200 nM. hGPR40 IP1 EC$_{50}$=19 nM.

Example 7

2-((2S,3S,4R)-1-(4-(((3,4-trans)-1-(5-Chloro-2-methoxypyridin-4-yl)-3-methylpiperidin-4-yl)oxy)-3-fluorophenyl)-4-(3-methoxypropoxy)-3-methylpyrrolidin-2-yl)acetic acid

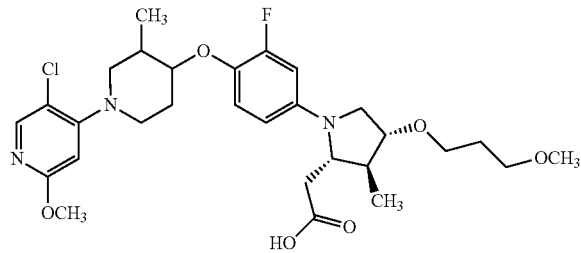 [SMILES: COCCCO[C@H]1CN(c2ccc(OC3CCN(c4cc(OC)ncc4Cl)CC3C)c(F)c2)[C@@H](CC(=O)O)[C@@H]1C]

Example 7 (yellow oil, 31.9 mg) was prepared as a single isomer from 2-fluoro-4-iodophenol and 1P, Isomer 1 following the procedure of Example 1. LC-MS Anal. Calc'd for C$_{29}$H$_{39}$ClFN$_3$O$_6$: 579.2, found [M+H] 580.3. $^1$H NMR (400 MHz, CD$_2$Cl$_2$) δ 7.94 (s, 1H), 6.96 (t, J=9.1 Hz, 1H), 6.36 (dd, J=14.0, 2.8 Hz, 1H), 6.30 (d, J=2.6 Hz, 1H), 6.28 (s, 1H), 3.85 (s, 3H), 3.78-3.65 (m, 3H), 3.64-3.36 (m, 8H), 3.30 (s, 3H), 2.85-2.72 (m, 3H), 2.60 (dd, J=12.2, 9.6 Hz, 1H), 2.41 (q, J=7.0 Hz, 1H), 2.16-2.03 (m, 2H), 1.88-1.73 (m, 3H), 1.16 (d, J=6.8 Hz, 3H), 1.00 (d, J=7.3 Hz, 3H). Analytical HPLC (ZORBAX® method, 0% Solvent B start): RT=8.6 min, HI: 100%. hGPR40 EC$_{50}$=97 nM.

Example 8

2-((2S,3S,4R)-1-(4-((1-(5-Chloro-2-ethylpyridin-4-yl)piperidin-4-yl)oxy)phenyl)-4-(3-methoxypropoxy)-3-methylpyrrolidin-2-yl)acetic acid, HCl

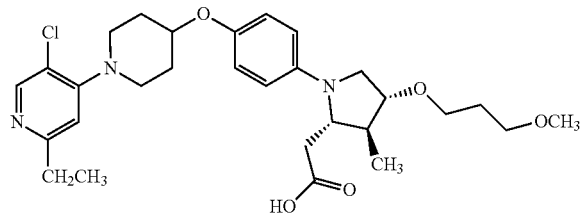 [SMILES: CCc1cc(N2CCC(Oc3ccc(N4C[C@H](OCCCOC)[C@@H](C)[C@@H]4CC(=O)O)cc3)CC2)c(Cl)cn1]

8A. 8-(2-Chloropyridin-4-yl)-1,4-dioxa-8-azaspiro[4.5]decane

To a solution of 2-chloro-4-fluoropyridine (2.63 g, 20.0 mmol) and 1,4-dioxa-8-azaspiro[4.5]decane (3.01 g, 21.0 mmol) in DMF (8 mL) was added NEt$_3$ (3.1 mL, 22 mmol). The reaction mixture was stirred at rt for 40 h. The reaction mixture was diluted with EtOAc and the organic layer was washed with brine, dried, and concentrated. The crude product was purified by silica chromatography to provide κA (4.78 g, 18.8 mmol, 94% yield). LC-MS Anal. Calc'd for C$_{12}$H$_{15}$ClN$_2$O$_2$: 254.08, found [M+H] 255.1. $^1$H NMR (400 MHz, CDCl$_3$) δ 8.03 (d, J=6.1 Hz, 1H), 6.69 (d, J=2.5 Hz, 1H), 6.6 (dd, J=6.1, 2.5 Hz, 1H), 4.02 (s, 4H), 3.52-3.50 (m, 4H), 1.80-1.58 (m, 4H).

8B. 8-(2-Ethylpyridin-4-yl)-1,4-dioxa-8-azaspiro[4.5]decane

To a solution of 8A (1.90 g, 7.48 mmol) in dioxane (19 mL) was added PdCl$_2$(dppf) (0.14 g, 0.19 mmol) and followed by a solution of diethylzinc (7.9 mL, 7.9 mmol) (1 M in hexane). The reaction mixture was stirred at 70° C. for 1 h. The reaction mixture was quenched with sat. aq. NaHCO$_3$ and diluted with EtOAc. The layers were separated and the organic layer was washed with water and brine, dried (MgSO$_4$), and concentrated. Purification via silica chromatography yielded 8B (1.9 g, 7.5 mmol, 100% yield). LC-MS Anal. Calc'd for C$_{14}$H$_{20}$N$_2$O$_2$: 248.15, found [M+H] 249.1. $^1$H NMR (400 MHz, CDCl$_3$) δ 8.19 (d, J=6.1 Hz, 1H), 6.56-6.51 (m, 2H), 3.99 (s, 4H), 3.49-3.47 (m, 4H), 2.73-2.68 (m, 2H), 1.78-1.76 (m, 4H), 1.28 (t, J=7.6, 7.6 Hz, 3H).

8C. 8-(5-Chloro-2-ethylpyridin-4-yl)-1,4-dioxa-8-azaspiro[4.5]decane

To a solution of 8B (150 mg, 0.60 mmol) in CH$_3$CN (2.3 mL) at rt was added K$_2$CO$_3$ (142 mg, 1.03 mmol) followed by NCS (137 mg, 1.03 mmol). The reaction mixture was stirred at rt for 3.5 h. K$_2$CO$_3$ (25 mg, 0.18 mmol) and NCS (24.2 mg, 0.18 mmol) were added and the reaction mixture was stirred at rt for 1 h. The reaction mixture was diluted with EtOAc, washed with sat. aq. NaHCO$_3$, water, and brine, dried (MgSO$_4$), and concentrated. Purification via silica chromatography yielded 8C (52 mg, 30% yield). LC-MS Anal. Calc'd for C$_{14}$H$_{19}$ClN$_2$O$_2$: 282.11, found [M+H] 283.0. $^1$H NMR (400 MHz, CDCl$_3$) δ 8.31 (s, 1H), 6.72 (s, 1H), 4.01 (s, 4H), 3.29-3.27 (m, 4H), 2.76-2.71 (m, 2H), 1.90-1.88 (m, 4H), 1.29-1.26 (m, 3H).

8D. 1-(5-Chloro-2-ethylpyridin-4-yl)piperidin-4-one

To a solution of 8C (68 mg, 0.24 mmol) in acetone (4.2 mL) and water (1.8 mL) was added TsOH (140 mg, 0.72 mmol). The reaction mixture was heated to 60° C. for 19 h and concentrated. The reaction mixture was treated with solid NaHCO$_3$ and diluted with EtOAc. The organic layer was washed with sat. aq. NaHCO$_3$, water, and brine, dried (MgSO$_4$), and concentrated. Purification via silica chromatography yielded 8D (37.4 mg, 0.157 mmol, 65% yield). LC-MS Anal. Calc'd for C$_{12}$H$_{15}$ClN$_2$O: 238.09, found [M+H] 239.1. $^1$H NMR (400 MHz, CDCl$_3$) δ 8.37 (s, 1H), 6.74 (s, 1H), 3.51-3.48 (m, 4H), 2.78-2.73 (m, 2H), 2.66-2.64 (m, 4H), 1.31-1.27 (m, 3H).

8E. 1-(5-Chloro-2-ethylpyridin-4-yl)piperidin-4-ol

To a solution of 8D (37 mg, 0.16 mmol) in MeOH (1 mL) and THF (0.6 mL) at 0° C., NaBH$_4$ (18 mg, 0.47 mmol) was added in portions. The reaction mixture was stirred at 0° C. for 30 min and at rt for 10 min. The reaction mixture was cooled to 0° C. and quenched with sat. aq. NaHCO$_3$ (2 mL). The MeOH and THF were evaporated. The residue was extracted with EtOAc. The combined extracts were washed with water and brine, dried (MgSO$_4$), and concentrated to give 8E as a gum, (38 mg, 0.16 mmol, 100% yield), which was used without further purification. LC-MS Anal. Calc'd for C$_{12}$H$_{17}$ClN$_2$O: 240.103, found [M+H] 241.1.

8F. 5-Chloro-2-ethyl-4-(4-(4-iodophenoxy)piperidin-1-yl)pyridine

To a solution of 8E (180 mg, 0.75 mmol) and 4-iodophenol (330 mg, 1.5 mmol) in toluene (12 mL) was added Bu$_3$P (0.30 mL, 1.2 mmol) followed by ADDP (300 mg, 1.2 mmol). The reaction mixture was stirred at 50° C. for 3 h and then at rt overnight. The reaction mixture was treated with 2:1 toluene/hexanes (10 mL), filtered, and the solid was washed with 2:1 toluene/hexanes. The filtrate was concentrated. Purification of the crude product via silica chromatography yielded 8F (186 mg, 0.420 mmol, 56% yield). LC-MS Anal. Calc'd for C$_{18}$H$_{20}$ClIN$_2$O: 442.031, found [M+H] 443.0. $^1$H NMR (400 MHz, CDCl$_3$) δ 8.31 (s, 1H), 7.58-7.55 (m, 2H), 6.74-6.70 (m, 3H), 4.51-4.48 (m, 1H), 3.42-3.37 (m, 2H), 3.16-3.10 (m, 2H), 2.76-2.71 (m, 2H), 2.14-2.09 (m, 4H), 1.28 (t, J=7.7, 7.7 Hz, 3H).

8G. ((2R,3S,4R)-1-(4-((1-(5-Chloro-2-ethylpyridin-4-yl)piperidin-4-yl)oxy)phenyl)-4-(3-methoxypropoxy)-3-methylpyrrolidin-2-yl)methanol To a solution of 8F (180 mg, 0.41 mmol) and 1H (70 mg, 0.34 mmol) in n-BuOH (1.7 mL) was added NaOH (48 mg, 1.2 mmol) and CuI (6.6 mg, 0.034 mmol). The reaction mixture was purged with argon and the reaction vial was sealed and stirred at 90° C. for 17 h. The mixture was poured into sat. aq. NH$_4$Cl, and extracted with CH$_2$Cl$_2$. The combined extracts were washed with brine, dried (MgSO$_4$), and concentrated. Purification via silica chromatography yielded 8G (140 mg, 0.270 mmol, 78% yield). LC-MS Anal. Calc'd for C$_{28}$H$_{40}$ClN$_3$O$_4$: 517.271, found [M+H] 518.3.

8H. ((2R,3S,4R)-1-(4-((1-(5-Chloro-2-ethylpyridin-4-yl)piperidin-4-yl)oxy)phenyl)-4-(3-methoxypropoxy)-3-methylpyrrolidin-2-yl)methyl methanesulfonate To a solution of 8G (160 mg, 0.31 mmol) in CH$_2$Cl$_2$ (3.1 mL) at 0° C., NEt$_3$ (0.11 mL, 0.77 mmol) was added followed by MsCl (0.040 mL, 0.53 mmol). The reaction mixture was stirred at 0° C. for 0.5 h. The reaction mixture was diluted with CH$_2$Cl$_2$. The organic layer was washed with water and brine, dried over MgSO$_4$, filtered, and concentrated to give the mesylate, which was used in the next step without purification. To a solution of the crude material in DMSO (1.5 mL), NaCN (45 mg, 0.93 mmol) was added. The reaction mixture was stirred at 50° C. for 3 h. The reaction mixture was diluted with EtOAc, washed with aq. NaHCO$_3$, water, and brine, dried (MgSO$_4$), and concentrated. Purification via silica chromatography yielded 8H (131 mg, 0.249 mmol, 81% yield). LC-MS Anal. Calc'd for C$_{29}$H$_{39}$ClN$_4$O$_3$: 526.271, found [M+H]527.3. $^1$H NMR (400 MHz, CDCl$_3$) δ 8.31 (s, 1H), 6.92-6.89 (m, 2H) 6.72 (s, 1H), 6.51-6.49 (m, 2H), 4.35 (br. s, 1H), 3.76-3.42 (m, 10H), 3.33 (s, 3H), 3.11-2.71 (m, 6H), 2.09-1.82 (m, 6H), 1.30-1.27 (m, 4H), 1.06 (d, J=7.4 Hz, 3H).

8I. Methyl 2-((2S,3S,4R)-1-(4-((1-(5-chloro-2-ethylpyridin-4-yl)piperidin-4-yl)oxy)phenyl)-4-(3-methoxypropoxy)-3-methylpyrrolidin-2-yl)acetate A 3 M HCl/MeOH/CH$_2$Cl$_2$/MeAc solution [25.2 mL, prepared by addition of AcCl (5.2 mL) to a 3/2 CH$_2$Cl$_2$/MeOH solution (20 mL) at 0° C. and then stirring at rt for 20 min] was added to 8H (130 mg, 0.25 mmol). The reaction mixture was allowed to stand for 16 h at rt. The reaction mixture was concentrated and rotovapped down with MeOH (2×). Then a 3 M HCl/MeOH solution [25.2 mL, prepared by addition of AcCl (5.2 mL) to a 3/2 CHCl$_2$/MeOH solution (20 mL) at 0° C. and then stirring at rt for 20 min] was added to the mixture, which was heated to 40° C. for 24 h without stirring. The reaction mixture was concentrated and diluted with EtOAc. The organic layer was washed with aq. NaHCO$_3$, water, and brine, dried (MgSO$_4$), and concentrated. Purification via silica chromatography yielded 8I (118 mg, 0.211 mmol, 85% yield). LC-MS Anal. Calc'd for C$_{30}$H$_{42}$ClN$_3$O$_5$: 559.28, found [M+H] 560.4. $^1$H NMR (400 MHz, CDCl$_3$) δ 8.30 (s, 1H), 6.91-6.88 (m, 2H) 6.72 (s, 1H), 6.53-6.51 (m, 2H), 4.32 (br. s, 1H), 3.72-3.42 (m, 13H), 3.33 (s, 3H), 3.10-2.70 (m, 6H), 2.08-1.81 (m, 7H), 1.30-1.26 (t, J=7.6, 7.6 Hz, 3H), 1.02-1.00 (m, 3H).

Example 8

To a solution of 8I (70 mg, 0.13 mmol) in THF (3.5 mL), 1 N aq. LiOH (0.75 mL, 0.75 mmol) was added. The reaction mixture was stirred at rt for 24 h. The mixture was cooled to 0° C., neutralized to pH<7 with 1 N aq. HCl, and extracted with CH$_2$Cl$_2$. The combined organic layers were dried (MgSO$_4$), filtered, and concentrated. The residue was purified via RP-Prep. HPLC. The product was treated with CH$_3$CN (5 mL) and 1 N aq. HCl (0.3 mL) and concentrated. The procedure was repeated (2×) to yield Example 8 (0.011 g, 0.018 mmol, 14% yield) as an off-white solid. LC-MS Anal. Calc'd for C$_{29}$H$_{40}$ClN$_3$O$_5$: 545.266, found [M+H] 546.3. $^1$H NMR (400 MHz, D$_2$O) δ 8.20 (s, 1H), 7.47-7.45 (d, J=8.3 Hz, 2H) 7.15-7.14 (d, J=9.1 Hz, 2H), 7.04 (s, 1H), 4.79 (br. s, 1H), 4.09 (br. s, 1H), 3.95-3.80 (m, 5H), 3.60-3.51 (m, 6H), 3.33 (s, 3H), 2.79-2.69 (m, 4H), 2.31 (m, 1H), 2.17-2.13 (m, 2H), 1.93-1.82 (m, 4H), 1.25-1.22 (m, 6H). Analytical HPLC: RT=5.8 min, HI: 97.0%. hGPR40 EC$_{50}$=1100 nM.

Example 9

2-((2S,3S,4R)-1-(6-(((3,4-trans)-1-(5-Ethoxy-2-fluorophenyl)-3-methylpiperidin-4-yl)oxy)pyridin-3-yl)-4-(3-methoxypropoxy)-3-methylpyrrolidin-2-yl) acetic acid, HCl

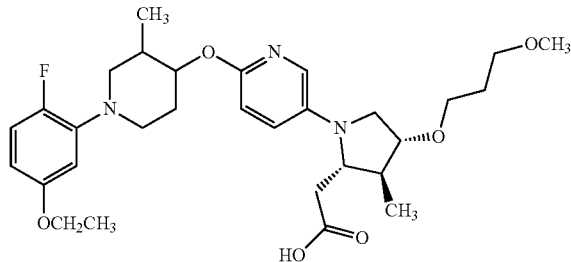 [SMILES: CCOc1ccc(F)c(N2CCC(Oc3ccc(N4C[C@H](OCCCOC)[C@@H](C)[C@@H]4CC(=O)O)cn3)C(C)C2)c1]

9A. 5-Ethoxy-2-fluoroaniline

To a solution of (5-ethoxy-2-fluorophenyl) boronic acid (10.1 g, 55.0 mmol) in MeOH (220 mL) was added 14.8 M aq. NH$_4$OH (18.6 mL, 275 mmol) and then cuprous oxide (1.57 g, 11.0 mmol). The reaction mixture was stirred under air for 7 h. The reaction mixture was concentrated. The crude product was dissolved in EtOAc/hexanes (2:1). The material was filtered through CELITE® and concentrated. The crude material was purified by silica chromatography to provide 9A (4.10 g, 26.4 mmol, 48% yield) as a brown oil. LC-MS Anal. Calc'd for $C_8H_{10}FNO$: 155.17, found [M+H] 156.1. $^1H$ NMR (400 MHz, $CDCl_3$) δ 6.86 (dd, J=10.9, 8.8 Hz, 1H), 6.32 (dd, J=7.5, 2.9 Hz, 1H), 6.20 (dt, J=8.8, 3.3 Hz, 1H), 3.94 (q, J=6.9 Hz, 2H), 3.68 (br. s, 2H), 1.37 (t, J=6.9 Hz, 3H).

9B. 1-Benzyl-1,3-dimethyl-4-oxopiperidin-1-ium, iodide salt

To a solution of 1-benzyl-3-methylpiperidin-4-one (14.0 g, 68.9 mmol) in acetone (68.9 mL) at rt was added MeI (8.61 mL, 138 mmol) dropwise. The reaction mixture was stirred at rt overnight and then concentrated to obtain 9B (24.0 g, 69.5 mmol, 101% yield) as a light yellow foam. LC-MS Anal. Calc'd for $C_{14}H_{20}NO$: 218.15, found [M+H] 219.2.

9C. 1-(5-Ethoxy-2-fluorophenyl)-3-methylpiperidin-4-one

To a solution of 9A (7.87 g, 50.7 mmol) in EtOH (103 mL) was added $K_2CO_3$ (1.05 g, 7.61 mmol), 9B (26.3 g, 76.0 mmol), and water (46.6 mL). The reaction mixture was heated to 95° C. overnight. The reaction mixture was cooled to rt and diluted with EtOAc/water. The layers were separated and the aqueous layer was extracted with EtOAc (2×). The combined organic layers were washed with brine, dried ($MgSO_4$), and concentrated. The crude product was purified by silica chromatography to provide 9C (10.1 g, 40.3 mmol, 79% yield) as a colorless oil, which solidified overnight. LC-MS Anal. Calc'd for $C_{14}H_{18}FNO_2$: 251.13, found [M+H] 252.2. $^1H$ NMR (400 MHz, $CDCl_3$) δ 6.95 (dd, J=12.1, 8.8 Hz, 1H), 6.52 (dd, J=7.5, 2.9 Hz, 1H), 6.44 (dt, J=8.8, 3.2 Hz, 1H), 3.98 (q, J=7.3 Hz, 2H), 3.75-3.64 (m, 2H), 3.12 (td, J=11.7, 3.5 Hz, 1H), 2.85-2.69 (m, 3H), 2.49 (dt, J=14.1, 3.3 Hz, 1H), 1.40 (t, J=6.9 Hz, 3H), 1.09 (d, J=6.1 Hz, 3H).

9D. (3,4-cis)-1-(5-Ethoxy-2-fluorophenyl)-3-ethylpiperidin-4-ol

To a solution of 9C (4.920 g, 19.58 mmol) in THF (98 mL) at −78° C. was added a 1 M solution of L-Selectride (23.5 mL, 23.5 mmol) in THF. After 1 h, the reaction mixture was quenched with 1 M aq. NaOH (23.5 mL, 23.5 mmol) and warmed to 0° C. $H_2O_2$ (7.4 mL, 72 mmol) was added dropwise and the reaction mixture was warmed to rt and stirred for 1 h. The reaction mixture was diluted with EtOAc/water and the layers were separated. The aqueous layer was extracted with EtOAc (2×). The combined organic layers were washed with brine, dried ($MgSO_4$), and concentrated. The crude product was purified by silica chromatography to provide 9D (4.453 g, 17.58 mmol, 90% yield) as a colorless oil. LC-MS Anal. Calc'd for $C_{14}H_{20}FNO_2$: 253.31, found [M+H] 254.0. $^1H$ NMR (500 MHz, $CDCl_3$) δ 6.89 (dd, J=12.1, 8.8 Hz, 1H), 6.52 (dd, J=7.3, 2.9 Hz, 1H), 6.37 (dt, J=8.8, 3.2 Hz, 1H), 3.97 (q, J=7.1 Hz, 2H), 3.90 (br. s, 1H), 3.13-3.02 (m, 2H), 3.02-2.95 (m, 1H), 2.84 (dd, J=11.4, 9.8 Hz, 1H), 2.05 (dqt, J=10.1, 6.7, 3.6 Hz, 1H), 2.00-1.91 (m, 1H), 1.91-1.83 (m, 1H), 1.50 (br. s, 1H), 1.38 (t, J=6.9 Hz, 3H), 1.03 (d, J=6.9 Hz, 3H).

9E. (3,4-cis)-1-(5-Ethoxy-2-fluorophenyl)-3-methylpiperidin-4-ol, Isomer 2

9D (29.2 g, 115 mmol) was purified by chiral SFC to give 9E as single isomers. 9E, Isomer 2 (13.5 g, 53.5 mmol, 47% yield) was obtained as a colorless oil after concentration. LC-MS Anal. Calc'd for $C_{14}H_{18}FNO_2$: 251.13, found [M+H] 252.2. $^1H$ NMR (400 MHz, $CDCl_3$) δ 6.95 (dd, J=12.1, 8.8 Hz, 1H), 6.52 (dd, J=7.5, 2.9 Hz, 1H), 6.44 (dt, J=8.8, 3.2 Hz, 1H), 3.98 (q, J=7.3 Hz, 2H), 3.75-3.64 (m, 2H), 3.12 (td, J=11.7, 3.5 Hz, 1H), 2.85-2.69 (m, 3H), 2.49 (dt, J=14.1, 3.3 Hz, 1H), 1.40 (t, J=6.9 Hz, 3H), 1.09 (d, J=6.1 Hz, 3H).

Example 9 (yellow solid, 29.3 mg) was prepared as a single isomer from 9E and 5-iodopyridin-2-ol following the procedure of Example 2. LC-MS Anal. Calc'd for $C_{30}H_{42}FN_3O_6$: 559.67, found [M+H] 560.2. $^1H$ NMR (500 MHz, $CD_3CN$) δ 8.01 (br. s, 1H), 7.77 (d, J=6.4 Hz, 1H), 7.53 (br. s, 1H), 7.38 (d, J=7.0 Hz, 1H), 7.28 (dd, J=11.6, 9.4 Hz, 1H), 7.03 (d, J=8.6 Hz, 1H), 5.01-4.83 (m, 1H), 4.05 (q, J=6.8 Hz, 2H), 4.00-3.89 (m, 1H), 3.88-3.78 (m, 3H), 3.72 (d, J=9.7 Hz, 1H), 3.64-3.45 (m, 5H), 3.40 (t, J=6.3 Hz, 2H), 3.25 (s, 3H), 3.09-2.93 (m, 1H), 2.74 (d, J=6.2 Hz, 2H), 2.70-2.58 (m, 1H), 2.58-2.47 (m, 1H), 2.46-2.37 (m, 1H), 1.76 (quin, J=6.2 Hz, 2H), 1.37 (t, J=6.7 Hz, 3H), 1.14 (d, J=5.7 Hz, 3H), 0.98 (d, J=7.3 Hz, 3H). Analytical HPLC: RT=9.1 min, HI: 95.5%. hGPR40 $EC_{50}$=170 nM. hGPR40 IP1 $EC_{50}$=35 nM.

Example 10

2-((2R,4R)-1-(4-((1-(5-Ethoxy-2-fluorophenyl)piperidin-4-yl)oxy)phenyl)-4-(3-methoxypropyl)pyrrolidin-2-yl)acetic acid, TFA

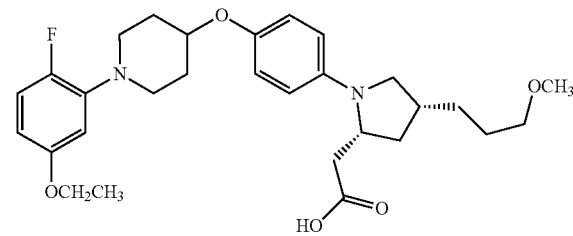 [SMILES: CCOc1ccc(F)c(N2CCC(Oc3ccc(N4C[C@H](CCCOC)C[C@@H]4CC(=O)O)cc3)CC2)c1]

10A. (R)-1-Benzyl 2-methyl 4-oxopyrrolidine-1,2-dicarboxylate

To a solution of (2R,4R)-1-Benzyl 2-methyl 4-hydroxypyrrolidine-1,2-dicarboxylate (16.7 g, 59.7 mmol) in $CH_2Cl_2$ (149 mL) was added TCCA (13.9 g, 59.7 mmol) followed by the addition of TEMPO (0.093 g, 0.60 mmol). The reaction mixture was warmed to rt and stirred for 15 min. The reaction mixture was filtered and washed with sat. $Na_2CO_3$, 0.1 M aq. HCl, and brine. The organic layer was dried ($MgSO_4$) and concentrated. The material was filtered through a plug of silica gel to obtain 10A (12.6 g, 45.3 mmol, 76% yield) as a colorless oil, which solidified upon standing to a pale yellow solid. LC-MS Anal. Calc'd for $C_{14}H_{15}NO_5$: 277.27, found [M+H] 278.0. $^1H$ NMR (500 MHz, $CDCl_3$) δ 7.43-7.28 (m, 5H), 5.27-5.20 (m, 1H), 5.19-5.08 (m, 1H), 4.92-4.78 (m, 1H), 4.07-3.88 (m, 2H), 3.81-3.56 (m, 3H), 3.03-2.87 (m, 1H), 2.61 (dd, J=18.8, 2.6 Hz, 1H).

10B. (R)-7-Benzyl 8-methyl 1,4-dioxa-7-azaspiro[4.4]nonane-7,8-dicarboxylate 10A (12.6 g, 45.3 mmol) and ethane-1,2-diol (2.5 mL, 45 mmol) were dissolved in toluene (450 mL). TsOH (1.01 g, 5.89 mmol) was added. The resulting mixture was heated to reflux for 18 h. The reaction mixture was cooled to rt, poured into ice water, extracted with EtOAc (3×), washed with brine, dried (MgSO$_4$), and concentrated. The crude product was purified by silica chromatography to provide 10B (8.58 g, 26.7 mmol, 59% yield) as a pale yellow oil, which solidified upon standing. LC-MS Anal. Calc'd for C$_{16}$H$_{19}$NO$_6$: 321.33, found [M+H] 322.0. $^1$H NMR (400 MHz, CDCl$_3$) δ 7.42-7.27 (m, 5H), 5.25-4.99 (m, 2H), 4.60-4.42 (m, 1H), 4.02-3.87 (m, 4H), 3.82-3.53 (m, 5H), 2.48-2.34 (m, 1H), 2.29-2.17 (m, 1H).

10C. (S)-2-(7-(4-((1-(5-Ethoxy-2-fluorophenyl)piperidin-4-yl)oxy)phenyl)-1,4-dioxa-7-azaspiro[4.4]nonan-8-yl)acetonitrile 10C was prepared from 10B and 3C following the procedure of Example 1. LC-MS Anal. Calc'd for C$_{27}$H$_{32}$FN$_3$O$_4$: 481.56, found [M+H] 482.2. $^1$H NMR (500 MHz, CDCl$_3$) δ 6.95-6.87 (m, 3H), 6.53 (dd, J=7.4, 3.0 Hz, 1H), 6.51-6.45 (m, 2H), 6.40 (dt, J=8.8, 3.2 Hz, 1H), 4.29 (tt, J=7.4, 3.6 Hz, 1H), 4.23-4.16 (m, 1H), 4.10-4.05 (m, 1H), 4.05-4.01 (m, 1H), 4.01-3.95 (m, 4H), 3.47-3.43 (m, 1H), 3.42-3.37 (m, 1H), 3.37-3.30 (m, 2H), 2.94 (ddd, J=11.8, 8.3, 3.3 Hz, 2H), 2.80-2.75 (m, 1H), 2.75-2.68 (m, 1H), 2.46 (dd, J=13.3, 8.1 Hz, 1H), 2.22 (dd, J=13.2, 1.4 Hz, 1H), 2.12-2.05 (m, 2H), 1.99-1.90 (m, 2H), 1.39 (t, J=7.0 Hz, 3H).

10D. (S)-2-(1-(4-((1-(5-Ethoxy-2-fluorophenyl)piperidin-4-yl)oxy)phenyl)-4-oxopyrrolidin-2-yl)acetonitrile To a solution of 10C (1.36 g, 2.82 mmol) in acetone (39 mL) and water (17 mL) (purged with argon for 10 min) was added TsOH (2.14 g, 11.3 mmol). The reaction mixture was heated to 56° C. for 30 h. The reaction mixture was cooled to rt and diluted with EtOAc/water. 1.5 M aq. K$_2$HPO$_4$ was added to basify the reaction mixture and the layers were separated. The aqueous layer was extracted with EtOAc and the combined organic layers were washed with brine, dried (MgSO$_4$), and concentrated. 10D (1.16 g, 2.66 mmol, 94% yield) was isolated as a light brown solid and was used without further purification. LC-MS Anal. Calc'd for C$_{25}$H$_{28}$FN$_3$O$_3$: 437.51, found [M+H] 438.1. $^1$H NMR (400 MHz, CDCl$_3$) δ 7.00-6.95 (m, 2H), 6.91 (dd, J=12.1, 8.8 Hz, 1H), 6.67-6.61 (m, 2H), 6.54 (dd, J=7.4, 3.0 Hz, 1H), 6.40 (dt, J=8.8, 3.1 Hz, 1H), 4.58 (tt, J=8.0, 2.9 Hz, 1H), 4.34 (tt, J=7.4, 3.7 Hz, 1H), 3.98 (q, J=6.9 Hz, 2H), 3.86-3.71 (m, 2H), 3.39-3.28 (m, 2H), 3.05 (dd, J=18.6, 8.5 Hz, 1H), 2.96 (ddd, J=11.9, 8.1, 3.3 Hz, 2H), 2.72 (ddd, J=17.6, 12.3, 2.5 Hz, 2H), 2.57 (dd, J=16.8, 7.6 Hz, 1H), 2.16-2.06 (m, 2H), 2.02-1.89 (m, 2H), 1.40 (t, J=6.9 Hz, 3H).

10E. (S)-5-(Cyanomethyl)-1-(4-((1-(5-ethoxy-2-fluorophenyl)piperidin-4-yl)oxy)phenyl)-2,5-dihydro-1H-pyrrol-3-yl trifluoromethanesulfonate To a 1 M solution of NaHMDS (0.75 mL, 0.75 mmol) in THF (3.4 mL) at −78° C. was added a solution of 10D (0.300 g, 0.686 mmol) in THF (3.4 mL) dropwise. The reaction mixture was stirred for 30 min and then a solution of 1,1,1-trifluoro-N-phenyl-N-(trifluoromethyl)sulfonyl methanesulfonamide (0.294 g, 0.823 mmol) in THF (3.4 mL) was added dropwise. The reaction mixture was stirred for 2 h at −78° C. The reaction mixture was quenched with 1.5 M aq. K$_2$HPO$_4$ and extracted with EtOAc (2×). The combined organic layers were washed with brine, dried (MgSO$_4$), and concentrated. The crude product was purified by silica chromatography to provide 10E (0.309 g, 0.543 mmol, 79% yield) as a colorless oil. LC-MS Anal. Calc'd for C$_{26}$H$_{27}$F$_4$N$_3$O$_5$S: 569.57, found [M+H] 570.0. $^1$H NMR (400 MHz, CDCl$_3$) δ 6.98-6.86 (m, 3H), 6.58-6.49 (m, 3H), 6.40 (dt, J=8.8, 3.2 Hz, 1H), 5.93 (q, J=1.8 Hz, 1H), 4.93-4.83 (m, 1H), 4.53 (ddd, J=13.3, 6.7, 1.9 Hz, 1H), 4.36-4.27 (m, 1H), 4.22-4.15 (m, 1H), 3.98 (q, J=7.0 Hz, 2H), 3.39-3.28 (m, 2H), 2.95 (ddd, J=11.8, 8.2, 3.3 Hz, 2H), 2.82-2.78 (m, 2H), 2.15-2.05 (m, 2H), 2.01-1.88 (m, 2H), 1.40 (t, J=6.9 Hz, 3H).

10F. (S,E)-2-(1-(4-((1-(5-Ethoxy-2-fluorophenyl)piperidin-4-yl)oxy)phenyl)-4-(3-methoxyprop-1-en-1-yl)-2,5-dihydro-1H-pyrrol-2-yl)acetonitrile To a solution of 10E (0.035 g, 0.062 mmol), and (E)-2-(3-methoxyprop-1-en-1-yl)-4,4,5,5-tetramethyl-1,3,2-dioxaborolane (0.013 mL, 0.062 mmol) in dioxane (0.63 mL) was added a solution of Na$_2$CO$_3$ (0.016 g, 0.16 mmol) in water (0.063 mL). The reaction mixture was purged with argon for 10 min and then Pd(Ph$_3$P)$_4$ (1.4 mg, 1.2 μmol) was added. The reaction mixture was microwaved at 150° C. for 3 min. The reaction mixture was diluted with EtOAc/water and the layers were separated. The organic layer was washed with brine, dried (MgSO$_4$), and concentrated. The crude product was purified by silica chromatography to provide 10F (0.011 g, 0.023 mmol, 37% yield). LC-MS Anal. Calc'd for C$_{29}$H$_{34}$FN$_3$O$_3$: 491.60, found [M+H] 492.2. $^1$H NMR (500 MHz, CDCl$_3$) δ 6.96-6.87 (m, 3H), 6.57-6.52 (m, 3H), 6.48 (d, J=16.0 Hz, 1H), 6.40 (dt, J=8.8, 3.2 Hz, 1H), 5.90 (s, 1H), 5.80 (dt, J=16.0, 5.6 Hz, 1H), 4.84-4.78 (m, 1H), 4.49 (ddd, J=12.9, 5.6, 1.4 Hz, 1H), 4.29 (tt, J=7.4, 3.7 Hz, 1H), 4.14 (d, J=12.9 Hz, 1H), 4.04 (d, J=5.8 Hz, 2H), 3.98 (q, J=7.1 Hz, 2H), 3.38 (s, 3H), 3.37-3.31 (m, 2H), 2.95 (ddd, J=11.8, 8.2, 3.2 Hz, 2H), 2.81 (dd, J=16.6, 3.2 Hz, 1H), 2.64 (dd, J=16.6, 7.0 Hz, 1H), 2.10 (tdd, J=7.5, 3.6, 1.8 Hz, 2H), 2.00-1.92 (m, 2H), 1.40 (t, J=7.0 Hz, 3H).

Example 10

To a solution of 10E (0.011 g, 0.023 mmol) in MeOH (2 mL) and EtOAc (2 mL) was added 10% Pd/C (2.4 mg, 2.3 μmol). The reaction mixture was purged with argon (3×) and then H$_2$ (3×) and stirred under H$_2$ (1 atm) at rt overnight. The reaction mixture was filtered and concentrated to provide 9G (0.0100 g, 0.020 mmol, 89% yield) as a pale yellow oil. The crude material was dissolved in EtOH (0.28 mL) and a 6 M aq. solution of KOH (0.092 mL, 0.55 mmol) was added. The reaction was sealed and heated at 120° C. for 2 h. The reaction mixture was concentrated and redissolved in EtOAc. The solution was acidified to pH 2 with 1 N aq. HCl and the product was extracted with EtOAc (3×). The combined organic layers were dried (MgSO$_4$) and concentrated. The crude product was purified by RP-Prep. HPLC. The HPLC fractions were rotovapped to remove the CH$_3$CN and then the aqueous layer was extracted with CH$_2$Cl$_2$ (3×). The combined organic layers were dried (MgSO$_4$) and concentrated. The residue was dissolved in CH$_3$CN and 0.5 mL of 3 N aq. HCl was added. The reaction mixture was concentrated and the procedure was repeated (2×). The aqueous layer was lyophilized overnight to give Example 10 (0.0044 g, 6.7 μmol, 24% yield) as a colorless oil. LC-MS Anal. Calc'd for C$_{29}$H$_{39}$FN$_2$O$_5$: 514.63, found [M+H]515.3. $^1$H NMR (500 MHz, CD$_3$CN) δ 7.41 (d, J=8.0 Hz, 2H), 7.10 (d, J=9.1 Hz, 2H), 7.00 (dd, J=12.4, 8.8 Hz, 1H), 6.64 (dd, J=7.2, 3.0 Hz, 1H), 6.52 (dt, J=8.9, 3.3 Hz, 1H), 4.58 (br. s, 1H), 4.18-4.08 (m, 1H), 4.02 (q, J=6.9 Hz, 2H), 3.67 (d, J=6.9 Hz, 2H), 3.43-3.33 (m, 4H), 3.30 (s, 3H), 3.05 (ddd, J=12.0, 8.5, 3.2 Hz, 2H), 2.81-2.72 (m, 1H), 2.72-2.57 (m, 3H), 2.21-2.11 (m, 2H), 1.94-1.86 (m, 2H), 1.74-1.65 (m, 1H), 1.65-1.53 (m, 4H), 1.36 (t, J=7.0 Hz, 3H). Analytical HPLC: RT=7.1 min, HI: 95.1%. hGPR40 $EC_{50}$=380 nM. hGPR40 IP1 $EC_{50}$=47 nM.

Example 11

2-((2R,4R)-1-(4-(((3,4-trans)-1-(5-Ethoxy-2-fluorophenyl)-3-methylpiperidin-4-yl)oxy)phenyl)-4-(3-methoxypropoxy)pyrrolidin-2-yl)acetic acid, HCl

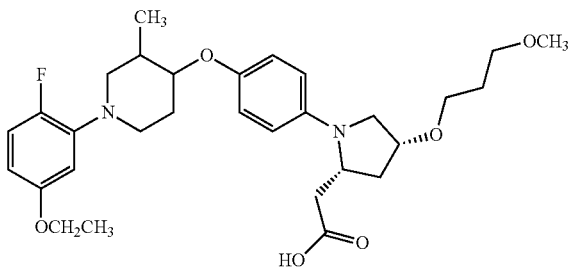 [SMILES: CCOc1ccc(F)c(N2CCC(Oc3ccc(N4C[C@H](OCCCOC)C[C@@H]4CC(=O)O)cc3)C(C)C2)c1]

11A. (2R,4R)-tert-Butyl 4-hydroxy-2-(hydroxymethyl)pyrrolidine-1-carboxylate (2R,4R)-1-(tert-Butoxycarbonyl)-4-hydroxypyrrolidine-2-carboxylic acid (6.98 g, 30.2 mmol) was dissolved in anhydrous THF (123 mL) and cooled to −10° C. 4-Methylmorpholine (3.5 mL, 32 mmol) and isobutyl chloroformate (4.2 mL, 32 mmol) were then added and the reaction mixture was stirred at −10° C. for 45 min. The reaction mixture was filtered and added dropwise to a solution of $NaBH_4$ (2.28 g, 60.4 mmol) in water (16 mL) cooled to 0° C. The reaction mixture was stirred for 2 h and slowly warmed to rt. The reaction mixture was quenched with sat. aq. $NH_4Cl$ and the product was extracted with EtOAc (3×). The combined organic layers were washed with brine, dried ($MgSO_4$), and concentrated. The crude product was purified by silica chromatography to provide 11A (5.98 g, 27.5 mmol, 91% yield) as a colorless oil, which solidified to a white solid upon standing. LC-MS Anal. Calc'd for $C_{10}H_{19}NO_4$: 217.26, found [M+H] 218.0. $^1$H NMR (500 MHz, $CDCl_3$) δ 4.35-4.09 (m, 2H), 4.09-3.88 (m, 2H), 3.67-3.33 (m, 3H), 2.44-2.24 (m, 1H), 2.07-1.71 (m, 2H), 1.53-1.40 (m, 9H).

11B. (2R,4R)-tert-Butyl 2-(((tert-butyldiphenylsilyl)oxy)methyl)-4-hydroxypyrrolidine-1-carboxylate To a solution of 11A (3.00 g, 13.8 mmol) in DMF (69 mL) was added TBDPS-Cl (3.9 mL, 15 mmol) and imidazole (1.41 g, 20.7 mmol). The reaction mixture was stirred at rt for 2 h. The reaction mixture was diluted with EtOAc and washed with water (5×). The organic layer was washed with brine, dried ($MgSO_4$), and concentrated. The crude product was purified by silica chromatography to give 11B (2.58 g, 5.66 mmol, 41% yield) as a colorless oil. LC-MS Anal. Calc'd for $C_{26}H_{37}NO_4Si$: 455.66, found [M+H] 456.1. $^1$H NMR (500 MHz, $CDCl_3$) δ 7.72-7.60 (m, 4H), 7.48-7.34 (m, 6H), 4.78 (d, J=11.0 Hz, 0.5H), 4.50 (d, J=10.2 Hz, 0.5H), 4.37-4.20 (m, 1.5H), 4.01 (br. s, 1H), 3.89 (d, J=9.4 Hz, 0.5H), 3.62-3.42 (m, 3H), 2.45-2.29 (m, 1H), 2.12-1.96 (m, 1H), 1.54-1.43 (s, 4.5H), 1.29 (s, 4.5H), 1.08 (s, 9H).

11C. (2R,4R)-tert-Butyl 2-(((tert-butyldiphenylsilyl)oxy)methyl)-4-(3-methoxypropoxy)pyrrolidine-1-carboxylate To a solution of 11B (0.098 g, 0.22 mmol) in THF (2.2 mL) at 0° C. was added 60% NaH (0.060 g, 1.5 mmol). The reaction mixture was stirred for 30 min and then 1-bromo-3-methoxypropane (0.17 mL, 1.5 mmol) was added. The reaction mixture was warmed to rt and refluxed overnight. The reaction mixture was quenched with water and diluted with EtOAc. The layers were separated and the aqueous layer was extracted with EtOAc. The combined organic layers were washed with brine, dried ($MgSO_4$), and concentrated. The crude product was purified by silica chromatography to provide 11C (0.028 g, 0.053 mmol, 25% yield) as a colorless oil. LC-MS Anal. Calc'd for $C_{30}H_{45}NO_5Si$: 527.77, found [M+H] 528.3. $^1$H NMR (400 MHz, $CDCl_3$) δ 7.73-7.60 (m, 4H), 7.46-7.30 (m, 6H), 3.99 (br. s, 1H), 3.94-3.74 (m, 2H), 3.71-3.59 (m, 2H), 3.52-3.36 (m, 4H), 3.36-3.31 (m, 1H), 3.30 (s, 3H), 2.49-2.22 (m, 1H), 2.15-2.02 (m, 1H), 1.83-1.70 (m, 2H), 1.49-1.25 (m, 9H), 1.06 (s, 9H).

11D. (2R,4R)-tert-Butyl 2-(hydroxymethyl)-4-(3-methoxypropoxy) pyrrolidine-1-carboxylate To a solution of 11C (0.367 g, 0.696 mmol) in THF (3.5 mL) at rt was added a 1 M solution of TBAF (1.0 mL, 1.0 mmol) in THF. The reaction mixture was stirred at rt overnight. The reaction mixture was diluted with EtOAc/water and the layers were separated. The aqueous layer was extracted with EtOAc and the combined organic layers were washed with brine, dried ($MgSO_4$), and concentrated. The crude product was purified by silica chromatography to provide 11D (0.187 g, 0.647 mmol, 93% yield) as a colorless oil. LC-MS Anal. Calc'd for $C_{14}H_{27}NO_5$: 289.37, found [M+H] 290.1. $^1$H NMR (500 MHz, $CDCl_3$) δ 4.43 (d, J=6.9 Hz, 1H), 4.11-4.02 (m, 1H), 4.02-3.90 (m, 1H), 3.87-3.58 (m, 2H), 3.57-3.47 (m, 3H), 3.47-3.37 (m, 3H), 3.33 (s, 3H), 2.18 (m, 1H), 1.82 (quin, J=6.3 Hz, 2H), 1.46 (s, 9H).

11E. ((2R,4R)-4-(3-Methoxypropoxy)pyrrolidin-2-yl)methanol, HCl

A 4 N solution of HCl (1.00 mL, 4.00 mmol) in dioxane was added to 11D (0.079 g, 0.27 mmol). The reaction mixture was stirred at rt for 1 h. The reaction mixture was concentrated and rotovapped with MeOH (2×) to provide 11E (0.062 g, 0.27 mmol, 100% yield) as a colorless oil. LC-MS Anal. Calc'd for $C_9H_{19}NO_3$: 189.25, found [M+H] 190.0.

11F. (3,4-trans)-1-(5-Ethoxy-2-fluorophenyl)-4-(4-iodophenoxy)-3-methylpiperidine To a solution of 9E (0.511 g, 2.02 mmol), 4-iodophenol (0.577 g, 2.62 mmol), and $Bu_3P$ (0.80 mL, 3.2 mmol) in toluene (25 mL) was added ADDP (0.815 g, 3.23 mmol). The reaction mixture was sonicated for 99 min. The reaction mixture was poured into hexanes, filtered, and concentrated. The crude product was purified by silica chromatography to provide 11F (0.643 g, 1.41 mmol, 70% yield) as a colorless oil. LC-MS Anal. Calc'd for $C_{20}H_{23}FINO_2$: 455.31, found

[M+H] 456.2. ¹H NMR (400 MHz, CDCl₃) δ 7.62-7.49 (m, 2H), 6.91 (dd, J=12.1, 8.8 Hz, 1H), 6.76-6.67 (m, 2H), 6.50 (dd, J=7.5, 2.9 Hz, 1H), 6.40 (dt, J=8.8, 3.2 Hz, 1H), 3.98 (q, J=6.9 Hz, 2H), 3.89 (td, J=9.0, 4.0 Hz, 1H), 3.51-3.36 (m, 2H), 2.81 (td, J=11.5, 2.8 Hz, 1H), 2.57 (dd, J=12.1, 9.6 Hz, 1H), 2.22-2.08 (m, 2H), 1.90-1.75 (m, 1H), 1.40 (t, J=6.9 Hz, 3H), 1.08 (d, J=6.6 Hz, 3H).

Example 11 (beige solid, 25 mg) was prepared as a single isomer from 11E and 11F following the procedure of Example 1. LC-MS Anal. Calc'd for C₃₀H₄₁FN₂O₆: 544.66, found [M+H] 545.3. ¹H NMR (500 MHz, CD₃CN) δ 7.80 (br. s, 1H), 7.74 (d, J=8.8 Hz, 2H), 7.21 (dd, J=12.1, 9.1 Hz, 1H), 7.11 (d, J=9.1 Hz, 2H), 6.92 (dt, J=9.0, 3.1 Hz, 1H), 4.50-4.43 (m, 1H), 4.33 (td, J=9.8, 4.7 Hz, 1H), 4.21-4.12 (m, 1H), 4.03 (q, J=6.9 Hz, 2H), 3.83 (dd, J=12.4, 3.3 Hz, 1H), 3.74-3.63 (m, 3H), 3.62-3.56 (m, 1H), 3.51 (tq, J=6.3, 3.0 Hz, 2H), 3.46-3.41 (m, 2H), 3.37 (t, J=12.1 Hz, 1H), 3.27 (s, 3H), 3.01-2.92 (m, 1H), 2.92-2.84 (m, 1H), 2.78 (dt, J=13.4, 6.6 Hz, 2H), 2.46-2.28 (m, 2H), 2.15-2.05 (m, 1H), 1.77 (quin, J=6.3 Hz, 2H), 1.36 (t, J=6.9 Hz, 3H), 1.08 (d, J=6.6 Hz, 3H). Analytical HPLC: RT=10.5 min, HI: 97.3%. hGPR40 EC₅₀=100 nM. hGPR40 IP1 EC₅₀=16 nM.

Example 12

2-((2R,4R)-1-(4-((1-(5-Ethoxy-2-fluorophenyl)piperidin-4-yl)oxy)phenyl)-4-(3-methoxypropoxy)pyrrolidin-2-yl)acetic acid, HCO₂H

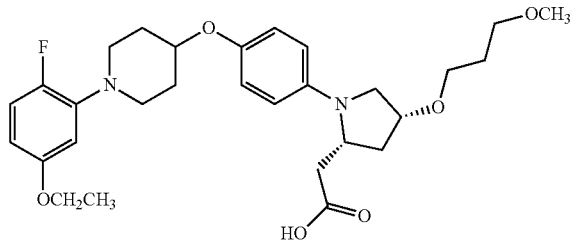 [SMILES: CCOc1ccc(F)c(N2CCC(Oc3ccc(N4C[C@H](OCCCOC)C[C@@H]4CC(=O)O)cc3)CC2)c1]

Example 12 (9.5 mg) was prepared from 11E and 3C following the procedure of Example 1. LC-MS Anal. Calc'd for C₂₉H₃₉FN₂O₆: 530.63, found [M+H] 531.2. ¹H NMR (500 MHz, DMSO-d₆) δ 7.00 (dd, J=12.0, 9.2 Hz, 1H), 6.88 (d, J=8.0 Hz, 2H), 6.52 (d, J=7.7 Hz, 1H), 6.50 (d, J=8.3 Hz, 2H), 6.47-6.43 (m, 1H), 4.31-4.24 (m, 1H), 4.16-4.11 (m, 1H), 4.01-3.93 (m, 3H), 3.52-3.42 (m, 2H), 3.41-3.22 (m, 6H), 3.21 (s, 3H), 2.91-2.83 (m, 2H), 2.62 (d, J=15.1 Hz, 1H), 2.43 (dd, J=15.0, 10.6 Hz, 1H), 2.14 (dt, J=13.4, 6.6 Hz, 1H), 2.04-1.95 (m, J=13.2 Hz, 3H), 1.78-1.67 (m, 4H), 1.29 (t, J=6.9 Hz, 3H). Analytical HPLC (Acquity method): RT=1.8 min, HI: 98.3%. hGPR40 EC₅₀=160 nM. hGPR40 IP1 EC₅₀=39 nM.

Example 13

2-((2R,4R)-1-(4-((1-(5-Ethoxy-2-fluorophenyl)piperidin-4-yl)oxy)phenyl)-4-(2-methoxyethoxy)pyrrolidin-2-yl)acetic acid, TFA

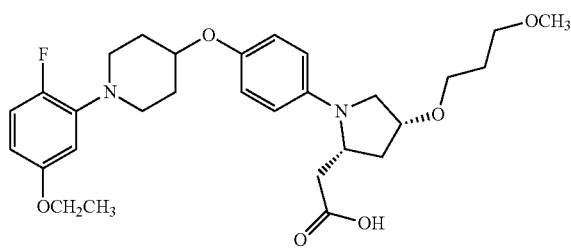 [SMILES: CCOc1ccc(F)c(N2CCC(Oc3ccc(N4C[C@H](OCCCOC)C[C@@H]4CC(=O)O)cc3)CC2)c1]

Example 13 (yellow oil, 13.6 mg) was prepared from 1-bromo-2-methoxyethane and 3C following the procedure of Example 11. LC-MS Anal. Calc'd for C₂₈H₃₇FN₂O₆: 516.26, found [M+H] 517.1. ¹H NMR (400 MHz, DMSO-d₆) δ 7.01 (dd, J=8.8, 12.5 Hz, 1H), 6.89 (d, J=9.0 Hz, 2H), 6.56-6.44 (m, 4H), 4.32-4.24 (m, 1H), 4.19 (t, J=4.9 Hz, 1H), 4.03-3.95 (m, 1H), 3.97 (q, J=7.0 Hz, 2H), 3.63-3.50 (m, 2H), 3.49-3.44 (m, 2H), 3.30-3.23 (m, 3H), 3.28 (s, 3H), 2.92-2.84 (m, 2H), 2.69-2.58 (m, 1H), 2.48-2.43 (m, 2H), 2.19-2.10 (m, 1H), 2.06-1.95 (m, 3H), 1.77-1.67 (m, 2H), 1.30 (t, J=7.0 Hz, 3H). Analytical HPLC (12 min gradient, 15 min stop): RT=10.1 min, HI: 98.0%. hGPR40 EC₅₀=1000 nM.

Example 14

2-((2S,3S,4R)-1-(4-(((3,4-trans)-1-(5-Ethoxy-2-fluorophenyl)-3-methylpiperidin-4-yl)oxy)phenyl)-4-(3-methoxypropoxy)-3-methylpyrrolidin-2-yl)acetic acid, HCl

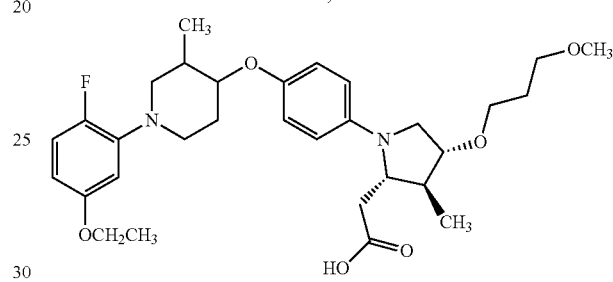

Example 14 (tan solid, 38.0 mg) was prepared as a single isomer from 11F following the procedure of Example 1. LC-MS Anal. Calc'd for C₃₁H₄₃FN₂O₆: 558.68, found [M+H] 559.2. ¹H NMR (500 MHz, CD₃CN) δ 8.04 (dd, J=6.1, 3.0 Hz, 1H), 7.83 (d, J=9.1 Hz, 2H), 7.27 (dd, J=12.1, 9.1 Hz, 1H), 7.13 (d, J=9.1 Hz, 2H), 7.02 (dt, J=9.2, 3.4 Hz, 1H), 4.41 (td, J=10.2, 4.1 Hz, 1H), 4.11-4.01 (m, 3H), 3.93 (dt, J=11.3, 5.6 Hz, 1H), 3.87 (td, J=12.4, 2.6 Hz, 1H), 3.83-3.75 (m, 2H), 3.72 (d, J=12.1 Hz, 1H), 3.68-3.61 (m, 1H), 3.58-3.49 (m, 3H), 3.43 (td, J=6.3, 1.1 Hz, 2H), 3.26 (s, 3H), 3.05-2.97 (m, 1H), 2.97-2.88 (m, 1H), 2.81 (dd, J=17.3, 5.5 Hz, 1H), 2.58-2.46 (m, 1H), 2.45-2.33 (m, 2H), 1.77 (quin, J=6.3 Hz, 2H), 1.37 (t, J=7.0 Hz, 3H), 1.20 (d, J=6.9 Hz, 3H), 1.09 (d, J=6.6 Hz, 3H). Analytical HPLC: RT=11.2 min, HI: 95.8%. hGPR40 EC₅₀=51 nM. hGPR40 IP1 EC₅₀=7 nM.

Example 16

2-((2S,3 S,4R)-1-(4-((1-(5-Ethoxy-2-fluorophenyl)piperidin-4-yl)oxy)phenyl)-3-methyl-4-(3-(methylsulfonyl)propoxy)pyrrolidin-2-yl)acetic acid

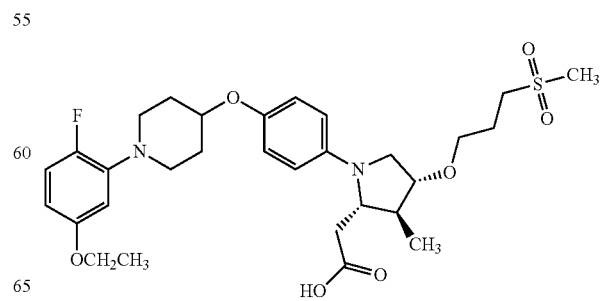

16A. 3-(Methylthio)propyl 4-methylbenzenesulfonate

A solution of 3-(methylthio)propan-1-ol (0.97 mL, 9.4 mmol), NEt$_3$ (2.0 mL, 14 mmol), and N,N,N',N'-tetramethyl-1,6-hexanediamine (0.20 mL, 0.94 mmol) in toluene (9.4 mL) was cooled to 0° C. A solution of TsCl (2.69 g, 14.1 mmol) in toluene (9.4 mL) was added dropwise. The reaction mixture was warmed to rt and stirred for 3 h. The reaction mixture was diluted with water and extracted with EtOAc. The combined organic layers were washed with brine, dried (MgSO$_4$), and concentrated. The crude product was purified by silica chromatography to provide 16A (2.17 g, 8.31 mmol, 88% yield) as a colorless oil. LC-MS Anal. Calc'd for C$_{11}$H$_{16}$O$_3$S$_2$: 260.37, found [M+H] 261.0.

16B. 3-(Methylsulfonyl)propyl 4-methylbenzenesulfonate

To a solution of 16A (2.16 g, 8.31 mmol) in MeOH (44 mL) cooled to 0° C. was added a solution of OXONE® (10.2 g, 16.6 mmol) in water (44 mL). The ice bath was allowed to gradually warm to rt and the reaction mixture was stirred for 3 h. The MeOH was removed under reduced pressure and the reaction mixture was diluted with water. The aqueous layer was extracted with EtOAc (3×) and the combined organic layers were washed with brine, dried (MgSO$_4$), and concentrated to give 16B (2.39 g, 8.17 mmol, 98% yield) as a white solid. LC-MS Anal. Calc'd for C$_{11}$H$_{16}$O$_5$S$_2$: 292.37, found [M+H] 293.0.

Example 16 (8.4 mg) was prepared from 16B and 3C following the procedure of Example 1. LC-MS Anal. Calc'd for C$_{30}$H$_{41}$FN$_2$O$_7$S: 592.72, found [M+H] 593.2. $^1$H NMR (500 MHz, DMSO-d$_6$) δ 7.00 (t, J=10.5 Hz, 1H), 6.88 (d, J=7.4 Hz, 2H), 6.56-6.50 (m, 1H), 6.50-6.42 (m, 3H), 4.32-4.23 (m, 1H), 4.00-3.91 (m, 2H), 3.75 (br. s, 1H), 3.60 (d, J 10.2 Hz, 1H), 3.54 (d, J 6.6 Hz, 2H), 3.43-3.39 (m, 2H), 3.24 (br. s, 2H), 3.14 (br. s, 2H), 2.97 (br. s, 3H), 2.92-2.81 (m, 2H), 2.61 (d, J=15.4 Hz, 1H), 2.48-2.41 (m, 1H), 2.32-2.22 (m, 1H), 2.04-1.96 (m, 2H), 1.95-1.88 (m, 2H), 1.77-1.66 (m, J=8.3 Hz, 2H), 1.32-1.26 (m, 3H), 0.94 (d, J=6.3 Hz, 3H). Analytical HPLC (Acquity): RT=1.7 min, HI: 100%. hGPR40 EC$_{50}$=980 nM.

Example 18, Isomer 1 and Isomer 2

2-((2S,3S,4R)-1-(6-(((3,4-trans)-1-(5-Chloro-2-methoxypyridin-4-yl)-3-isobutylpiperidin-4-yl)oxy)pyridin-3-yl)-4-(3-methoxypropoxy)-3-methylpyrrolidin-2-yl)acetic acid

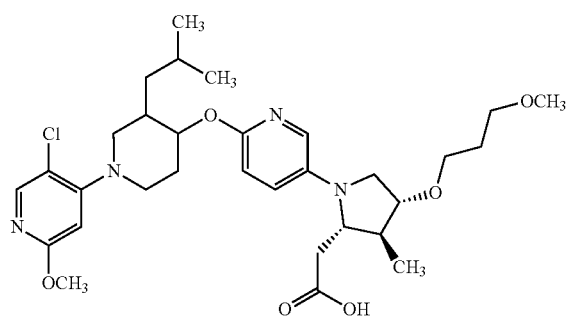 [SMILES: COCCCO[C@H]1CN(c2ccc(OC3CCN(c4cc(OC)ncc4Cl)CC3CC(C)C)nc2)[C@@H](CC(=O)O)[C@@H]1C]

18A. Ethyl 1-benzyl-3-isobutyl-4-oxopiperidine-3-carboxylate

To a solution of ethyl 1-benzyl-4-oxopiperidine-3-carboxylate, HCl (9.27 g, 31.1 mmol) in i-PrOH (31 mL) was added KOtBu (72 mL, 72 mmol) (1 M in i-PrOH) and 1-iodo-2-methylpropane (5.4 mL, 47 mmol). The reaction mixture was stirred at rt for 20 min and then at 75° C. for 12 h. The reaction mixture was cooled to rt and poured into sat. aq. NH$_4$Cl. The product was extracted with EtOAc, washed with brine, dried (Na$_2$SO$_4$), and concentrated. The crude product was purified by silica chromatography to give 18A (4.70 g, 14.8 mmol, 48% yield) as a colorless oil. LC-MS Anal. Calc'd for C$_{19}$H$_{27}$NO$_3$: 317.42, found [M+H] 318.2. $^1$H NMR (400 MHz, CDCl$_3$) δ 7.35-7.29 (m, 4H), 7.29-7.27 (m, 1H), 3.58 (s, 2H), 3.44 (dd, J=11.6, 2.8 Hz, 1H), 3.07-2.93 (m, 1H), 2.92-2.78 (m, 1H), 2.47-2.33 (m, 2H), 2.23 (d, J=11.4 Hz, 1H), 2.04 (s, 1H), 1.82-1.75 (m, 1H), 1.74-1.63 (m, 1H), 1.45 (dd, J=13.9, 5.9 Hz, 1H), 1.30-1.22 (m, 4H), 0.88 (d, J=6.6 Hz, 3H), 0.83 (d, J=6.6 Hz, 3H).

18B. 1-Benzyl-3-isobutylpiperidin-4-one

To a flask with 18A (4.70 g, 14.8 mmol) was added 6 M aq. HCl (49 mL, 300 mmol). The reaction mixture was stirred at 100° C. for 12 h. The reaction mixture was cooled to rt and poured into 5 N NaOH/ice water and additional 5 N NaOH was added until the pH ~8. The reaction mixture was diluted with EtOAc, washed with water and brine, dried over Na$_2$SO$_4$, and concentrated. The crude product was purified by silica chromatography to provide 18B (2.11 g, 8.60 mmol, 58% yield) as a colorless oil. LC-MS Anal. Calc'd for C$_{16}$H$_{23}$NO: 245.36, found [M+H] 246.2. $^1$H NMR (400 MHz, CDCl$_3$) δ 7.38-7.31 (m, 4H), 7.30-7.27 (m, 1H), 3.72-3.62 (m, 1H), 3.60-3.50 (m, 1H), 3.05-2.91 (m, 2H), 2.63-2.46 (m, 3H), 2.44-2.35 (m, 1H), 2.23 (dd, J=11.1, 9.4 Hz, 1H), 1.72 (ddd, J=13.9, 7.9, 6.2 Hz, 1H), 1.59-1.45 (m, 1H), 1.09 (dt, J=13.8, 6.8 Hz, 1H), 0.87 (d, J=6.6 Hz, 3H), 0.84 (d, J=6.6 Hz, 3H). 18C. (3,4-cis)-1-Benzyl-3-isobutylpiperidin-4-ol: To a solution of 18B (1.51 g, 6.15 mmol) in THF (31 mL) at −78° C. was added a 1 M solution of L-Selectride (9.2 mL, 9.2 mmol) in THF. The reaction mixture was stirred at −78° C. for 1.5 h and then quenched with 1 M aq. NaOH (9.2 mL, 9.2 mmol) and warmed to rt. 30% Aq. H$_2$O$_2$ (9.4 mL, 92 mmol) was added and the reaction mixture was stirred at rt for 0.5 h. The reaction mixture was diluted with EtOAc/water and the layers were separated. The aqueous layer was extracted with EtOAc (2×). The combined organic layers were washed with brine, dried (Na$_2$SO$_4$), and concentrated. The crude product was purified by silica chromatography to provide 18C (0.66 g, 2.7 mmol, 43% yield) as a colorless oil. LC-MS Anal. Calc'd for C$_{16}$H$_{25}$NO: 247.38, found [M+H] 248.1. $^1$H NMR (400 MHz, CDCl$_3$) δ 7.33-7.28 (m, 4H), 7.26-7.21 (m, 1H), 3.87 (br. s., 1H), 3.59-3.50 (m, 1H), 3.49-3.42 (m, 1H), 2.55 (d, J=11.0 Hz, 1H), 2.47 (d, J=8.6 Hz, 1H), 2.41-2.28 (m, 1H), 2.10 (t, J=10.7 Hz, 1H), 1.87-1.70 (m, 3H), 1.65-1.55 (m, 2H), 1.24-1.17 (m, 2H), 0.87 (d, J=6.6 Hz, 6H).

18D. (3,4-cis)-3-Isobutylpiperidin-4-ol

To a solution 18C (0.66 g, 2.7 mmol) in MeOH (18 mL) was added 10% Pd/C (0.142 g, 0.133 mmol). The mixture was evacuated and purged with H$_2$ (3×) and then stirred under a H$_2$ balloon for 4 h. The reaction mixture was filtered through CELITE® and concentrated to give 18D (0.39 g, 2.480 mmol, 93% yield) as a white solid. LC-MS Anal.

Calc'd for $C_9H_{19}NO$: 157.25, found [M+H] 158.1. $^1$H NMR (400 MHz, $CDCl_3$) δ 3.93 (q, J=3.4 Hz, 1H), 3.04-2.90 (m, 1H), 2.77 (dt, J=12.2, 4.1 Hz, 1H), 2.72-2.67 (m, 2H), 1.76 (br. s., 2H), 1.74-1.67 (m, 3H), 1.67-1.57 (m, 1H), 1.24-1.08 (m, 2H), 0.89 (d, J=6.6 Hz, 6H).

18E. (3,4-cis)-1-(5-Chloro-2-methoxypyridin-4-yl)-3-isobutylpiperidin-4-ol

To a solution of 18D (320 mg, 2.04 mmol) and $K_2CO_3$ (1130 mg, 8.14 mmol) in DMSO (4.1 mL) was added 1J (475 mg, 2.14 mmol). The reaction mixture was stirred at 110° C. for 1 h and then at 90° C. overnight. The reaction mixture was diluted with EtOAc and the organic layer was washed with water and brine, dried over $Na_2SO_4$, and concentrated. The crude product was purified by silica chromatography to provide 18E (493 mg, 1.65 mmol, 81% yield) as a colorless oil. LC-MS Anal. Calc'd for $C_{15}H_{23}ClN_2O_2$: 298.81, found [M+H] 299.1. $^1$H NMR (400 MHz, $CDCl_3$) δ 7.93 (s, 1H), 6.26 (s, 1H), 3.97 (d, J=3.3 Hz, 1H), 3.86 (s, 3H), 3.29-3.22 (m, 1H), 3.19 (ddd, J=11.9, 3.9, 1.7 Hz, 1H), 3.06 (td, J=11.8, 3.1 Hz, 1H), 2.77 (t, J=11.2 Hz, 1H), 1.99-1.88 (m, 2H), 1.88-1.80 (m, 1H), 1.70 (br. s., 1H), 1.68-1.58 (m, 1H), 1.23-1.18 (m, 2H), 0.91 (d, J=4.0 Hz, 3H), 0.89 (d, J=4.2 Hz, 3H).

Example 18, Isomer 1 and Isomer 2 were prepared from 18E following the procedure of Example 2 followed by chiral SFC to separate the two isomers. Example 18, Isomer 1 (19.4 mg). LC-MS Anal. Calc'd for $C_{31}H_{45}ClN_4O_6$: 605.17, found [M+]605.30. $^1$H NMR (500 MHz, DMSO-$d_6$) δ 8.02 (s, 1H), 7.43 (br. s., 1H), 7.04 (d, J=8.8 Hz, 1H), 6.70 (d, J=8.8 Hz, 1H), 6.43 (s, 1H), 4.72 (br. s., 1H), 3.81 (s, 3H), 3.73 (br. s., 1H), 3.66-3.54 (m, 3H), 3.51-3.37 (m, 6H), 3.21 (s, 3H), 2.99-2.83 (m, 2H), 2.58 (d, J=15.1 Hz, 2H), 2.36-2.23 (m, 1H), 2.17 (d, J=11.6 Hz, 1H), 2.01-1.86 (m, 1H), 1.78-1.50 (m, 4H), 1.39 (t, J=10.9 Hz, 1H), 1.13 (d, J=9.1 Hz, 1H), 1.00-0.77 (m, 9H). Analytical HPLC (Acquity): RT=1.9 min, HI: 97.4%. hGPR40 $EC_{50}$=1300 nM. Example 18, Isomer 2 (19.2 mg). LC-MS Anal. Calc'd for $C_{31}H_{45}ClN_4O_6$: 605.17, found [M+] 605.30. $^1$H NMR (500 MHz, DMSO-$d_6$) δ 8.02 (s, 1H), 7.52-7.33 (m, 1H), 7.11-6.96 (m, 1H), 6.77-6.69 (m, 1H), 6.43 (s, 1H), 4.83-4.58 (m, 1H), 3.81 (s, 3H), 3.74-3.70 (m, 1H), 3.63-3.44 (m, 4H), 3.41-3.30 (m, 5H), 3.21 (s, 3H), 2.89 (s, 2H), 2.63-2.51 (m, 2H), 2.31-2.24 (m, 1H), 2.21-2.09 (m, 1H), 2.00-1.86 (m, 1H), 1.77-1.68 (m, 2H), 1.65-1.57 (m, 2H), 1.46-1.31 (m, 1H), 1.21-1.06 (m, 1H), 1.01-0.69 (m, 9H). Analytical HPLC (Acquity): RT=1.9 min, HI: 97.7%. hGPR40 $EC_{50}$=290 nM.

Example 19, Isomer 1 and Isomer 2

2-((2S,3S,4R)-1-(4-(((3,4-trans)-1-(5-Chloro-2-methoxypyridin-4-yl)-3-isobutylpiperidin-4-yl)oxy)phenyl)-4-(3-methoxypropoxy)-3-methylpyrrolidin-2-yl)acetic acid

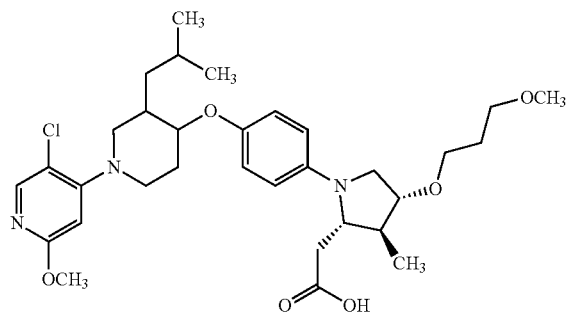 [SMILES: COCCCO[C@H]1CN(c2ccc(OC3CCN(c4cc(OC)ncc4Cl)CC3CC(C)C)cc2)[C@@H](CC(=O)O)[C@@H]1C]

Example 19, Isomer 1 and Isomer 2 were prepared from 4-iodophenol following the procedure of Example 18. Example 19, Isomer 1 (12.6 mg). LC-MS Anal. Calc'd for $C_{32}H_{46}ClN_3O_6$: 604.18, found [M+] 604.3. $^1$H NMR (500 MHz, DMSO-$d_6$) δ 8.02 (s, 1H), 6.87 (d, J=8.0 Hz, 2H), 6.47 (d, J=8.3 Hz, 2H), 6.41 (s, 1H), 3.95-3.85 (m, 1H), 3.80 (s, 3H), 3.72 (br. s., 1H), 3.62-3.52 (m, 2H), 3.50-3.44 (m, 3H), 3.34-3.25 (m, 3H), 3.20 (s, 3H), 2.95-2.83 (m, 1H), 2.65-2.52 (m, 3H), 2.26 (q, J=6.8 Hz, 1H), 2.11-2.01 (m, 1H), 1.94-1.85 (m, 1H), 1.77-1.55 (m, 4H), 1.50 (t, J=10.6 Hz, 1H), 1.26-1.15 (m, 2H), 0.93 (d, J=7.2 Hz, 3H), 0.88 (d, J=6.3 Hz, 6H). Analytical HPLC (Acquity): RT=2.2 min, HI: 94.3%. hGPR40 $EC_{50}$=1500 nM. Example 19, Isomer 2 (12.9 mg). LC-MS Anal. Calc'd for $C_{32}H_{46}ClN_3O_6$: 604.18, found [M+] 604.4. $^1$H NMR (500 MHz, DMSO-$d_6$) δ 8.02 (s, 1H), 6.87 (d, J=8.0 Hz, 2H), 6.47 (d, J=8.0 Hz, 2H), 6.41 (s, 1H), 3.94-3.87 (m, 1H), 3.80 (s, 3H), 3.72 (d, J=3.0 Hz, 1H), 3.61-3.41 (m, 6H), 3.34-3.28 (m, 2H), 3.20 (s, 3H), 2.93-2.85 (m, 1H), 2.64-2.51 (m, 3H), 2.30-2.23 (m, 1H), 2.08 (d, J=11.0 Hz, 1H), 1.88 (d, J=4.4 Hz, 1H), 1.77-1.55 (m, 4H), 1.49 (t, J=10.9 Hz, 1H), 1.26-1.16 (m, 2H), 0.93 (d, J=6.9 Hz, 3H), 0.88 (d, J=6.3 Hz, 6H). Analytical HPLC (Acquity): RT=2.2 min, HI: 96.6%. hGPR40 $EC_{50}$=230 nM.

Example 20

2-((2S,3S,4R)-1-(4-(((3,4-trans)-1-(5-Ethoxy-2-fluorophenyl)-3-methylpiperidin-4-yl)oxy)-3-fluorophenyl)-4-(3-methoxypropoxy)-3-methylpyrrolidin-2-yl)acetic acid

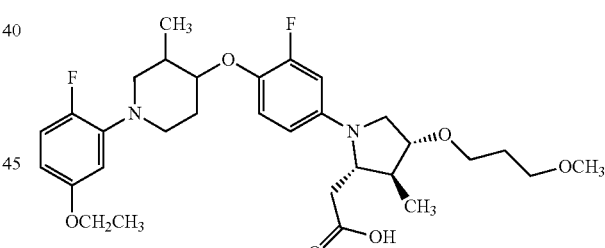

Example 20 (white solid, 43 mg) was prepared as a single isomer from 2-fluoro-4-iodophenol following the procedure of Example 14. LC-MS Anal. Calc'd for $C_{31}H_{42}F_2N_2O_6$: 576.67, found [M+H] 577.3. $^1$H NMR (400 MHz, $CD_2Cl_2$) δ 6.97-6.83 (m, 2H), 6.47 (dd, J=7.4, 3.0 Hz, 1H), 6.40-6.30 (m, 2H), 6.27 (dd, J=8.8, 1.8 Hz, 1H), 3.94 (q, J=7.0 Hz, 2H), 3.73 (d, J=4.0 Hz, 2H), 3.62 (td, J=9.1, 4.2 Hz, 1H), 3.59-3.34 (m, 9H), 3.28 (s, 3H), 2.85-2.73 (m, 1H), 2.67 (td, J=11.6, 2.5 Hz, 1H), 2.49 (dd, J=12.1, 9.9 Hz, 1H), 2.45-2.36 (m, 1H), 2.12-1.99 (m, 2H), 1.87-1.71 (m, 3H), 1.35 (t, J=7.0 Hz, 3H), 1.12 (d, J=6.6 Hz, 3H), 0.99 (d, J=7.0 Hz, 3H). Analytical HPLC (ZORBAX®, 0% B start): RT=8.5 min, HI: 100%. hGPR40 $EC_{50}$=110 nM.

Example 21, Isomer 1 and Isomer 2

2-((2S,3S,4R)-1-(4-(((3,4-trans)-1-(5-Chloro-2-methoxypyridin-4-yl)-3-methylpiperidin-4-yl)oxy)phenyl)-4-(3-methoxy-2-methylpropoxy)-3-methyl-pyrrolidin-2-yl)acetic acid

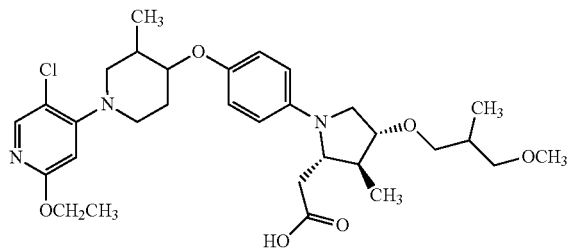 [SMILES: CCOc1cc(N2CCC(Oc3ccc(N4C[C@H](OCC(C)COC)[C@@H](C)[C@@H]4CC(=O)O)cc3)C(C)C2)c(Cl)cn1]

Example 21 was prepared from 3-bromo-2-methylprop-1-ene following the procedure of Example 1. The two isomers were separated by chiral SFC. Example 21, Isomer 1 (27.4 mg). LC-MS Anal. Calc'd for $C_{30}H_{42}ClN_3O_6$: 576.12, found [M+] 576.3. $^1$H NMR (500 MHz, DMSO-$d_6$) δ 8.01 (br. s., 1H), 6.88 (d, J=7.7 Hz, 2H), 6.47 (d, J=7.7 Hz, 2H), 6.40 (br. s., 1H), 3.92-3.83 (m, 1H), 3.80 (br. s., 3H), 3.70 (br. s., 1H), 3.59 (d, J=9.4 Hz, 1H), 3.35-3.22 (m, 7H), 3.20 (br. s., 3H), 3.17 (br. s., 1H), 2.88-2.80 (m, 1H), 2.69-2.61 (m, 1H), 2.60-2.52 (m, 1H), 2.27 (d, J=7.2 Hz, 1H), 2.08 (d, J=12.1 Hz, 1H), 1.91 (d, J=6.1 Hz, 2H), 1.57 (d, J=11.0 Hz, 1H), 1.29-1.19 (m, 1H), 1.04 (d, J=5.8 Hz, 3H), 0.92 (d, J=6.3 Hz, 3H), 0.87 (d, J=6.3 Hz, 3H). Analytical HPLC (Acquity): RT=2.0 min, HI: 94.6%. hGPR40 $EC_{50}$=120 nM. The second isomer was repurified by RP-Prep. HPLC to provide Example 21, Isomer 2, TFA (26.8 mg). LC-MS Anal. Calc'd for $C_{30}H_{42}ClN_3O_6$: 576.12, found [M+] 576.3. $^1$H NMR (500 MHz, DMSO-$d_6$) δ 8.02 (br. s., 1H), 6.88 (d, J=7.2 Hz, 2H), 6.49 (d, J=7.4 Hz, 2H), 6.40 (br. s., 1H), 3.86 (br. s., 1H), 3.80 (br. s., 3H), 3.71 (br. s., 1H), 3.43-3.23 (m, 8H), 3.21 (br. s., 3H), 3.17 (br. s., 1H), 2.87-2.81 (m, 1H), 2.69-2.53 (m, 3H), 2.26 (d, J=6.6 Hz, 1H), 2.08 (d, J=12.4 Hz, 1H), 1.92 (d, J=4.7 Hz, 2H), 1.58 (d, J=10.7 Hz, 1H), 1.05 (d, J=4.7 Hz, 3H), 0.93 (d, J=6.1 Hz, 3H), 0.87 (d, J=5.0 Hz, 3H). Analytical HPLC (Acquity): RT=2.0 min, HI: 94.6%. hGPR40 $EC_{50}$=100 nM.

Example 22

2-((2S,3S,4R)-1-(6-(((3,4-trans)-1-(5-Chloro-2-methoxypyridin-4-yl)-3-methylpiperidin-4-yl)oxy)-5-fluoropyridin-3-yl)-4-(3-methoxypropoxy)-3-methylpyrrolidin-2-yl) acetic acid

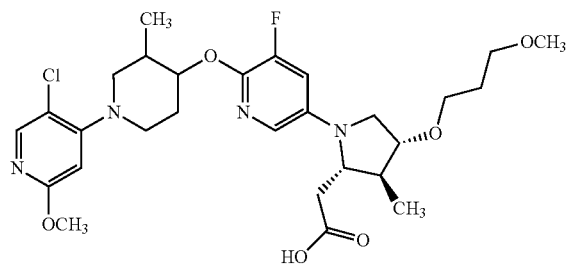 [SMILES: COCCCO[C@H]1CN(c2cnc(OC3CCN(c4cc(OC)ncc4Cl)CC3C)c(F)c2)[C@@H](CC(=O)O)[C@@H]1C]

22A. 2-(((3,4-trans)-1-(5-Chloro-2-methoxypyridin-4-yl)-3-methylpiperidin-4-yl)oxy)-3-fluoro-5-iodopyridine To a solution of 1P, Isomer 1 (410 mg, 1.60 mmol) in DMF (7 mL) at 0° C. was added 60% NaH (96 mg, 2.4 mmol). The reaction mixture was stirred at 0° C. for 10 min and then warmed to rt for 20 min. The reaction mixture was recooled to 0° C. and 2,3-difluoro-5-iodopyridine (385 mg, 1.60 mmol was added. The reaction mixture was warmed to rt and stirred for 105 min. The reaction mixture was cooled to 0° C. and quenched with sat. aq. $NH_4Cl$. The reaction mixture was partitioned between EtOAc/water. The aqueous phase was extracted with EtOAc (2×). The combined organic extracts were washed with water and brine, dried ($MgSO_4$), and concentrated. The crude product was purified by silica chromatography to give 22A (532 mg, 1.11 mmol, 70% yield) as a beige solid. LC-MS Anal. Calc'd for $C_{17}H_{18}ClFIN_3O_2$: 477.70, found [M+H] 478.0. $^1$H NMR (400 MHz, CDCl$_3$) δ 8.08 (d, J=1.8 Hz, 1H), 7.99 (s, 1H), 7.61 (dd, J=9.1, 1.9 Hz, 1H), 6.28 (s, 1H), 4.91 (td, J=9.2, 4.4 Hz, 1H), 3.92 (s, 3H), 3.64-3.53 (m, 2H), 3.01-2.90 (m, 1H), 2.68 (dd, J=12.3, 9.7 Hz, 1H), 2.34-2.19 (m, 2H), 1.95-1.81 (m, 1H), 1.06 (d, J=6.6 Hz, 3H).

22B. ((2R,3S,4R)-1-(6-(((3,4-trans)-1-(5-Chloro-2-methoxypyridin-4-yl)-3-methylpiperidin-4-yl)oxy)-5-fluoropyridin-3-yl)-4-(3-methoxypropoxy)-3-methylpyrrolidin-2-yl)methanol and ((2R,3S,4R)-1-(5-butoxy-6-(((3,4-trans)-1-(5-chloro-2-methoxypyridin-4-yl)-3-methylpiperidin-4-yl)oxy)pyridin-3-yl)-4-(3-methoxypropoxy)-3-methylpyrrolidin-2-yl)methanol To a pressure vial containing 22A (72.8 mg, 0.153 mmol) was added 1H (31 mg, 0.15 mmol), CuI (5.8 mg, 0.031 mmol) and NaOH (18.3 mg, 0.458 mmol), and n-BuOH (1 mL). The resulting suspension was bubbled with argon for 2 min, sealed, and stirred at 90° C. for 16 h. The reaction mixture was cooled to rt, diluted with water, and extracted with $CH_2Cl_2$ (3×). The combined organic extracts were washed with brine, dried (MgSO$_4$), and concentrated. The residue was purified by silica chromatography to provide ((2R,3S,4R)-1-(6-(((3,4-trans)-1-(5-chloro-2-methoxypyridin-4-yl)-3-methylpiperidin-4-yl)oxy)-5-fluoropyridin-3-yl)-4-(3-methoxypropoxy)-3-methylpyrrolidin-2-yl)methanol (54 mg, 0.083 mmol, 54% yield) and ((2R,3S,4R)-1-(5-butoxy-6-(((3,4-trans)-1-(5-chloro-2-methoxypyridin-4-yl)-3-methylpiperidin-4-yl)oxy)pyridin-3-yl)-4-(3-methoxypropoxy)-3-methylpyrrolidin-2-yl)methanol (~13%) as an inseparable mixture. ((2R,3S,4R)-1-(6-(((3,4-trans)-1-(5-Chloro-2-methoxypyridin-4-yl)-3-methylpiperidin-4-yl)oxy)-5-fluoropyridin-3-yl)-4-(3-methoxypropoxy)-3-methylpyrrolidin-2-yl)methanol. LC-MS Anal. Calc'd for $C_{27}H_{38}ClFN_4O_5$: 553.07, found [M+] 553.3. ((2R,3S,4R)-1-(5-Butoxy-6-(((3,4-trans)-1-(5-chloro-2-methoxypyridin-4-yl)-3-methylpiperidin-4-yl)oxy)pyridin-3-yl)-4-(3-methoxypropoxy)-3-methylpyrrolidin-2-yl)methanol. LC-MS Anal. Calc'd for $C_{31}H_{47}ClN_4O_6$: 606.32, found [M+H] 607.3.

Example 22 (off-white solid, 22.1 mg) was prepared as a single isomer from the inseparable mixture of 22B following the procedure of Example 1. LC-MS Anal. Calc'd for $C_{28}H_{38}ClFN_4O_6$: 581.08, found [M+] 581.3. $^1$H NMR (400 MHz, CDCl$_3$) δ 7.98 (s, 1H), 7.28 (d, J=2.6 Hz, 1H), 6.77 (dd, J=12.3, 2.6 Hz, 1H), 6.28 (s, 1H), 4.76 (td, J=9.1, 4.1 Hz, 1H), 3.90 (s, 3H), 3.76 (br. s., 1H), 3.73 (dd, J=8.3, 5.4

Hz, 1H), 3.64-3.42 (m, 8H), 3.33 (s, 3H), 2.94 (t, J=10.5 Hz, 1H), 2.84-2.78 (m, 2H), 2.71-2.61 (m, 1H), 2.45 (q, J=7.2 Hz, 1H), 2.33-2.18 (m, 2H), 1.92-1.79 (m, 3H), 1.07 (d, J=6.8 Hz, 3H), 1.02 (d, J=7.3 Hz, 3H). Analytical HPLC (ZORBAX®, 50% B start): RT=7.3 min, HI: 96.3%. hGPR40 $EC_{50}$=89 nM.

Example 23

2-((2S,3S,4R)-1-(5-Butoxy-6-(((3,4-trans)-1-(5-chloro-2-methoxypyridin-4-yl)-3-methylpiperidin-4-yl)oxy)pyridin-3-yl)-4-(3-methoxypropoxy)-3-methylpyrrolidin-2-yl)acetic acid, TFA

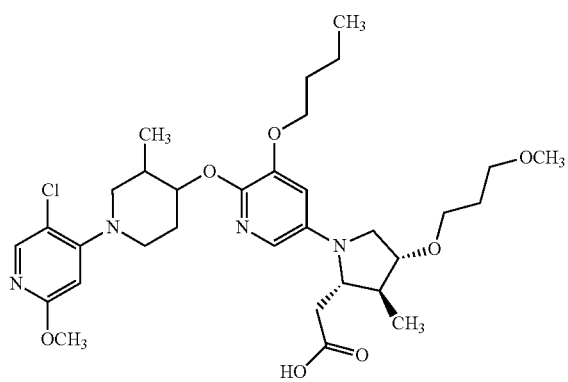 [SMILES: CCCCOc1cc(N2C[C@H](OCCCOC)[C@@H](C)[C@@H]2CC(=O)O)cnc1OC1CCN(c2cc(OC)ncc2Cl)CC1C]

Example 23 (grey solid, 2.6 mg) was isolated as a byproduct as a single isomer during the preparation of Example 22. LC-MS Anal. Calc'd for $C_{32}H_{47}ClN_4O_7$: 635.19, found [M+] 635.4. $^1$H NMR (400 MHz, CDCl$_3$) δ 8.11 (s, 1H), 7.21 (s, 1H), 6.88 (s, 1H), 6.30 (d, J=13.0 Hz, 1H), 4.90-4.76 (m, 1H), 4.09 (br. s., 1H), 4.01 (s, 3H), 3.89-3.64 (m, 3H), 3.61-3.43 (m, 5H), 3.34 (s, 3H), 3.30 (br. s., 1H), 3.23-3.02 (m, 1H), 2.99-2.68 (m, 2H), 2.61-2.43 (m, 2H), 2.41-2.16 (m, 2H), 2.02-1.70 (m, 7H), 1.58-1.42 (m, 2H), 1.13 (d, J=6.6 Hz, 3H), 1.05-0.97 (m, 6H). Analytical HPLC (ZORBAX®, 50% B start): RT=8.0 min, HI: 93.5%. hGPR40 $EC_{50}$=110 nM.

Example 24

2-((2S,3S,4R)-1-(6-(((3,4-trans)-1-(5-Chloro-2-methoxypyridin-4-yl)-3-methylpiperidin-4-yl)oxy)-5-(trifluoromethyl)pyridin-3-yl)-4-(3-methoxypropoxy)-3-methylpyrrolidin-2-yl)acetic acid

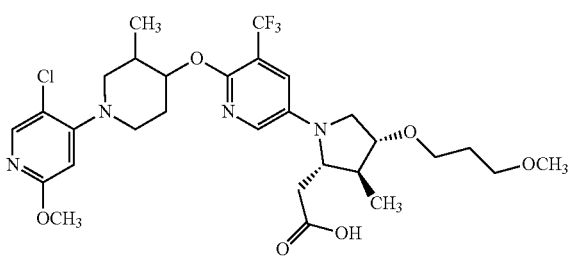 [SMILES: COCCCO[C@H]1CN(c2cnc(OC3CCN(c4cc(OC)ncc4Cl)CC3C)c(C(F)(F)F)c2)[C@@H](CC(=O)O)[C@@H]1C]

24A. (3,4-trans)-1-Benzyl-3-methylpiperidin-4-ol

To a solution of 1-benzyl-3-methylpiperidin-4-one (27.0 g, 133 mmol) in MeOH (80 mL) and water (200 mL) was added phosphoric acid (10.0 mL, 146 mmol) at −10° C. To this mixture, NaBH$_4$ (10.1 g, 266 mmol) was added in portions over a period of 1 h. The reaction mixture was slowly warmed to rt and stirred overnight. The reaction mixture was cooled to 0° C. and basified with 10% aq. NaOH (5 mL). The product was extracted with EtOAc (3×150 mL). The combined organic layers were dried (Na$_2$SO$_4$) and concentrated to give 24A (27.3 g, 133 mmol, 100% yield) as a brown gum. LC-MS Anal. Calc'd for $C_{13}H_{19}NO$: 205.30, found [M+H] 206.2. $^1$H NMR (400 MHz, CDCl$_3$) δ 7.36-7.28 (m, 4H), 7.26-7.21 (m, 1H), 3.48 (s, 2H), 3.20-3.09 (m, 1H), 2.91-2.83 (m, 1H), 2.82-2.75 (m, 1H), 2.03 (td, J=11.8, 2.5 Hz, 1H), 1.94-1.85 (m, 1H), 1.76-1.68 (m, 1H), 1.67-1.57 (m, 2H), 1.37 (d, J=5.0 Hz, 1H), 0.96 (d, J=6.0 Hz, 3H).

24B. (3,4-trans)-1-Benzyl-3-methylpiperidin-4-ol, Isomer 1 and Isomer 2

24A (37.0 g, 180 mmol) was purified by chiral SFC to provide 24B, Isomer 1 and Isomer 2 as brown oils. 24B, Isomer 1 (16.0 g, 78.0 mmol, 43% yield). LC-MS Anal. Calc'd for $C_{13}H_{19}NO$: 205.30, found [M+H] 206.0. $^1$H NMR (400 MHz, CDCl$_3$) δ 7.36-7.29 (m, 4H), 7.26-7.21 (m, 1H), 3.48 (s, 2H), 3.15 (br. s., 1H), 2.91-2.83 (m, 1H), 2.79 (dt, J=11.0, 3.0 Hz, 1H), 2.03 (td, J=11.8, 2.5 Hz, 1H), 1.90 (ddt, J=12.5, 4.5, 3.0 Hz, 1H), 1.75-1.67 (m, 1H), 1.67-1.57 (m, 2H), 1.38 (br. s., 1H), 0.96 (d, J=6.0 Hz, 3H). 24B, Isomer 2 (14.0 g, 68.2 mmol, 38% yield). LC-MS Anal. Calc'd for $C_{13}H_{19}NO$: 205.30, found [M+H] 206.2. $^1$H NMR (400 MHz, CDCl$_3$) δ 7.35-7.29 (m, 4H), 7.26-7.22 (m, 1H), 3.48 (s, 2H), 3.14 (td, J=9.9, 4.8 Hz, 1H), 2.91-2.83 (m, 1H), 2.79 (dt, J=10.9, 2.8 Hz, 1H), 2.03 (td, J=11.8, 2.5 Hz, 1H), 1.90 (ddt, J=12.4, 4.8, 2.9 Hz, 1H), 1.75-1.67 (m, 1H), 1.67-1.56 (m, 3H), 0.95 (d, J=6.0 Hz, 3H).

24C. (3,4-trans)-3-Methylpiperidin-4-ol

To a solution of 24B, Isomer 2 (14.0 g, 68.2 mmol) in MeOH (150 mL) was added 10% Pd/C (3.63 g). The reaction mixture was stirred at rt under H$_2$ (1 atm) overnight. The reaction mixture was filtered through CELITE® and the filtrate was concentrated to give 24C (7.50 g, 65.1 mmol, 95% yield) as an off-white solid. $^1$H NMR (400 MHz, CDCl$_3$) δ 3.21 (td, J=10.1, 4.4 Hz, 1H), 3.09 (ddt, J=12.6, 4.2, 2.4 Hz, 1H), 3.00 (ddd, J=12.7, 4.2, 1.6 Hz, 1H), 2.62 (td, J=12.5, 2.8 Hz, 1H), 2.31-2.18 (m, 1H), 1.99-1.88 (m, 1H), 1.48-1.31 (m, 2H), 0.97 (d, J=6.5 Hz, 3H).

24D. (3,4-trans)-1-(5-Chloro-2-methoxypyridin-4-yl)-3-methylpiperidin-4-ol

To a solution of 24C (7.50 g, 65.1 mmol) in DMSO (50 mL) at 0° C. was added K$_2$CO$_3$ (14 g, 98 mmol). After stirring for 15 min, 1J (14.5 g, 65.1 mmol) was added and the reaction mixture was heated to 110° C. overnight. The reaction mixture was cooled to rt and extracted with EtOAc (3×100 mL). The combined organic layers were dried (Na$_2$SO$_4$) and concentrated. The crude product was purified by silica chromatography to give 24D (13.2 g, 51.4 mmol, 79% yield) as a brown oil. LC-MS Anal. Calc'd for $C_{12}H_{17}ClN_2O_2$: 256.73, found [M+H] 257.0. $^1$H NMR (400 MHz, CDCl$_3$) δ 7.96 (s, 1H), 6.25 (s, 1H), 3.88 (s, 3H), 3.63-3.53 (m, 1H), 3.49 (ddd, J=12.3, 4.0, 2.8 Hz, 1H), 3.34 (tt, J=9.7, 4.8 Hz, 1H), 2.76 (td, J=11.8, 2.5 Hz, 1H), 2.43

(dd, J=12.0, 10.5 Hz, 1H), 2.08-2.01 (m, 1H), 1.86-1.67 (m, 2H), 1.49 (d, J=5.5 Hz, 1H), 1.06 (d, J=7.0 Hz, 3H).

24E. 2-(((3,4-trans)-1-(5-Chloro-2-methoxypyridin-4-yl)-3-methylpiperidin-4-yl)oxy)-5-iodo-3-(trifluoromethyl)pyridine To a solution of 24D (220 mg, 0.857 mmol) in DMF (4 mL) at rt was added 60% NaH (103 mg, 2.57 mmol) and the reaction mixture was stirred for 15 min. 2-Chloro-5-iodo-3-(trifluoromethyl)pyridine (277 mg, 0.900 mmol) was added and the resulting mixture was stirred at 120° C. for 12 h. The reaction was quenched with sat. aq. NaHCO$_3$ and extracted with EtOAc (3×25 mL). The combined organic extracts were washed with water (3×) and brine, dried (Na$_2$S$_2$O$_4$), and concentrated to give the crude product. Purification via silica chromatography gave 24E (260 mg, 0.493 mmol, 58% yield) as a white oil. LC-MS Anal. Calc'd for C$_{18}$H$_{18}$ClF$_3$IN$_3$O$_2$: 527.71, found [M+H] 528.2. $^1$H NMR (400 MHz, CD$_2$Cl$_2$) δ 8.56-8.43 (m, 1H), 8.19-8.07 (m, 1H), 7.96 (s, 1H), 6.30 (s, 1H), 4.98 (td, J=9.0, 4.3 Hz, 1H), 3.86 (s, 3H), 3.52 (dt, J=12.2, 1.9 Hz, 2H), 2.95 (ddd, J=12.6, 10.3, 2.9 Hz, 1H), 2.69 (dd, J=12.3, 9.2 Hz, 1H), 2.32 (dtd, J=12.7, 4.6, 3.1 Hz, 1H), 2.27-2.13 (m, 1H), 1.93-1.77 (m, 1H), 1.06 (d, J=6.6 Hz, 3H).

Example 24 (white solid, 14 mg) was prepared as a single isomer from 24E following the procedure of Example 1. LC-MS Anal. Calc'd for C$_{29}$H$_{38}$ClF$_3$N$_4$O$_6$: 631.08, found [M+H] 631.3. $^1$H NMR (400 MHz, CD$_2$Cl$_2$) δ 7.95 (s, 1H), 7.68 (d, J=2.4 Hz, 1H), 7.20 (d, J=2.6 Hz, 1H), 6.29 (s, 1H), 4.84 (td, J=8.8, 4.2 Hz, 1H), 3.86 (s, 3H), 3.77 (br. s., 2H), 3.63-3.55 (m, 1H), 3.54-3.38 (m, 7H), 3.29 (s, 3H), 2.98-2.87 (m, 1H), 2.76 (br. s., 2H), 2.66 (dd, J=12.2, 9.4 Hz, 1H), 2.45 (q, J=6.2 Hz, 1H), 2.34-2.25 (m, 1H), 2.22-2.09 (m, 1H), 1.88-1.73 (m, 3H), 1.04 (d, J=6.6 Hz, 3H), 1.01 (d, J=7.0 Hz, 3H). Analytical HPLC: RT=12.5 min, HI: 95.4%. hGPR40 EC$_{50}$=65 nM.

Example 25

2-((2S,3S,4R)-1-(6-(((3,4-trans)-1-(5-Chloro-2-methoxypyridin-4-yl)-3-methylpiperidin-4-yl)oxy)-5-methylpyridin-3-yl)-4-(3-methoxypropoxy)-3-methylpyrrolidin-2-yl) acetic acid

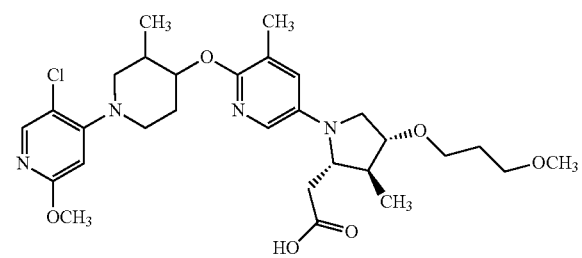 [SMILES: COCCCO[C@H]1CN(c2cnc(OC3CCN(c4cc(OC)ncc4Cl)CC3C)c(C)c2)[C@@H](CC(=O)O)[C@@H]1C]

Example 25 (yellow oil, 5 mg) was prepared as a single isomer from 2-chloro-5-iodo-3-methylpyridine following the procedure of Example 24. LC-MS Anal. Calc'd for C$_{29}$H$_{41}$ClN$_4$O$_6$: 577.11, found [M+] 577.4. $^1$H NMR (400 MHz, CD$_2$Cl$_2$) δ 7.93 (s, 1H), 7.36 (br. s., 1H), 6.89 (br. s., 1H), 6.28 (s, 1H), 4.74 (td, J=9.0, 4.1 Hz, 1H), 3.85 (s, 3H), 3.77-3.69 (m, 1H), 3.65 (d, J=6.4 Hz, 1H), 3.59-3.38 (m, 9H), 3.28 (s, 3H), 2.99-2.84 (m, 2H), 2.64 (dd, J=12.2, 9.6 Hz, 1H), 2.36 (br. s., 1H), 2.32-2.23 (m, 1H), 2.17 (s, 3H), 2.13-2.05 (m, 1H), 1.86-1.66 (m, 3H), 1.06-0.97 (m, 6H). Analytical HPLC (ZORBAX®, 0% B start): RT=8.6 min, HI: 95.6%. hGPR40 EC$_{50}$=300 nM.

Example 26

2-((2S,3S,4R)-1-(4-(((3,4-trans)-1-(5-Chloro-2-methoxypyridin-4-yl)-3-methylpiperidin-4-yl)oxy)-2-fluorophenyl)-4-(3-methoxypropoxy)-3-methylpyrrolidin-2-yl)acetic acid

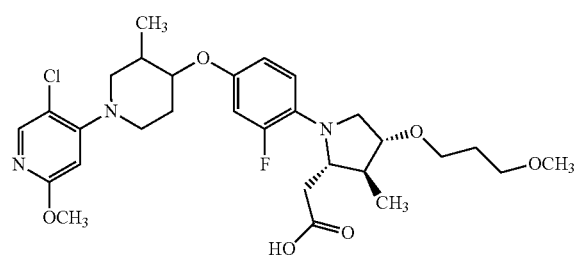 [SMILES: COCCCO[C@H]1CN(c2ccc(OC3CCN(c4cc(OC)ncc4Cl)CC3C)cc2F)[C@@H](CC(=O)O)[C@@H]1C]

Example 26 (colorless oil, 25 mg) was prepared as a single isomer from 3-fluoro-4-iodophenol following the procedure of Example 1. LC-MS Anal. Calc'd for C$_{29}$H$_{39}$ClFN$_3$O$_6$: 580.09, found [M+] 580.4. $^1$H NMR (500 MHz, CD$_2$Cl$_2$) δ 7.96 (s, 1H), 6.99 (t, J=9.1 Hz, 1H), 6.79-6.67 (m, 2H), 6.29 (s, 1H), 3.93 (td, J=8.8, 4.1 Hz, 1H), 3.86 (s, 3H), 3.72-3.64 (m, 1H), 3.57-3.48 (m, 5H), 3.47-3.42 (m, 3H), 3.31 (s, 3H), 3.24 (dd, J=10.5, 6.6 Hz, 1H), 2.94-2.84 (m, 1H), 2.65 (dd, J=12.4, 9.4 Hz, 1H), 2.59 (dd, J=16.8, 5.5 Hz, 1H), 2.52 (dd, J=16.8, 2.5 Hz, 1H), 2.23-2.16 (m, 1H), 2.16-2.09 (m, 2H), 1.87-1.74 (m, 3H), 1.18 (d, J=6.9 Hz, 3H), 1.10 (d, J=6.6 Hz, 3H). Analytical HPLC: RT=11.4 min, HI: 99.0%. hGPR40 EC$_{50}$=110 nM.

Example 27

2-((2R,3S,4R)-1-(4-(((3,4-trans)-1-(5-Chloro-2-methoxypyridin-4-yl)-3-methylpiperidin-4-yl)oxy)-2-fluorophenyl)-4-(3-methoxypropoxy)-3-methylpyrrolidin-2-yl)acetic acid

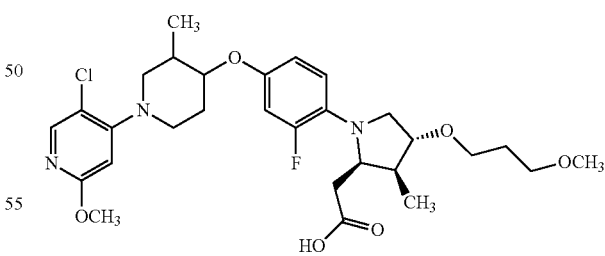

Example 27 (yellow oil, 6.6 mg) was obtained as a minor byproduct as a single isomer during the preparation of Example 26. LC-MS Anal. Calc'd for C$_{29}$H$_{39}$ClFN$_3$O$_6$: 580.09, found [M+] 580.4. $^1$H NMR (500 MHz, CD$_2$Cl$_2$) δ 7.96 (br. s., 1H), 7.00 (t, J=9.4 Hz, 1H), 6.75-6.66 (m, 2H), 6.29 (s, 1H), 4.18-4.10 (m, 1H), 3.92-3.87 (m, 2H), 3.86 (s, 3H), 3.71-3.67 (m, 1H), 3.54-3.48 (m, 3H), 3.48-3.43 (m, 1H), 3.40-3.35 (m, 2H), 3.24 (s, 3H), 2.99 (d, J=11.0 Hz, 1H), 2.92-2.78 (m, 1H), 2.69-2.61 (m, 1H), 2.59-2.49 (m, 2H), 2.43 (dd, J=16.8, 8.0 Hz, 1H), 2.24-2.16 (m, 1H), 2.15-2.07 (m, 1H), 1.84-1.73 (m, 3H), 1.10 (d, J=6.9 Hz, 3H), 1.07 (d, J=7.4 Hz, 3H). Analytical HPLC: RT=11.3 min, HI: 99.0%. hGPR40 EC$_{50}$=2000 nM.

Example 28

2-((2S,3S,4R)-1-(4-(((3,4-trans)-1-(5-Chloro-2-methoxypyridin-4-yl)-3-methylpiperidin-4-yl)oxy)phenyl)-4-((2-methoxyethoxy)methoxy)-3-methyl-pyrrolidin-2-yl)acetic acid

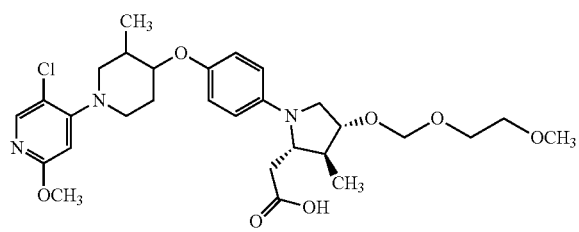 [SMILES: COCCOCO[C@H]1CN(c2ccc(OC3CCN(c4cc(OC)ncc4Cl)CC3C)cc2)[C@@H](CC(=O)O)[C@@H]1C]

Example 28 (off-white foam, 8 mg) was prepared as a single isomer from 2-methoxyethoxymethyl chloride following the procedure of Example 2. LC-MS Anal. Calc'd for C$_{29}$H$_{40}$ClN$_3$O$_7$: 578.10, found [M+] 578.4. $^1$H NMR (400 MHz, CDCl$_3$) δ 7.97 (s, 1H), 6.90 (d, J=9.0 Hz, 2H), 6.63 (d, J=9.0 Hz, 2H), 6.27 (s, 1H), 4.79 (d, J=1.1 Hz, 2H), 4.03 (dt, J=5.0, 2.4 Hz, 1H), 3.89 (s, 3H), 3.81 (td, J=8.6, 4.1 Hz, 1H), 3.75-3.71 (m, 2H), 3.68 (dt, J=8.8, 3.0 Hz, 1H), 3.60-3.55 (m, 2H), 3.55-3.45 (m, 4H), 3.40 (s, 3H), 2.88-2.72 (m, 3H), 2.63 (dd, J=12.3, 9.2 Hz, 1H), 2.40-2.32 (m, 1H), 2.22-2.08 (m, 2H), 1.87-1.76 (m, 1H), 1.14 (d, J=6.8 Hz, 3H), 1.08 (d, J=7.3 Hz, 3H). Analytical HPLC: RT=9.4 min, HI: 99.0%. hGPR40 EC$_{50}$=180 nM.

Example 29

2-((2S,3S,4R)-1-(4-(((3,4-trans)-1-(5-Chloro-2-methoxypyridin-4-yl)-3-methylpiperidin-4-yl)oxy)phenyl)-4-(3-ethoxypropoxy)-3-methylpyrrolidin-2-yl)acetic acid, TFA

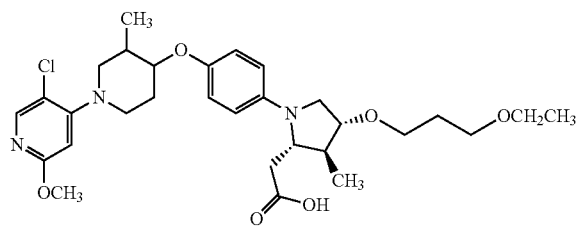 [SMILES: CCOCCCO[C@H]1CN(c2ccc(OC3CCN(c4cc(OC)ncc4Cl)CC3C)cc2)[C@@H](CC(=O)O)[C@@H]1C]

Example 29 (brown solid, 45 mg) was prepared as a single isomer from ethyl iodide following the procedure of Example 1. LC-MS Anal. Calc'd for C$_{30}$H$_{42}$ClN$_3$O$_6$: 576.12, found [M+] 576.2. $^1$H NMR (400 MHz, DMSO-d$_6$) δ 8.02 (s, 1H), 6.88 (d, J=9.0 Hz, 2H), 6.48 (d, J=9.0 Hz, 2H), 6.40 (s, 1H), 3.86 (td, J=8.8, 4.0 Hz, 2H), 3.81 (s, 3H), 3.73 (d, J=5.0 Hz, 1H), 3.62-3.57 (m, 3H), 3.51-3.43 (m, 3H), 3.42-3.31 (m, 4H), 2.94-2.80 (m, 1H), 2.69-2.57 (m, 2H), 2.30-2.23 (m, 1H), 2.12-2.05 (m, 1H), 2.00-1.89 (m, 1H), 1.72 (quin, J=6.4 Hz, 2H), 1.65-1.53 (m, 1H), 1.09 (t, J=7.0 Hz, 3H), 1.05 (d, J=6.5 Hz, 3H), 0.94 (d, J=7.5 Hz, 3H). Analytical HPLC: RT=12.9 min, HI: 99.0%. hGPR40 EC$_{50}$=220 nM.

Example 30

2-((2S,3S,4R)-1-(6-((1-(5-Chloro-2-methoxypyridin-4-yl)piperidin-4-yl)oxy)-5-(trifluoromethyl)pyridin-3-yl)-4-(3-methoxypropoxy)-3-methylpyrrolidin-2-yl) acetic acid

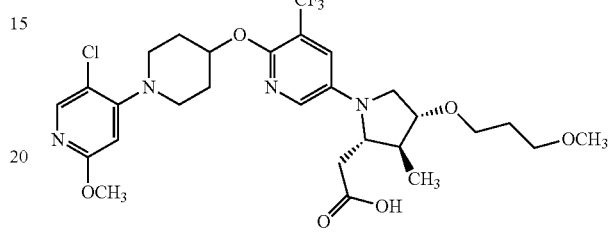

Example 30 (white solid, 4 mg) was prepared from 4A following the procedure of Example 24. LC-MS Anal. Calc'd for C$_{28}$H$_{36}$ClF$_3$N$_4$O$_6$: 617.06, found [M+] 617.3. $^1$H NMR (400 MHz, CD$_2$Cl$_2$) δ 7.94 (s, 1H), 7.67 (d, J=2.6 Hz, 1H), 7.18 (d, J=3.1 Hz, 1H), 6.30 (s, 1H), 3.85 (s, 3H), 3.77 (br. s., 2H), 3.58 (dt, J=9.0, 6.4 Hz, 1H), 3.53-3.42 (m, 5H), 3.41 (s, 3H), 3.36-3.30 (m, 1H), 3.29 (s, 3H), 3.17-3.09 (m, 2H), 2.76 (br. s., 1H), 2.47-2.38 (m, 1H), 2.15-2.06 (m, 2H), 2.01-1.93 (m, 2H), 1.81 (quin, J=6.2 Hz, 2H), 1.00 (d, J=7.3 Hz, 3H). Analytical HPLC: RT=11.8 min, HI: 98.0%. hGPR40 EC$_{50}$=61 nM.

Example 31

2-((2S,4R)-1-(4-(((3,4-trans)-1-(5-Chloro-2-methoxypyridin-4-yl)-3-methylpiperidin-4-yl)oxy)phenyl)-4-(3-methoxypropoxy)-3,3-dimethylpyrrolidin-2-yl)acetic acid

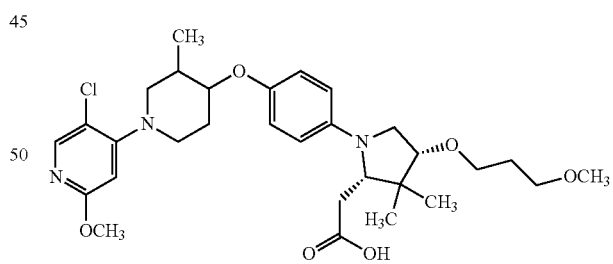

31A. (R)-2-Benzyl 1-tert-butyl 3,3-dimethyl-4-oxopyrrolidine-1,2-dicarboxylate

To a solution of (R)-2-benzyl 1-tert-butyl 4-oxopyrrolidine-1,2-dicarboxylate (3.00 g, 9.39 mmol) in THF (35 mL) at −78° C., was added a 1 M solution of LiHMDS in THF (10.3 mL, 10.3 mmol). The reaction mixture was stirred at −78° C. for 1 h. MeI (2.9 mL, 47 mmol) was added in one portion. The cold bath was removed and the reaction mixture was slowly warmed to rt and stirred for 2 h. The reaction was quenched with sat. aq. NH$_4$Cl, diluted with EtOAc, washed with water and brine, dried, and concentrated. The crude product was purified by silica chromatography to give 31A (506 mg, 1.46 mmol, 16% yield) as a white foam. LC-MS Anal. Calc'd for $C_{19}H_{25}NO_5$: 347.41, found [M+H-Boc] 248.2. $^1H$ NMR (400 MHz, $CDCl_3$) δ 7.18 (br. s., 5H), 5.17-4.86 (m, 2H), 4.34-4.11 (m, 1H), 3.98-3.72 (m, 2H), 1.33-1.20 (m, 9H), 1.14-1.09 (m, 3H), 0.87-0.82 (m, 3H).

31B. (2R)-2-Benzyl 1-tert-butyl 4-hydroxy-3,3-dimethylpyrrolidine-1,2-dicarboxylate To a solution of 31A (500 mg, 1.44 mmol) in THF (5 mL) was added to a suspension of $NaBH_4$ (218 mg, 5.76 mmol) in MeOH (5 mL) at 0° C. The reaction mixture was stirred at 0° C. for 1.5 h. The reaction was quenched with sat. aq. $NH_4Cl$ and diluted with EtOAc/water. The layers were separated and the organic layer was washed with brine, dried ($MgSO_4$), and concentrated. The crude product was purified by silica chromatography to provide 31B (453 mg, 1.30 mmol, 90% yield) as a colorless oil. LC-MS Anal. Calc'd for $C_{19}H_{27}NO_5$: 349.42, found [M+H-Boc] 250.2. $^1H$ NMR (400 MHz, $CDCl_3$) δ 7.48-7.29 (m, 5H), 5.42-5.06 (m, 2H), 4.07-3.87 (m, 1H), 3.85-3.59 (m, 3H), 1.52-1.31 (m, 9H), 1.12 (d, J=4.4 Hz, 3H), 1.03 (d, J=12.1 Hz, 3H).

Example 31 (white solid, 17 mg) was prepared as a single isomer from 31B following the procedure of Example 1. LC-MS Anal. Calc'd for $C_{30}H_{42}ClN_3O_6$: 576.12, found [M+] 576.5. $^1H$ NMR (500 MHz, methanol-$d_4$) δ 7.91 (s, 1H), 6.88 (d, J=8.8 Hz, 2H), 6.52 (d, J=9.1 Hz, 2H), 6.36 (s, 1H), 3.85 (s, 3H), 3.84-3.78 (m, 2H), 3.63 (dt, J=9.1, 6.1 Hz, 1H), 3.55-3.47 (m, 5H), 3.45 (dt, J=9.1, 6.0 Hz, 1H), 3.41-3.37 (m, 2H), 3.32 (s, 3H), 2.90-2.82 (m, 2H), 2.63 (dd, J=12.2, 9.7 Hz, 1H), 2.52 (dd, J=16.7, 2.3 Hz, 1H), 2.20-2.13 (m, 1H), 2.09-1.98 (m, 1H), 1.82 (quin, J=6.2 Hz, 2H), 1.75-1.65 (m, 1H), 1.16 (s, 3H), 1.13 (d, J=6.6 Hz, 3H), 0.98 (s, 3H). Analytical HPLC (ZORBAX®, 0% B start): RT=8.6 min, HI: 99.0%. hGPR40 $EC_{50}$=310 nM.

Example 32

2-((2S,3S,4R)-1-(4-(((3,4-trans)-1-(5-Chloro-2-methoxypyridin-4-yl)-3-methylpiperidin-4-yl)oxy)phenyl)-4-(3-cyanopropoxy)-3-methylpyrrolidin-2-yl)acetic acid

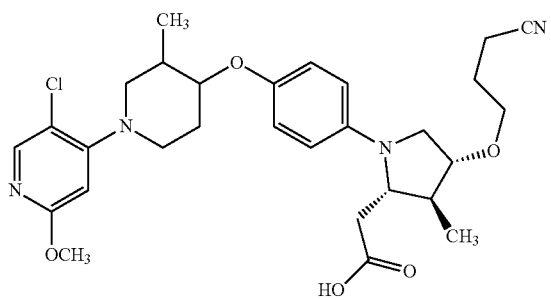 [SMILES: COc1cc(N2CCC(Oc3ccc(N4C[C@H](OCCCC#N)[C@@H](C)[C@@H]4CC(=O)O)cc3)C(C)C2)c(Cl)cn1]

32A. (2R,3S,4R)-1-Benzyl 2-methyl 4-(3-(methoxymethoxy)propoxy)-3-methylpyrrolidine-1,2-dicarboxylate To a stirred solution of 1E (0.130 g, 0.370 mmol) in $CH_2Cl_2$ (3 mL), at −10° C., DIPEA (0.32 mL, 1.9 mmol) and chloromethyl methyl ether (0.070 mL, 0.93 mmol) were added sequentially under nitrogen. The reaction mixture was warmed to rt and stirred overnight. The reaction mixture extracted with $CH_2Cl_2$ (2×), washed with sat. aq. $NaHCO_3$, water, and brine, dried ($Na_2SO_4$), and concentrated. The crude product was purified by silica chromatography to give 32A (0.100 g, 0.253 mmol, 68% yield) as gummy oil. LC-MS Anal. Calc'd for $C_{20}H_{29}NO_7$: 395.45, found [M+$H_2O$] 413.0. $^1H$ NMR (400 MHz, $CDCl_3$) δ 7.43-7.27 (m, 5H), 5.26-4.97 (m, 2H), 4.71-4.56 (m, 2H), 4.13-3.94 (m, 1H), 3.74 (s, 3H), 3.61-3.53 (m, 4H), 3.53-3.39 (m, 3H), 3.34 (d, J=3.5 Hz, 3H), 2.57-2.42 (m, 1H), 1.88-1.70 (m, 2H), 1.13 (dd, J=7.0, 2.0 Hz, 3H).

32B. 2-((2S,3S,4R)-1-(4-(((3,4-trans)-1-(5-Chloro-2-methoxypyridin-4-yl)-3-methylpiperidin-4-yl)oxy)phenyl)-4-(3-(methoxymethoxy)propoxy)-3-methyl-pyrrolidin-2-yl)acetic acid 32B was prepared from 32A following the procedure of Example 2. LC-MS Anal. Calc'd for $C_{30}H_{42}ClN_3O_7$: 592.12, found [M+] 592.4. $^1H$ NMR (400 MHz, DMSO-$d_6$) δ 12.20 (br. s., 1H), 8.01 (s, 1H), 6.92-6.85 (m, 2H), 6.48 (d, J=9.0 Hz, 2H), 6.40 (s, 1H), 4.56-4.50 (m, 2H), 3.86 (td, J=8.9, 4.3 Hz, 1H), 3.81 (s, 3H), 3.73 (d, J=4.0 Hz, 1H), 3.60 (d, J=7.5 Hz, 1H), 3.56-3.42 (m, 6H), 3.42-3.34 (m, 2H), 3.27-3.20 (m, 3H), 2.94-2.78 (m, 1H), 2.75-2.56 (m, 2H), 2.32-2.21 (m, 1H), 2.15-2.02 (m, 1H), 2.00-1.91 (m, 2H), 1.76 (quin, J=6.3 Hz, 2H), 1.65-1.51 (m, 1H), 1.05 (d, J=6.5 Hz, 3H), 0.94 (d, J=7.5 Hz, 3H).

32C. Ethyl 2-((2S,3S,4R)-1-(4-(((3,4-trans)-1-(5-chloro-2-methoxypyridin-4-yl)-3-methylpiperidin-4-yl)oxy)phenyl)-4-(3-hydroxypropoxy)-3-methylpyrrolidin-2-yl)acetate To a solution of 32B (0.035 g, 0.059 mmol) in EtOH (2 mL) was added $H_2SO_4$ (0.032 mL, 0.59 mmol). The reaction mixture was heated to 80° C. for 2 h. The reaction mixture was diluted with water and extracted with EtOAc (3×). The combined organic extracts were dried ($Na_2SO_4$) and concentrated. The crude product was purified by silica chromatography to give 32C (0.017 g, 0.030 mmol, 50% yield) as a brown gummy oil. LC-MS Anal. Calc'd for $C_{30}H_{42}ClN_3O_6$: 576.12, found [M+] 576.4.

32D. Ethyl 2-((2S,3S,4R)-1-(4-(((3,4-trans)-1-(5-chloro-2-methoxypyridin-4-yl)-3-methylpiperidin-4-yl)oxy)phenyl)-3-methyl-4-(3-((methylsulfonyl)oxy)propoxy) pyrrolidin-2-yl)acetate To a solution of 32C (0.015 g, 0.026 mmol) in $CH_2Cl_2$ (10 mL) at 0° C. was added $NEt_3$ (11 μl, 0.078 mmol), MsCl (4.1 μl, 0.052 mmol), and DMAP (3.2 μg, 0.026 μmol). The reaction mixture was stirred at 0° C. for 1 h. The reaction mixture was diluted with water and extracted with $CH_2Cl_2$. The organic layer was washed with 1.5 N aq. HCl, 10% aq. $NaHCO_3$, and brine, dried ($Na_2SO_4$), and concentrated to give 32D (0.016 g, 0.024 mmol, 94% yield) as a brown oil, which was used without further purification. LC-MS Anal. Calc'd for $C_{31}H_{44}ClN_3O_8S$: 654.21, found [M+] 654.2.

32E. Ethyl 2-((2S,3S,4R)-1-(4-(((3,4-trans)-1-(5-chloro-2-methoxypyridin-4-yl)-3-methylpiperidin-4-yl)oxy)phenyl)-4-(3-cyanopropoxy)-3-methylpyrrolidin-2-yl)acetate To a solution of 32D (0.016 g, 0.024 mmol) in DMSO (10 mL) was added NaCN (0.012 g, 0.25 mmol). The reaction mixture was heated to 50° C. overnight. The reaction mixture was diluted with water and extracted with EtOAc (3×). The combined organic layers were washed with brine, dried (Na₂SO₄), and concentrated to give 32E (0.0080 g, 0.014 mmol, 56% yield) as a brown oil. LC-MS Anal. Calc'd for C₃₁H₄₁ClN₄O₅: 585.13, found [M+] 585.2.

Example 32 (brown solid, 15 mg) was prepared from 32E following the procedure of Example 1. LC-MS Anal. Calc'd for C₃₁H₄₁ClN₄O₅: 585.13, found [M+] 585.2. ¹H NMR (400 MHz, DMSO-d₆) δ 8.01 (s, 1H), 6.88 (d, J=9.0 Hz, 2H), 6.48 (d, J=9.0 Hz, 2H), 6.40 (s, 1H), 3.86 (td, J=8.9, 4.3 Hz, 1H), 3.81 (s, 3H), 3.76 (d, J=4.5 Hz, 1H), 3.61 (d, J=10.5 Hz, 1H), 3.56-3.48 (m, 2H), 3.47 (d, J=3.5 Hz, 1H), 3.44 (d, J=2.5 Hz, 1H), 3.42-3.38 (m, 1H), 3.35 (br. s., 2H), 2.86 (t, J=10.3 Hz, 1H), 2.71-2.56 (m, 2H), 2.55-2.52 (m, 1H), 2.47-2.38 (m, 1H), 2.28 (q, J=7.4 Hz, 1H), 2.14-2.02 (m, 1H), 2.00-1.87 (m, 1H), 1.86-1.74 (m, 2H), 1.68-1.49 (m, 1H), 1.05 (d, J=6.5 Hz, 3H), 0.94 (d, J=7.0 Hz, 3H). Analytical HPLC (25 min gradient): RT=18.9 min, HI: 97.0%. hGPR40 EC₅₀=190 nM.

Example 33

2-((2S,3 S,4R)-1-(2-(((3R,4R)-1-(5-Chloro-2-methoxypyridin-4-yl)-3-methylpiperidin-4-yl)oxy) pyrimidin-5-yl)-4-(3-methoxypropoxy)-3-methylpyrrolidin-2-yl)acetic acid

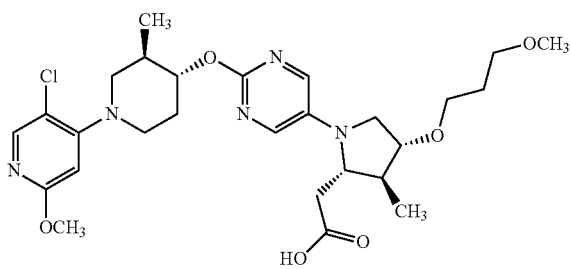 [SMILES: COCCCO[C@H]1CN(c2cnc(O[C@@H]3CCN(c4cc(OC)ncc4Cl)C[C@H]3C)nc2)[C@@H](CC(=O)O)[C@@H]1C]

33A. (2R,3S,4R)-Benzyl 2-(hydroxymethyl)-4-(3-methoxypropoxy)-3-methylpyrrolidine-1-carboxylate To a stirring suspension of ((2R,3S,4R)-4-(3-methoxypropoxy)-3-methylpyrrolidin-2-yl)methanol (0.950 g, 4.67 mmol) and sodium bicarbonate (0.491 g, 5.84 mmol) in a mixed solvent of DCM (10 mL) and water (10 mL) at rt was added benzyl carbonochloridate (0.843 mL, 5.61 mmol) dropwise over 5 min. After addition, the mixture was vigorously stirred at rt for 1 h, LC-MS showed the reaction was not complete. About 0.2 mL of benzyl chloroformate was added. After stirring for one more hour, the reaction was quenched with water. The mixture was extracted with EtOAc (3×). The combined organic extracts were washed with water and brine, dried (MgSO₄) and concentrated. The crude product was purified by flash chromatography eluting with hexane/EtOAc (0%-50%, 20 min; 50%, 10 min; 50-100%, 15 min; 100%, 10 min). The desired fractions were pooled, concentrated and dried in vacuum to afford 33A (0.954 g, 2.80 mmol, 60% yield) as a colorless oil. LC-MS Anal. Calc'd for C₁₈H₂₇NO₅: 337.19, found [M+H] 338.1. ¹H NMR (400 MHz, CDCl₃) δ 7.43-7.32 (m, 5H), 5.20-5.14 (m, 2H), 4.43 (dd, J=7.9, 3.1 Hz, 1H), 3.86-3.76 (m, 2H), 3.71-3.64 (m, 1H), 3.59-3.50 (m, 3H), 3.48-3.42 (m, 2H), 3.34 (s, 2H), 2.06-1.96 (m, 1H), 1.83 (quin, J=6.1 Hz, 2H), 1.14-1.07 (m, 3H), 1.16-1.07 (m, 3H).

33B. (2R,3S,4R)-Benzyl 4-(3-methoxypropoxy)-3-methyl-2-(((methylsulfonyl) oxy)methyl)pyrrolidine-1-carboxylate To a stirring solution of 33A (0.954 g, 2.83 mmol) in DCM (12 mL) cooled at 0° C. was added Et₃N (0.788 mL, 5.65 mmol), followed by methanesulfonyl chloride (0.330 mL, 4.24 mmol) dropwise over 5 min. After addition, the resulting cloudy solution was stirred at 0° C. for 1 h. LC-MS showed the reaction was complete. The reaction mixture was diluted with EtOAc, washed with water (2×), sat. aq. NaHCO₃, brine, dried (MgSO₄) and concentrated. The obtained oily residue was dried in high vacuum to afford 33B as an oily residue which was used in experiment 35C immediately.

33C. (2S,3 S,4R)-Benzyl 2-(cyanomethyl)-4-(3-methoxypropoxy)-3-methylpyrrolidine-1-carboxylate To a solution of 33B in DMSO (9 mL) was added NaCN (555 mg, 11.32 mmol). After addition, the mixture was stirred at 50° C. After stirring for 16 h, LC-MS showed the reaction was complete. The mixture was allowed to cool to rt, then quenched with water. The mixture was extracted with EtOAc (3×). The combined extracts were washed with water (2×), brine, dried (MgSO₄) and concentrated to dryness. The crude product was purified by flash chromatography eluting with EtOAc/hexanes (0-60%, 15 min; 60%, 10 min; 60-100%, 10 min) to afford 35C (830 mg, 2.372 mmol, 84% yield) as a colorless oil. LC-MS Anal. Calc'd for C₁₉H₂₆N₂O₄: 346.189, found [M+H] 347.1. ¹H NMR (400 MHz, CDCl₃) δ 7.49-7.32 (m, 5H), 5.30-5.06 (m, 2H), 3.85-3.41 (m, 8H), 3.35 (s, 3H), 3.04-2.71 (m, 2H), 2.53-2.34 (m, 1H), 1.84 (quin, J=6.2 Hz, 2H), 1.19-0.96 (m, 3H).

33D. 2-((2S,3 S,4R)-4-(3-Methoxypropoxy)-3-methylpyrrolidin-2-yl)acetonitrile To a solution of 33C (430 mg, 1.241 mmol) in EtOAc (25 mL) was added Pd/C (210 mg, 0.099 mmol) (5% dry basis, Degussa type). After purging with hydrogen (3×), the suspension was vigorously stirred at rt under a hydrogen balloon for 16 h. LC-MS showed the reaction was complete. The mixture was filtered and the collected catalyst washed with EtOAc. The filtrate was concentrated to dryness, dried in high vacuum for 30 min to afford 35D (251 mg, 1.123 mmol, 90% yield) as a pale yellow oil. LC-MS Anal. Calc'd for C₁₁H₂₀N₂O₂: 212.152, found [M+H] 213.4. ¹H NMR (400 MHz, CDCl₃) δ 3.48 (m, 1H), 3.43-3.34 (m, 4H), 3.29-3.22 (m, 4H), 3.09-3.01 (m, 1H), 2.99-2.85 (m, 2H), 2.58-2.37 (m, 2H), 1.88-1.69 (m, 3H), 1.05-1.01 (m, 3H).

33E. 5-Bromo-2-(((3R,4R)-1-(5-chloro-2-methoxypyridin-4-yl)-3-methylpiperidin-4-yl)oxy)pyrimidine To a stirring solution of (3R,4R)-1-(5-chloro-2-methoxypyridin-4-yl)-3-methylpiperidin-4-ol (350 mg, 1.363 mmol) in DMF (6 mL) cooled at 0° C. was added NaH (60% in mineral oil) (82 mg, 2.045 mmol) in one portion. The resulting suspension was stirred at 0° C. for 10 min, then at rt for 20 min. The resulting pale yellow solution was cooled again at 0° C., 5-bromo-2-chloropyrimidine (264 mg, 1.363 mmol) was added. The resulting brownish mixture was stirred at rt. LC-MS showed the reaction was not complete after 1.5 h. The reaction was allowed to continue stirring at rt overnight, then at 50° C. for 4 more h. The reaction mixture was cooled at 0° C., quenched by addition of sat. aq. NH₄Cl solution. The mixture was partitioned between EtOAc and water. The separated aqueous phase was extracted with EtOAc (2×). The combined extracts were washed with brine, dried (MgSO₄) and concentrated. The crude was purified by flash chromatography eluting with EtOAc/hexanes (0-20%, 20 min; 20%, 5 min; 20-40%, 10 min). The desired fractions were pooled, concentrated and dried in high vacuum to afford 33E (205 mg, 0.496 mmol, 36.3% yield) as a white solid. LC-MS Anal. Calc'd for $C_{16}H_{18}BrClN_4O_2$: 412.03, found [M+H] 412.9, 414.9 (bromine isotopes).

33F. 2-((2S,3 S,4R)-1-(2-(((3R,4R)-1-(5-Chloro-2-methoxypyridin-4-yl)-3-methylpiperidin-4-yl)oxy)pyrimidin-5-yl)-4-(3-methoxypropoxy)-3-methylpyrrolidin-2-yl)acetonitrile A reaction mixture of 33E (35 mg, 0.085 mmol), 35D (21.55 mg, 0.102 mmol), (2-biphenyl)di-tert-butylphosphine (5.05 mg, 0.017 mmol), sodium tert-butoxide (9.76 mg, 0.102 mmol) and $Pd_2(dba)_3$ (3.87 mg, 4.23 μmol) was stirred at 75° C. under argon for 16 h. LC-MS showed the reaction was not complete. Additional amount of $Pd_2(dba)_3$ (3.87 mg, 4.23 μmol) and (2-biphenyl)di-tert-butylphosphine (5.05 mg, 0.017 mmol) were added to the reaction mixture, which was heated at 110° C. for 4 more hours. After cooling to rt, the reaction mixture was diluted with water, extracted with DCM (3×). The combined organics were washed with brine, dried (MgSO₄) and concentrated to give a dark oily residue. The crude product was purified by flash chromatography eluting with EtOAc/hexanes (0-30%, 15 min; 30%, 8 min; 30-50%, 10 min, 50%, 15 min). The desired fractions were pooled, concentrated to dryness to afford 33F (11 mg, 60% pure) as a glassy residue. LC-MS showed the product was contaminated with an oxidized (2-biphenyl)di-tert-butylphosphine (about 2:3 ratio to the desired product). LC-MS Anal. Calc'd for $C_{27}H_{37}ClN_6O_4$: 544.256, found [M+H] 545.3.

Example 33

To a microwave vial containing 33F (6 mg, 0.011 mmol) was added EtOH (0.2 mL) and 6 M solution of KOH (0.037 mL, 0.220 mmol). The reaction vial was sealed and stirred at 120° C. for 2.5 h. LC-MS showed the reaction was complete. The reaction was allowed to cool to rt and concentrated to remove most of the EtOH. The remaining aqueous phase was adjusted to pH=6 with 1 N aq. HCl, then extracted with DCM (3×). The combined extracts were washed with brine, dried (MgSO₄) and concentrated to dryness to give the crude product which was purified by prep HPLC. The desired fractions were pooled and concentrated to remove the volatiles. The remaining aqueous suspension was neutralized with sat. aq. NaHCO₃ to pH=6, then extracted with DCM (3×). The DCM extracts were washed with brine, dried (MgSO₄) and concentrated to give a glassy residue, which was lyophilized in AcCN/water to afford the desired product Example 35 (2.05 mg, 3.63 μmol, 33.0% yield) as an off-white lyophilate. LC-MS Anal. Calc'd for $C_{27}H_{38}ClN_5O_6$: 563.251, found [M+H] 564.3. ¹H NMR (400 MHz, CDCl₃) δ 7.89 (m, 3H), 6.21 (s, 1H), 4.63 (d, J=4.0 Hz, 1H), 3.82 (s, 3H), 3.71 (d, J=3.1 Hz, 2H), 3.61-3.34 (m, 8H), 3.31-3.22 (m, 3H), 2.95-2.80 (m, 1H), 2.78-2.67 (m, 2H), 2.58 (s, 1H), 2.40 (d, J=7.3 Hz, 1H), 2.31-2.09 (m, 2H), 1.79 (dt, J=12.3, 6.1 Hz, 4H), 1.01 (d, J=6.6 Hz, 3H), 0.96 (d, J=7.3 Hz, 3H). hGPR40 $EC_{50}$=101 nM.

What is claimed is:
1. A compound of Formula (I):

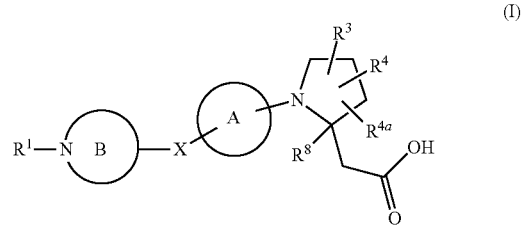

or a stereoisomer, a tautomer, a pharmaceutically acceptable salt or a solvate thereof, wherein:
X is independently selected from: a bond, O, S, NH, $N(C_{1-4}$ alkyl), $CH_2$, $CH_2CH_2$, $CH(C_{1-4}$ alkyl), $OCH_2$, $CH_2O$, $OCH_2CH_2$, and $CH_2CH_2O$;
ring A is independently

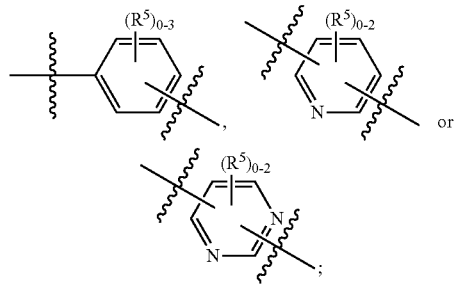

ring B is independently a 4- to 7-membered saturated heterocycle containing carbon atoms, the nitrogen atom shown in the ring B and 0-1 additional heteroatom selected from N, O, and S; and ring B is substituted with 0-4 $R^2$;
$R^1$ is independently

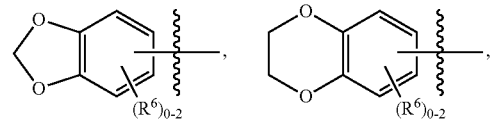

phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;
$R^2$, at each occurrence, is independently selected from: =O, OH, halogen, $C_{1-6}$ alkyl substituted with 0-1 $R^{12}$, $C_{1-6}$ alkoxy substituted with 0-1 $R^{12}$, $C_{1-4}$ haloalkyl substituted with 0-1 $R^{12}$, $C_{1-4}$ haloalkoxy substituted with 0-1 $R^{12}$, $—(CH_2)_m—C_{3-6}$ carbocycle substituted with 0-1 $R^{12}$, and $—(CH_2)_m$-(5- to 10-membered heteroaryl containing carbon atoms and 1-4 heteroatoms selected from N, $NR^{11}$, O, and S); wherein said heteroaryl is substituted with 0-1 $R^{12}$;

when two $R^2$ groups are attached to two different carbon atoms, they may combine to form a 1- to 3-membered carbon atom bridge over ring B;

when two $R^2$ groups are attached to the same carbon, they may combine, together with the carbon atom to which they are attached, to form a 3- to 6-membered carbon atom containing spiro ring;

$R^3$ is independently selected from: $C_{1-6}$ alkyl substituted with $R^{10}$, $C_{2-6}$ alkenyl substituted with $R^{10}$, $C_{2-6}$ alkynyl substituted with $R^{10}$, $C_{1-4}$ haloalkyl substituted with $R^{10}$, $-O(CH_2)_{1-20}(CH_2)_{1-4}R^{10}$, $OR^9$, $SR^9$, $C(O)OR^9$, $CO_2R^9$, $S(O)R^9$, $SO_2R^9$, and $CONHR^9$;

$R^4$ and $R^{4a}$ are independently selected from: H, halogen, $C_{1-6}$ alkyl, $C_{1-6}$ alkoxy, and $-(CH_2)_m-C_{3-6}$ carbocycle;

$R^5$, at each occurrence, is independently selected from: halogen, $C_{1-6}$ alkyl, $C_{1-6}$ haloalkyl, and $C_{1-6}$ haloalkoxy;

$R^6$, at each occurrence, is independently selected from: halogen, OH, $C_{1-4}$ alkylthio, CN, $SO_2(C_{1-2}$ alkyl), $N(C_{1-4}$ alkyl)$_2$, $C_{1-4}$ haloalkyl, $C_{1-4}$ haloalkoxy, $C_{1-8}$ alkyl substituted with 0-1 $R^7$, $C_{1-6}$ alkoxy substituted with 0-1 $R^7$, $-(O)_n-(CH_2)_m-(C_{3-10}$ carbocycle substituted with 0-2 $R^7$), and $-(CH_2)_m$-(5- to 10-membered heteroaryl containing carbon atoms and 1-4 heteroatoms selected from N, $NR^{11}$, O, and S); wherein said heteroaryl is substituted with 0-2 $R^7$;

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl)$_2$, $SO_2(C_{1-2}$ alkyl), and phenyl;

$R^8$ is independently selected from: H and $C_{1-4}$ alkyl;

$R^9$, at each occurrence, is independently selected from: $C_{1-6}$ alkyl substituted with substituted with $R^{10}$, and $C_{1-4}$ haloalkyl substituted with $R^{10}$;

$R^{10}$, at each occurrence, is independently selected from: CN, $C_{1-4}$ alkoxy, $C_{1-4}$ haloalkoxy, $CO_2(C_{1-4}$ alkyl), $SO_2(C_{1-4}$ alkyl), and tetrazolyl;

$R^{11}$, at each occurrence, is independently selected from: H, $C_{1-4}$ alkyl and benzyl;

$R^{12}$, at each occurrence, is independently selected from: OH, halogen, CN, $C_{1-4}$ alkyl, $C_{1-4}$ alkoxy, $C_{1-4}$ haloalkyl, $C_{1-4}$ haloalkoxy, $CO_2(C_{1-4}$ alkyl), and tetrazolyl;

m, at each occurrence, is independently 0, 1, or 2; and n, at each occurrence, is independently 0 or 1.

2. A compound according to claim 1, wherein $R^4$ is hydrogen and $R^8$ is hydrogen, further characterized by Formula (II):

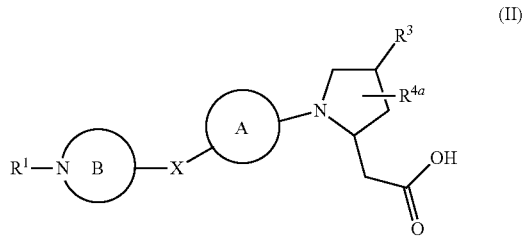

(II)

or a stereoisomer, a tautomer, a pharmaceutically acceptable salt or a solvate thereof, wherein:

X is independently selected from: O, N(CH$_3$), CH$_2$, CH$_2$O, and CH$_2$CH$_2$O;

ring A is independently

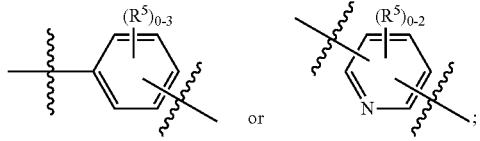

ring B is independently a 4- to 7-membered saturated heterocycle containing carbon atoms and the nitrogen atom shown in ring B; and ring B is substituted with 0-4 $R^2$;

$R^1$ is independently

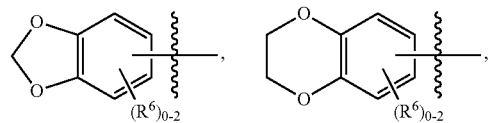

phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-4}$ alkyl substituted with 0-1 $R^{12}$, $C_{1-4}$ alkoxy substituted with 0-1 $R^{12}$, $C_{1-4}$ haloalkyl, $C_{1-4}$ haloalkoxy, and benzyl;

when two $R^2$ groups are attached to two different carbon atoms, they may combine to form a 1- to 3-membered carbon atom bridge over ring B;

when two $R^2$ groups are attached to the same carbon, they may combine, together with the carbon atom to which they are attached, to form a 3- to 6-membered carbon atom containing spiro ring;

$R^3$ is independently selected from: $C_{1-4}$ alkyl substituted with $R^{10}$, $C_{1-4}$ alkoxy substituted with $R^{10}$, $C_{1-4}$ haloalkyl substituted with $R^{10}$, $C_{1-4}$ haloalkoxy substituted with $R^{10}$, $OR^9$, and $-O(CH_2)_{1-20}(CH_2)_{1-4}R^{10}$;

$R^{4a}$ is independently selected from: H, halogen, $C_{1-4}$ alkyl, $C_{1-4}$ alkoxy, and $-(CH_2)_m-C_{3-6}$ carbocycle;

$R^5$, at each occurrence, is independently selected from: halogen, $C_{1-6}$ alkyl, $C_{1-6}$ haloalkyl, and $C_{1-6}$ haloalkoxy;

$R^6$, at each occurrence, is independently selected from: halogen, OH, $C_{1-4}$ alkylthio, CN, $SO_2(C_{1-2}$ alkyl), $N(C_{1-4}$ alkyl)$_2$, $C_{1-4}$ haloalkyl, $C_{1-4}$ haloalkoxy, $C_{1-8}$ alkyl substituted with 0-1 $R^7$, $C_{1-4}$ alkoxy substituted with 0-1 $R^7$, $-(O)_n-(CH_2)_m-(C_{3-6}$ carbocycle substituted with 0-2 $R^7$), $-(CH_2)_m$-(naphthyl substituted with 0-2 $R^7$), and $-(CH_2)_m$-(5- to 10-membered heteroaryl containing carbon atoms and 1-4 heteroatoms selected from N, O, and S; wherein said heteroaryl is substituted with 0-2 $R^7$);

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl)$_2$, $SO_2(C_{1-2}$ alkyl), and phenyl;

$R^9$, at each occurrence, is independently selected from: $C_{1-6}$ alkyl substituted with substituted with $R^{10}$, and $C_{1-4}$ haloalkyl substituted with $R^{10}$;

R¹⁰, at each occurrence, is independently selected from: CN, $C_{1-4}$ alkoxy, $C_{1-4}$ haloalkoxy, $CO_2(C_{1-4}$ alkyl), $SO_2(C_{1-4}$ alkyl), and tetrazolyl;

R¹¹, at each occurrence, is independently selected from: H, $C_{1-4}$ alkyl and benzyl;

R¹², at each occurrence, is independently selected from: halogen, CN, $C_{1-4}$ alkyl, $C_{1-4}$ alkoxy, $C_{1-4}$ haloalkyl, $C_{1-4}$ haloalkoxy, $CO_2(C_{1-4}$ alkyl), and tetrazolyl;

m, at each occurrence, is independently 0, 1, or 2; and n, at each occurrence, is independently 0 or 1.

3. A compound according to claim 2, wherein:

ring A is independently

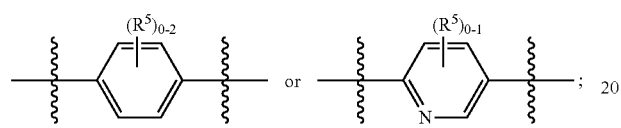

ring B is independently selected from:

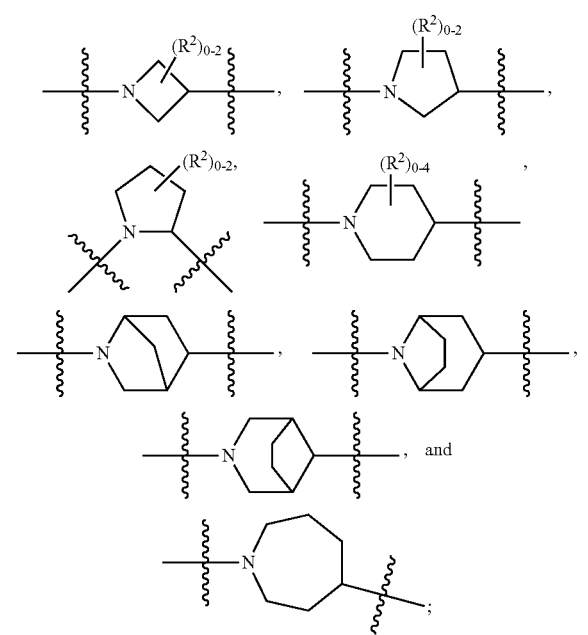

R¹ is independently

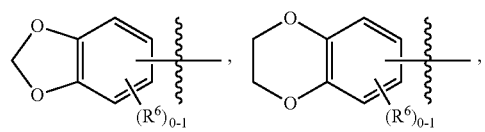

phenyl substituted with 0-3 R⁶ or a heteroaryl substituted with 0-2 R⁶; wherein said heteroaryl is selected from: furanyl, oxazolyl, thiazolyl, pyrazolyl, oxadiazolyl, pyridinyl, pyrimidinyl, pyrazinyl,

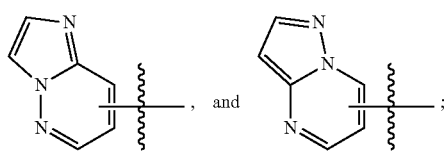

R², at each occurrence, is independently selected from: OH, halogen, $C_{1-4}$ alkyl substituted with 0-1 R¹², $C_{1-4}$ alkoxy substituted with 0-1 R¹², and benzyl;

R³ is independently selected from: $C_{1-4}$ alkyl substituted with 1 R¹⁰, $C_{1-4}$ alkoxy substituted with 1 R¹⁰, $C_{1-4}$ haloalkyl substituted with 1 R¹⁰, OR⁹, and $C_{1-4}$ haloalkoxy substituted with 1 R¹⁰;

R⁴ᵃ is independently selected from: H, halogen $C_{1-4}$ alkyl, $C_{1-4}$ alkoxy, and $C_{3-6}$ cycloalkyl;

R⁶, at each occurrence, is independently selected from: halogen, OH, $C_{1-6}$ alkyl substituted with 0-1 OH, $C_{1-4}$ alkoxy, $C_{1-4}$ alkylthio, $C_{1-4}$ haloalkyl, $C_{1-4}$ haloalkoxy, CN, $SO_2(C_{1-2}$ alkyl), $N(C_{1-4}$ alkyl)$_2$, $C_{3-6}$ cycloalkyl substituted with 0-2 $C_{1-4}$ alkyl, $C_{5-6}$ cycloalkenyl substituted with 0-2 $C_{1-4}$ alkyl, —O—$C_{3-6}$ cycloalkyl, benzyl, and oxazolyl;

R⁹, at each occurrence, is independently selected from: $C_{1-6}$ alkyl substituted with substituted with R¹⁰, and $C_{1-4}$ haloalkyl substituted with R¹⁰;

R¹⁰, at each occurrence, is independently selected from: CN, $C_{1-4}$ alkoxy, $C_{1-4}$ haloalkoxy, $CO_2(C_{1-4}$ alkyl), $SO_2(C_{1-4}$ alkyl), and tetrazolyl; and R¹², at each occurrence, is independently selected from: halogen, CN, $C_{1-4}$ alkyl, $C_{1-4}$ alkoxy, $C_{1-4}$ haloalkyl, $C_{1-4}$ haloalkoxy, $CO_2(C_{1-2}$ alkyl), and tetrazolyl.

4. A compound according to claim 3, wherein:

R¹ is independently

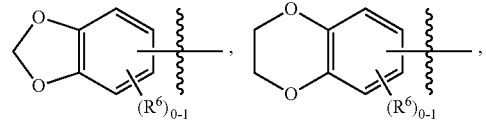

phenyl substituted with 0-3 R⁶, or a heteroaryl substituted with 0-2 R⁶; wherein said heteroaryl is selected from: thiazolyl, pyridinyl, pyrimidinyl, pyrazinyl,

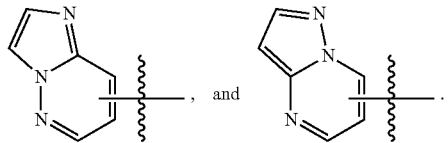

5. A compound according to claim 4, wherein:

ring B is independently selected from:

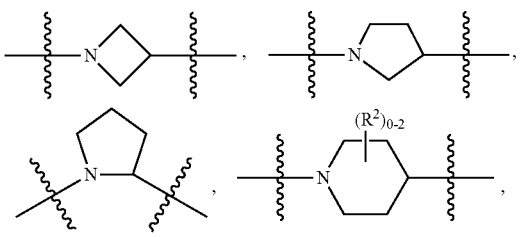

-continued

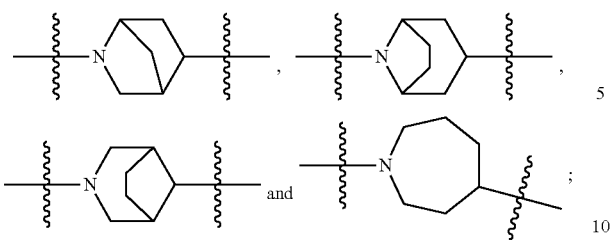

R[1] is independently phenyl substituted with 0-3 R[6], pyridinyl substituted with 0-2 R[6], pyrazinyl substituted with 0-2 R[6], pyrimidinyl substituted with 0-2 R[6], thiazolyl substituted with 0-2 R[6],

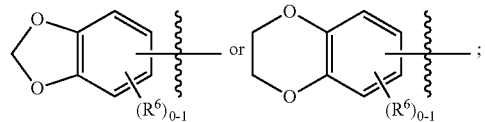

and
R[2], at each occurrence, is independently selected from: OH, halogen, $C_{1-4}$ alkyl substituted with 0-1 CN, $C_{1-4}$ alkoxy, benzyl, and tetrazolylmethyl.

6. A compound according to claim 5, wherein:
ring B is independently selected from:

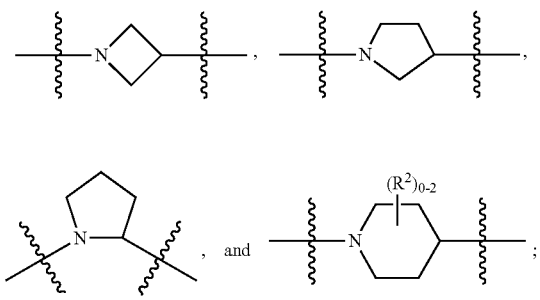

R[1], at each occurrence, is independently phenyl substituted with 0-3 R[6] or pyridinyl substituted with 0-2 R[6];
R[2], at each occurrence, is independently selected from: halogen, $C_{1-4}$ alkyl, $C_{1-4}$ alkoxy and tetrazolylmethyl;
R[3], at each occurrence, is independently selected from: $C_{1-4}$ alkyl substituted with R[10], $C_{1-4}$ alkoxy substituted with R[10], OR[9], and —O(CH$_2$)$_{1-20}$(CH$_2$)$_{1-4}$R[10];
R[6], at each occurrence, is independently selected from: halogen, $C_{1-6}$ alkyl, $C_{1-4}$ alkoxy, $C_{1-4}$ haloalkyl, $C_{1-4}$ haloalkoxy, $C_{3-6}$ cycloalkyl substituted with 0-2 $C_{1-4}$ alkyl, $C_{5-6}$ cycloalkenyl substituted with 0-2 $C_{1-4}$ alkyl, and benzyl;
R[9], at each occurrence, is independently selected from: $C_{1-6}$ alkyl substituted with substituted with R[10], and $C_{1-4}$ haloalkyl substituted with R[10]; and
R[10], at each occurrence, is independently selected from: CN, $C_{1-4}$ alkoxy, $C_{1-4}$ haloalkoxy, CO$_2$($C_{1-4}$ alkyl), SO$_2$($C_{1-4}$ alkyl), and tetrazolyl.

7. A compound of Formula (III), (IIIa), (IIIb) or (IIIc):

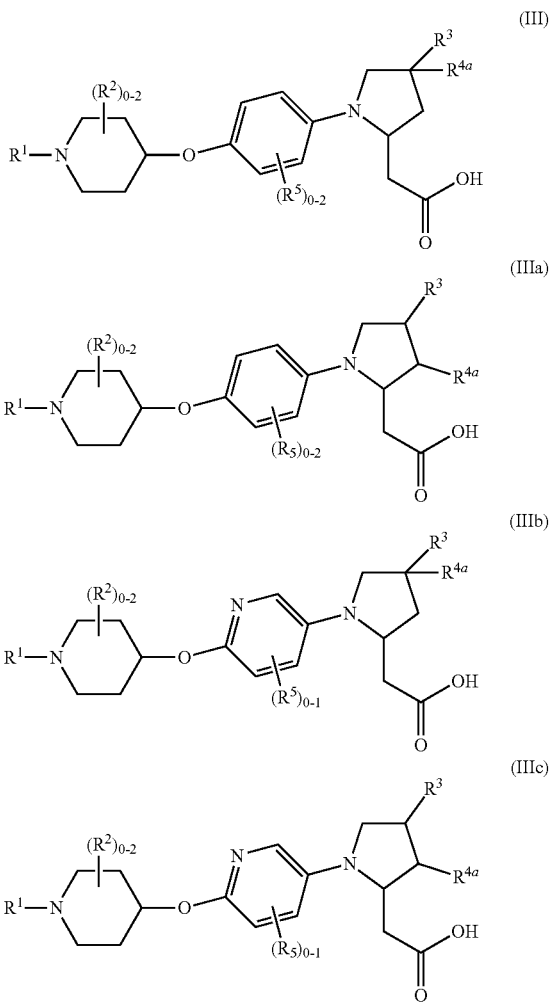

or a stereoisomer, a tautomer, a pharmaceutically acceptable salt or a solvate thereof, wherein:
R[1], at each occurrence, is independently phenyl substituted with 0-3 R[6] or pyridinyl substituted with 0-2 R[6];
R[2], at each occurrence, is independently selected from: halogen, $C_{1-4}$ alkyl, and $C_{1-4}$ alkoxy;
R[3], at each occurrence, is independently selected from: $C_{1-4}$ alkyl substituted with $C_{1-4}$ alkoxy, and $C_{1-4}$ alkoxy substituted with $C_{1-4}$ alkoxy;
R[4a], at each occurrence, is independently selected from: H, halogen, $C_{1-4}$ alkyl, $C_{1-4}$ alkoxy, and cyclopropyl;
R[5], at each occurrence, is independently selected from: halogen and $C_{1-4}$ haloalkyl; and
R[6], at each occurrence, is independently selected from: halogen, $C_{1-6}$ alkyl, $C_{1-4}$ alkoxy, $C_{3-6}$ cycloalkyl substituted with 0-2 $C_{1-4}$ alkyl, and $C_{5-6}$ cycloalkenyl substituted with 0-2 $C_{1-4}$ alkyl.

8. A compound of claim 7, wherein:
R[1], at each occurrence, is independently phenyl substituted with 0-3 R[6] or pyridinyl substituted with 0-2 R[6];
R[2], at each occurrence, is independently selected from: halogen and $C_{1-2}$ alkyl;
R[3], at each occurrence, is independently selected from: $C_{1-4}$ alkyl substituted with $C_{1-4}$ alkoxy, and $C_{1-4}$ alkoxy substituted with $C_{1-4}$ alkoxy;

$R^{4a}$, at each occurrence, is independently selected from: H and methyl;
$R^5$, at each occurrence, is independently selected from: halogen and $C_{1-4}$ haloalkyl; and
$R^6$, at each occurrence, is independently selected from: halogen, $C_{1-6}$ alkyl, and $C_{1-4}$ alkoxy.
9. A compound selected from:
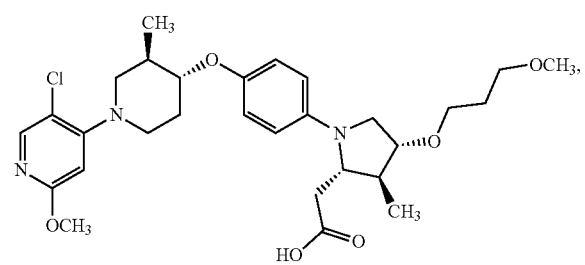
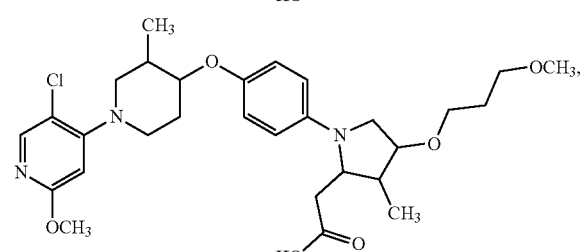
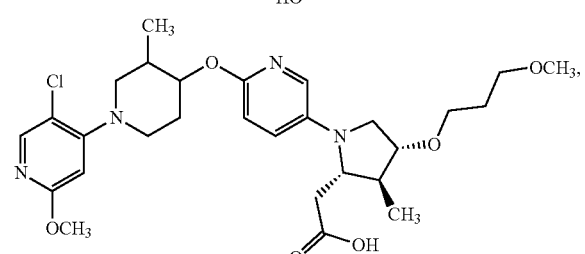
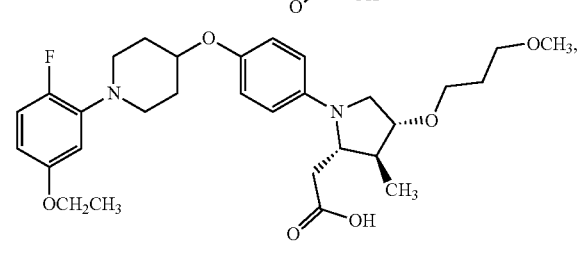
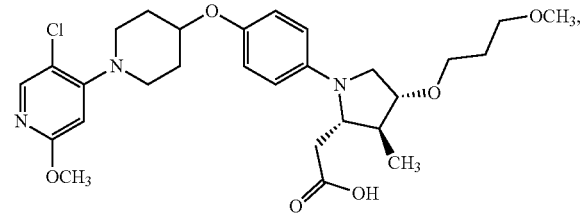
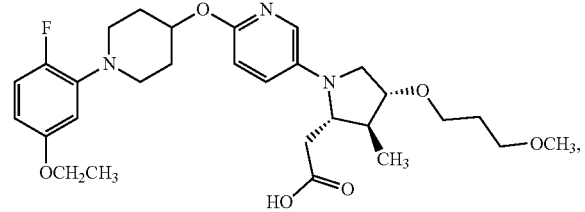
-continued
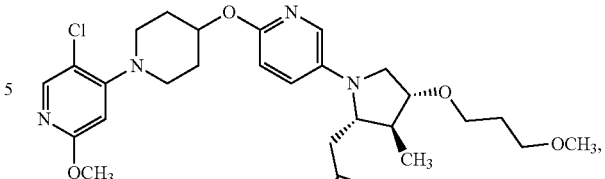
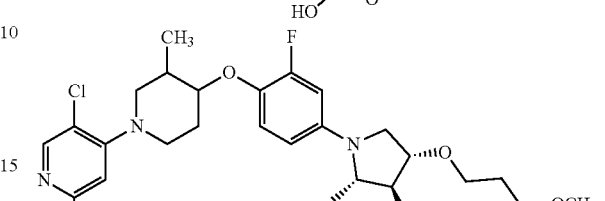
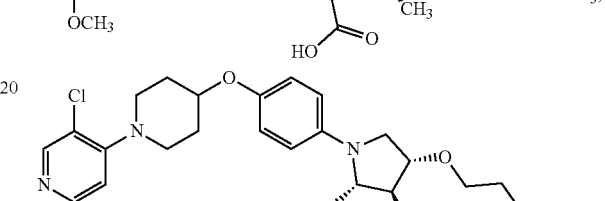
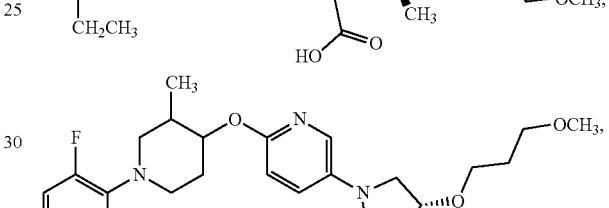
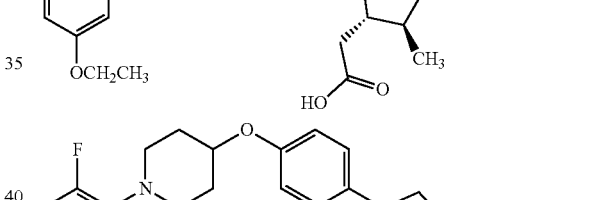
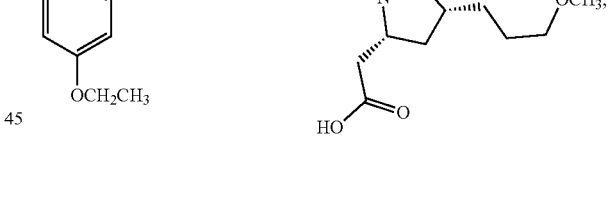
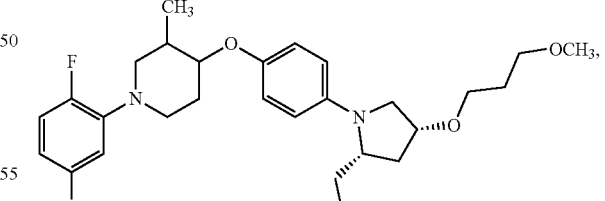
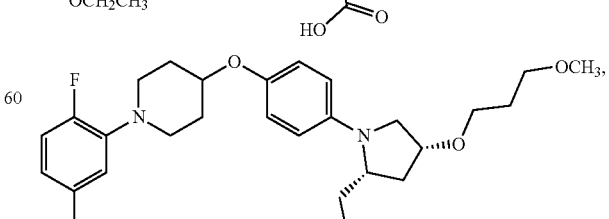

107
-continued
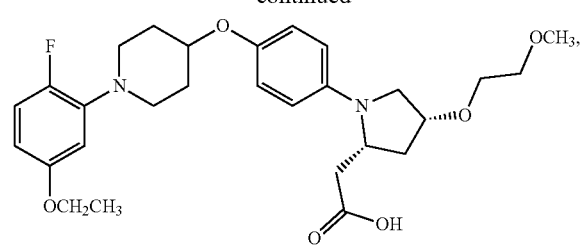
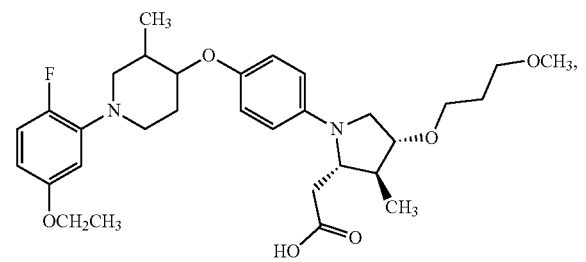
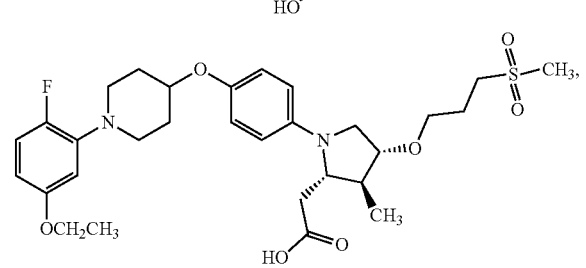
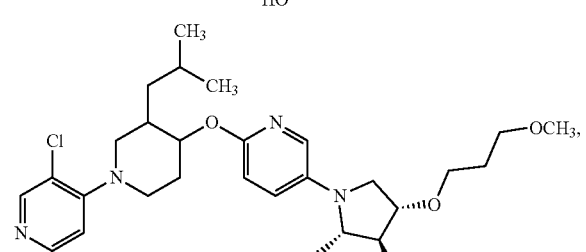
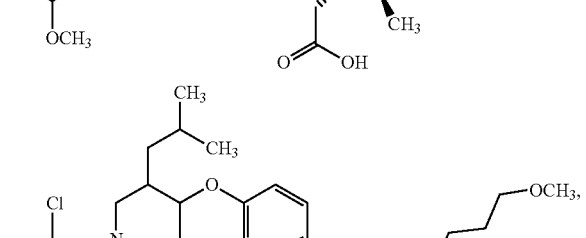
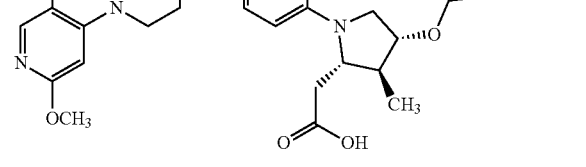
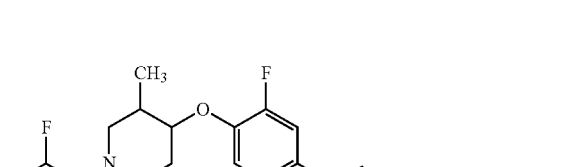
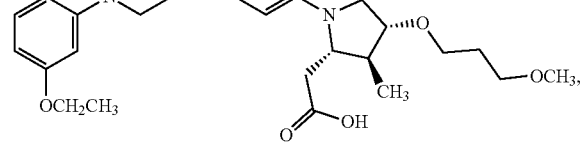
108
-continued
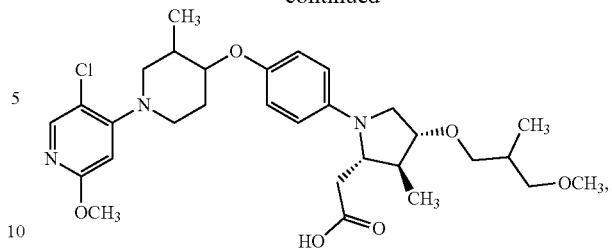
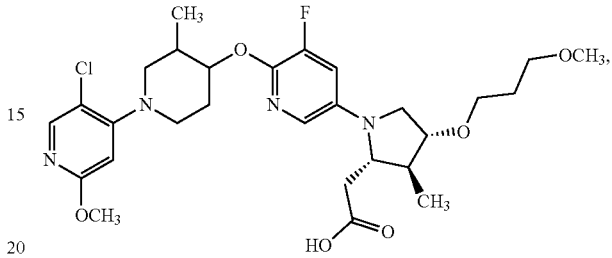
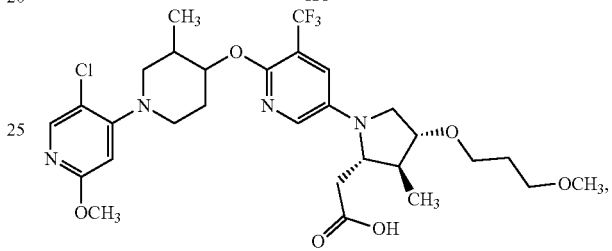
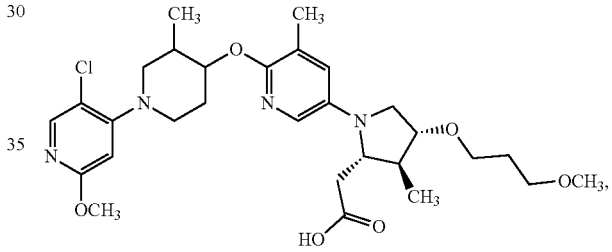
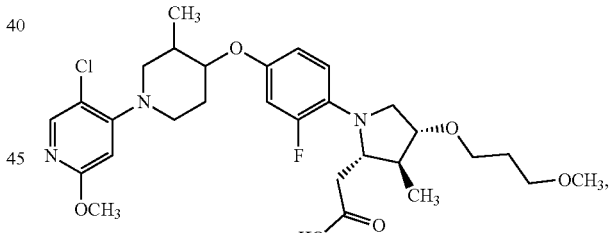
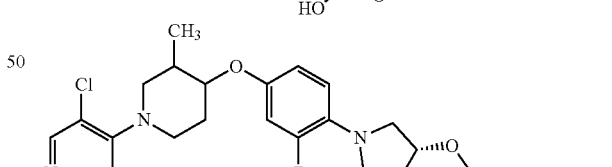
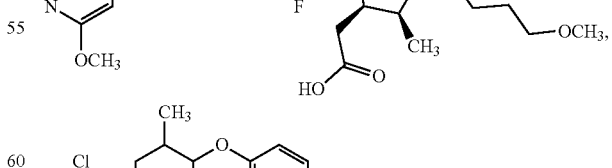
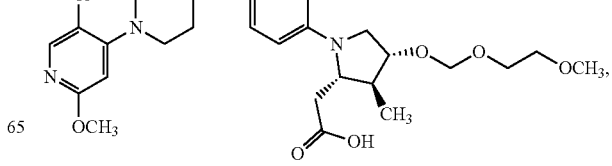

-continued

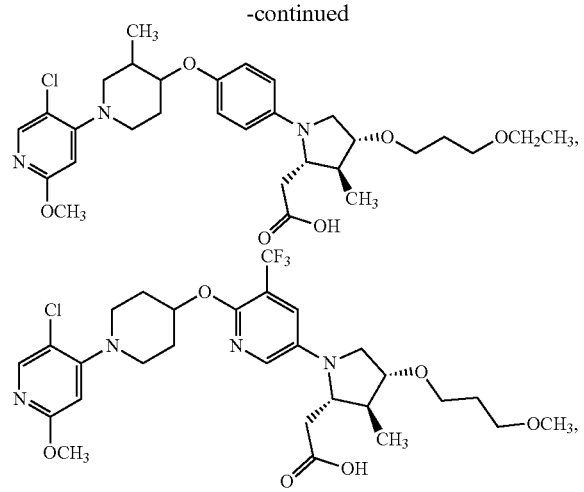

or a stereoisomer, a tautomer, a pharmaceutically acceptable salt or a solvate thereof.

10. A compound of claim 1, having the structure:

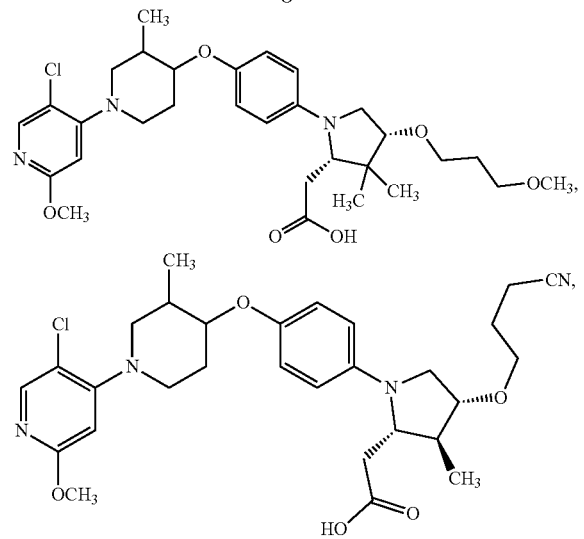

or a stereoisomer, a pharmaceutically acceptable salt or a solvate thereof.

11. A compound of claim 9, having the structure:

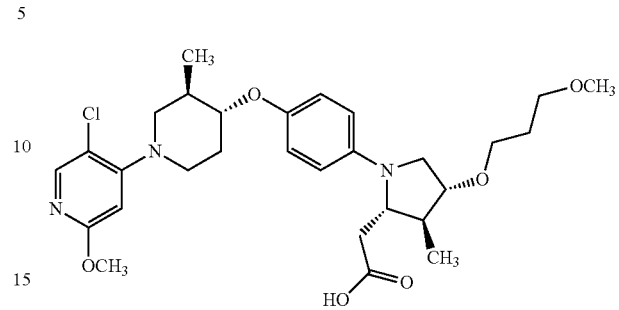

or a pharmaceutically acceptable salt or a solvate thereof.

12. A compound of claim 9, having the structure:

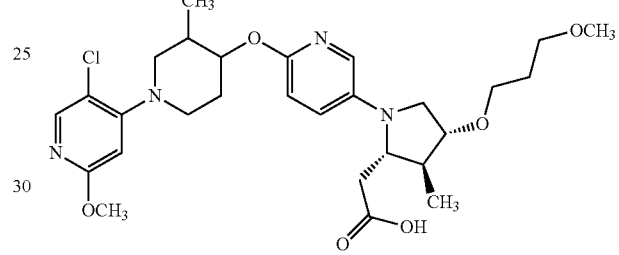

or a stereoisomer, a pharmaceutically acceptable salt or a solvate thereof.

13. A compound of claim 9, having the structure:

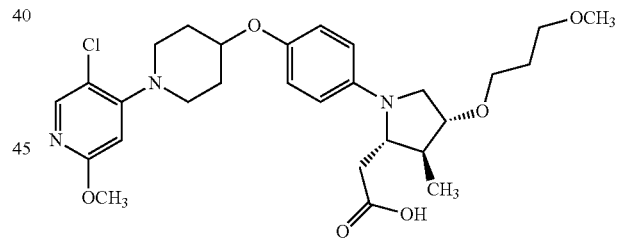

or a stereoisomer, a pharmaceutically acceptable salt or a solvate thereof.

14. A compound of claim 9, having the structure:

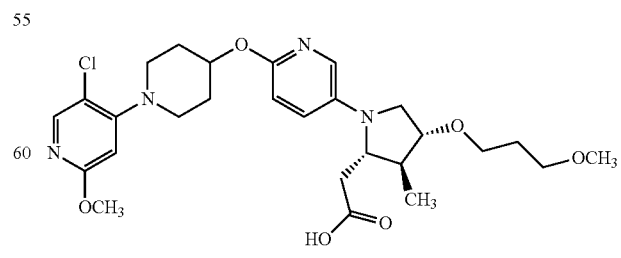

or a stereoisomer, a pharmaceutically acceptable salt or a solvate thereof.

15. A compound of claim 9, having the structure:

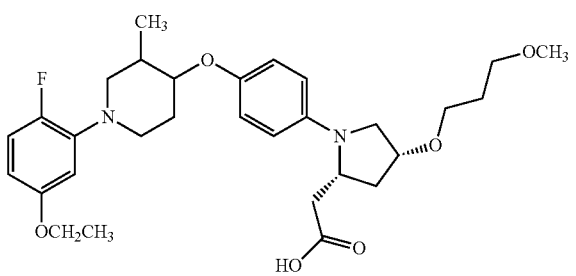 [SMILES: CCOc1ccc(F)c(N2CCC(Oc3ccc(N4C[C@H](OCCCOC)C[C@@H]4CC(=O)O)cc3)C(C)C2)c1]

or a stereoisomer, a pharmaceutically acceptable salt or a solvate thereof.

16. A compound of claim 9, having the structure:

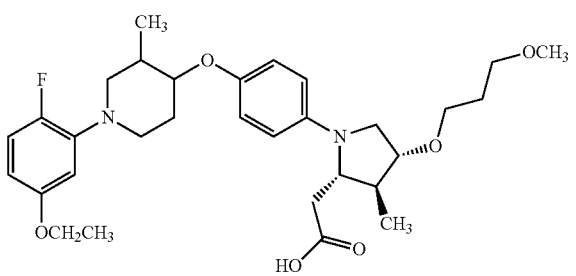 [SMILES: CCOc1ccc(F)c(N2CCC(Oc3ccc(N4C[C@H](OCCCOC)[C@@H](C)[C@@H]4CC(=O)O)cc3)C(C)C2)c1]

or a stereoisomer, a pharmaceutically acceptable salt or a solvate thereof.

17. A pharmaceutical composition, comprising a pharmaceutically acceptable carrier and a compound of claim 1.

18. The pharmaceutical composition according to claim 17, further comprising one or more other suitable therapeutic agents selected from: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, and appetite suppressants.

19. The pharmaceutical composition according to claim 17, further comprising a dipeptidyl peptidase-IV inhibitor and/or a sodium-glucose transporter-2 inhibitor.

20. A method for the treatment of a disease or disorder selected from diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), non-cardiac ischemia, pancreatitis, lipid disorders, NASH (Non-Alcoholic Steato-Hepatitis), NAFLD (Non-Alcoholic Fatty Liver Disease), liver cirrhosis; comprising administering to a patient in need of such treatment a therapeutically effective amount of a compound of claim 1, or a stereoisomer, a tautomer, a pharmaceutically acceptable salt or a solvate thereof.

* * * * *

UNITED STATES PATENT AND TRADEMARK OFFICE
CERTIFICATE OF CORRECTION

PATENT NO. : 10,717,725 B2
APPLICATION NO. : 16/211848
DATED : July 21, 2020
INVENTOR(S) : Elizabeth Jurica et al.

Page 1 of 1

It is certified that error appears in the above-identified patent and that said Letters Patent is hereby corrected as shown below:

Column 98
Line 12, Claim 1, "-O(CH$_2$)$_{1-20}$(CH$_2$)$_{1-4}$R$^{10}$", should read -- -O(CH$_2$)$_{1-2}$O(CH$_2$)$_{1-4}$R$^{10}$, --.

Column 100
Line 43, Claim 2, "-O(CH$_2$)$_{1-20}$(CH$_2$)$_{1-4}$R$^{10}$", should read -- -O(CH$_2$)$_{1-2}$O(CH$_2$)$_{1-4}$R$^{10}$, --.

Column 103

Line 3, Claim 5, after " 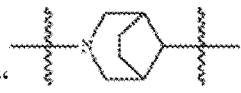 " insert -- , --.
Line 55, Claim 6, "-O(CH$_2$)$_{1-20}$(CH$_2$)$_{1-4}$R$^{10}$", should read -- -O(CH$_2$)$_{1-2}$O(CH$_2$)$_{1-4}$R$^{10}$, --.

Signed and Sealed this
Sixth Day of October, 2020

Andrei Iancu
*Director of the United States Patent and Trademark Office*